US012703723B2

(12) United States Patent
Bondy-Denomy et al.

(10) Patent No.: US 12,703,723 B2
(45) Date of Patent: Aug. 11, 2026

(54) CRISPR-Cas9-INHIBITING POLYPEPTIDE

(71) Applicant: The Regents of the University of California, Oakland, CA (US)

(72) Inventors: Joseph Bondy-Denomy, Oakland, CA (US); Benjamin Rauch, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 763 days.

(21) Appl. No.: 17/954,512

(22) Filed: Sep. 28, 2022

(65) Prior Publication Data

US 2023/0287058 A1 Sep. 14, 2023

Related U.S. Application Data

(62) Division of application No. 16/349,253, filed as application No. PCT/US2017/061932 on Nov. 16, 2017, now Pat. No. 11,485,760.

(60) Provisional application No. 62/422,850, filed on Nov. 16, 2016.

(51) Int. Cl.

*C07K 14/195* (2006.01)
*A61K 35/14* (2015.01)
*A61K 35/28* (2015.01)
*C12N 15/85* (2006.01)

(52) U.S. Cl.

CPC ............ *C07K 14/195* (2013.01); *A61K 35/14* (2013.01); *A61K 35/28* (2013.01); *C12N 15/85* (2013.01)

(58) Field of Classification Search

CPC .... C07K 14/195; C07K 14/005; A61K 35/14; C12N 15/85; C12N 9/22; C12N 15/74; C12N 15/902; A61P 43/00

See application file for complete search history.

(56) References Cited

U.S. PATENT DOCUMENTS

| | | | |
|---|---|---|---|
| 8,697,359 | B1 | 4/2014 | Zhang |
| 11,485,760 | B2 | 11/2022 | Bondy-Denomy et al. |
| 2006/0078901 | A1 | 4/2006 | Buchrieser et al. |
| 2010/0233200 | A1 | 9/2010 | Medin |
| 2014/0068797 | A1 | 3/2014 | Doudna et al. |

FOREIGN PATENT DOCUMENTS

| | | | |
|---|---|---|---|
| CN | 1292029 | A | 4/2001 |
| CN | 1896104 | A | 1/2007 |
| CN | 101084006 | A | 12/2007 |
| JP | 2004507217 | A | 3/2004 |
| WO | 2014093479 | A1 | 6/2014 |
| WO | 2014128659 | A1 | 8/2014 |
| WO | 2018093990 | A1 | 5/2018 |
| WO | 2019034784 | A1 | 2/2019 |
| WO | 2019093479 | A1 | 5/2019 |

OTHER PUBLICATIONS

"Conserved Hypothetical Protein Listeria Monocytogenes", DataBase: GenPept, CUL91420, Available Online at: https://www.ncbi.nlm.nih.gov/protein/CUL91420, Jan. 29, 2016, 1 page.

"Gp108", DataBase: UniProt, [online], Q30L37, Available Online at: https://www.uniprot.org/uniprot/Q30L37, Dec. 6, 2005, 1 page.

"Hypothetical Protein [Listeria Monocytogenes]", Available Online at: https://www.ncbi.nlm.nih.gov/protein/489818704?sat=, May 2013, 1 page.

"Hypothetical Protein [Listeria Monocytogenes]", NCBI Reference Sequence: WP_003722518.1, Available Online at: https://www.ncbi.nlm.nih.gov/protein/489818704?sat=46&satkey=125402324, May 24, 2013, 1 page.

"Hypothetical Protein Listeria Monocytogenes", Database: GenPept, WP_046376634, Available Online at: https://www.ncbi.nlm.nih.gov/protein/814561750?sat=47&satkey=98889600, Apr. 23, 2015, 1 page.

"Hypothetical Protein Listeria Monocytogenes", Database: GenPept, WP_069001216, Available Online at: https://www.ncbi.nlm.nih.gov/protein/1059898626?sat=47&satkey=98904541, Aug. 26, 2016, 1 page.

"Hypothetical Protein Listeria Monocytogenes", DataBase GenPept, WP_060954847, Available Online at: https://www.ncbi.nlm.nih.gov/protein/988800496?sat=47&satkey=98899024, Feb. 10, 2016, 1 page.

"Hypothetical Protein Listeria Monocytogenes", DataBase GenPept, WP_061107115, Available Online at: https://www.ncbi.nlm.nih.gov/protein/1000359812?sat=47&satkey=98899140, Feb. 24, 2016, 1 page.

"Hypothetical Protein Listeria Monocytogenes", DataBase: GenPept, WP_061385557, Available Online at: https://www. hcbi.nlm.nih.gov/protein/1002432309?sat=47&satkey=98899318, Mar. 2, 2016, 1 page.

"Hypothetical Protein Listeria Monocytogenes", DataBase: GenPept, WP_003740262, Available Online at: https://www.ncbi.nlm.nih.gov/protein/489836546?sat=47&satkey=98854487, May 13, 2013, 1 page.

"Hypothetical Protein Listeria Monocytogenes", Database: GenPept, KLI10194, Available Online at: https://www.ncbi.nlm.nih.gov/protein/KLI10194, May 22, 2015, 1 page.

(Continued)

*Primary Examiner* — Jeremy C Flinders
*Assistant Examiner* — Masudur Rahman
(74) *Attorney, Agent, or Firm* — Kilpatrick Townsend & Stockton LLP

(57) ABSTRACT

CRISPR-Cas9-inhibiting polypeptides, cells expressing the polypeptides, and polynucleotides encoding the polypeptides are provided. The Cas9-inhibiting polypeptides can be used in many aspects to inhibit unwanted Cas9 activity. For example, one or more Cas9-inhibiting polypeptides can be used to regulate Cas9 in genome editing, thereby allowing for some Cas9 activity prior to introduction of the Cas9-inhibiting polypeptide.

20 Claims, 23 Drawing Sheets

Specification includes a Sequence Listing.

(56) References Cited

OTHER PUBLICATIONS

"Hypothetical Protein Listeria Monocytogenes", DataBase: GenPept, WP_003723290, Available Online at: https://www.ncbi.nlm.nih.gov/protein/489819479?sat=17&satkey=16991215, May 7, 2013, 1 page.
"Hypothetical Protein Listeria Monocytogenes", DataBase GenPept, WP_070295973, Available Online at: https://www.ncbi.nlm.nih.gov/protein/1079979452?sat=47&satkey=98909136, Oct. 14, 2016, 1 page.
"Hypothetical Protein Listeria Monocytogenes", Database: Genpept, WP_031667946, Available Online at: https://www.ncbi.nlm.nih.gov/protein/685935189?sat=47&satkey=98875473, Sep. 19, 2014, 1 page.
"Hypothetical Protein LP110_021 [Listeria phage LP-110]", NCBI Reference Sequence: YP_008240385.1, Available Online at: https://www.ncbi.nlm.nih.gov/protein/526176509?sat=46&satkey=163033627, Jul. 31, 2014, 1 page.
"Phage Protein, Putative Listeria Monocytogenes", DataBase: GenPept, CAR82813, Available Online at: https://www.ncbi.nlm.nih.gov/protein/CAR82813 > (Newly cited documents, Feb. 27, 2015, 1 page.
"Uncharacterized Protein", DataBase UniProt, A0AOEOUT28, Available Online at: https://www.uniprot.org/uniprot/A0A0E0UT28, May 27, 2015, 1 page.
"Uncharacterized Protein", DataBase: UniProt, M4H0H1, Available Online at: https://www.uniprot.org/uniprot/M4H0H1, May 29, 2013, 1 page.
"Uncharacterized Protein", DataBase: UniProt, A0A068CBP6, Available Online at: https://www.uniprot.org/uniprot/A0A068CBP6, Oct. 1, 2014, 1 page.
"Uncharacterized Protein", DataBase: UniProt, A0A068CCW6, Available Online at: https://www.uniprot.org/uniprot/A0A068CCW6, Oct. 1, 2014, 1 page.
"Uncharacterized Protein", DataBase: UniProt, A0A076G604, Available Online at: https://www.uniprot.org/uniprot/A0A076G604, Oct. 29, 2014, 1 page.
"Uncharacterized Protein", DataBase: UniProt, A0A059T5N9, Available Online at: https://www.uniprot.org/uniprot/A0A059T5N9, Sep. 3, 2014, 1 page.
"Uncharacterized Protein", DataBase: UniProt, A0A059T899, Available Online at: https://www.uniprot.org/uniprot/A0A059T899, Sep. 3, 2014, 1 page.
"Uncharacterized Protein", DataBase: UniProt, A0A060AFL3, Available Online at: https://www.uniprot.org/uniprot/A0A060AFL3, Sep. 3, 2014, 1 page.
"Uncharacterized Protein", DataBase: UniProt, A0A060ALR2, Available Online at: https://www.uniprot.org/uniprot/A0A060ALR2, Sep. 3, 2014, 1 page.
U.S. Appl. No. 16/349,253 , "Non-Final Office Action", Feb. 23, 2022, 8 pages.
U.S. Appl. No. 16/349,253 , "Notice of Allowance", Jun. 23, 2022, 12 pages.
AU2017361379 , "First Examination Report", Feb. 20, 2023.
Bondy-Denomy , et al., "Bacteriophage Genes that Inactivate the CRISPR/Cas Bacterial Immune System", Nature, vol. 493, No. 7432, Jan. 17, 2013, pp. 429-432.
Bondy-Denomy , et al., "Multiple Mechanisms for CRISPR-Cas Inhibition by Anti-CRISPR Proteins", Nature, vol. 526, Sep. 2015, pp. 1-15.
Borowsky , et al., "Listeria Monocytogenes J0161 Hypothetical Protein", XX OS Listeria monocytogenes J0161 OC Bacteria, Available Online at: URL:https://www.ebi.ac.uk/ena/browser/api/embl/AE004689.1?lineLimit=1000, Sep. 8, 2011, 1 page.
CN201780071017.8 , "Office Action", Aug. 24, 2022, 11 pages.
Dorscht , et al., "Bacteriophages of Listeria Monocytogenes", Database Accession No. A8ATW7, XP055744738, Oct. 23, 2007, 1 page.
EP17872333.4 , "Extended European Search Report", Feb. 2, 2021, 12 pages.
EP17872333.4 , "Partial European Search Report", Nov. 6, 2020, 12 pages.
JP2019-547240 , "Notice of Decision to Grant", Dec. 8, 2022, 6 pages.
JP2019-547240 , "Office Action", Aug. 8, 2022, 6 pages.
JP2019-547240 , "Office Action", Feb. 16, 2022, 15 pages.
JP2019-547240 , "Office Action", Oct. 20, 2021, 13 pages.
KR10-2019-7017249 , "Office Action", May 27, 2022, 8 pages.
KR10-2019-7017249 , "Office Action", Nov. 28, 2022, 10 pages.
Pawluk , et al., "Inactivation of CRISPR-Cas Systems by Anti-CRISPR Proteins in Diverse Bacterial Species", Nature Microbiology, vol. 1, No. 8, Aug. 2016, pp. 1-6.
PCT/US2017/061932 , "International Preliminary Report on Patentability", May 31, 2019, 10 pages.
PCT/US2017/061932 , "International Search Report and Written Opinion", Mar. 13, 2018, 15 pages.
PCT/US2017/061932 , "Invitation to Pay Add'l Fees and Partial Search Report", Jan. 24, 2018, 2 pages.
Rauch , et al., "Inhibition of CRISPR-Cas9 with Bacteriophage Proteins", Cell, vol. 168, Issues 1-2, Jan. 12, 2017, pp. 150-158.
Timme , et al., "Listeria Monocytogenes Anti-CRISPR Protein AcrIIA4", EMBL Database, Available Online at: https://www.ebi.ac.uk/ena/browser/api/embl/AMD24318.1?lineLimit=1000, Accessed from Internet on Jan. 22, 2021, 1 page.
"Hypothetical Protein Listeria Monocytogenes", DataBase: GenPept, WP_061385557, Available Online at: https://www.ncbi.nlm.nih.gov/protein/1002432309?sat=47&satkey=98899318, Mar. 2, 2016, 1 page.
"Uncharacterized Protein", DataBase UniProt, A0A0E0UT28, Available Online at: https://www.uniprot.org/uniprot/A0A0E0UT28, May 27, 2015, 1 page.
"Hypothetical Protein Cg42_06730 listeria Monocytogenes", GenBank AMD 24318, Feb. 4, 2016, pp. 1-2.
CN201780071017.8 , "Notice of Decision to Grant", Mar. 21, 2024, 4 pages.
"NCBI Reference Sequence: WP_003723290.1", May 7, 2013.
Indian Application No. 201917023360, "First Examination Report", Jul. 2, 2026, 11 pages.
Ran et al., "Genome Engineering Using the CRISPR-Cas9", Nature Protocols, vol. 8, No. 11, Oct. 24, 2013, pp. 2281-2308.

FIG. 1A
FIG. 1B
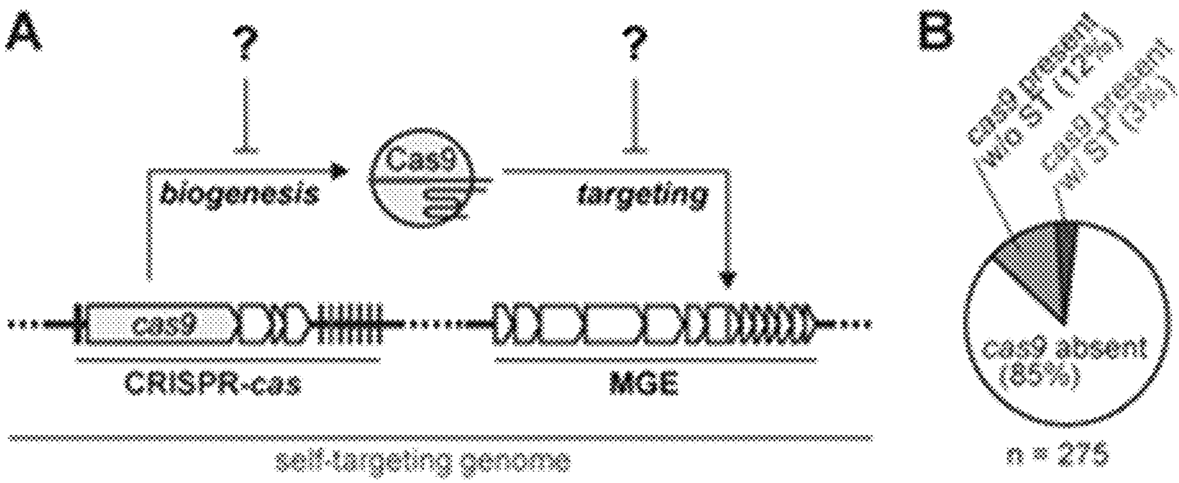
C
ST spacer
```
      5' GAUAGCAAGAUGGAUAGUUAGUUUUAGA...3'        crRNA
         ||||||||||||||||||||||
3'...GTATATGTCTATCGTTCTACCTATCAATGCCTCGCA...5'    protospacer
     ||||||||                    ||||||||          (ΦJ0161a
5'...CATATACAGATAGCAAGATGGATAGTTACGGAGCGT...3'    prophage)
                                  PAM
```
FIG. 1C FIG. 3A
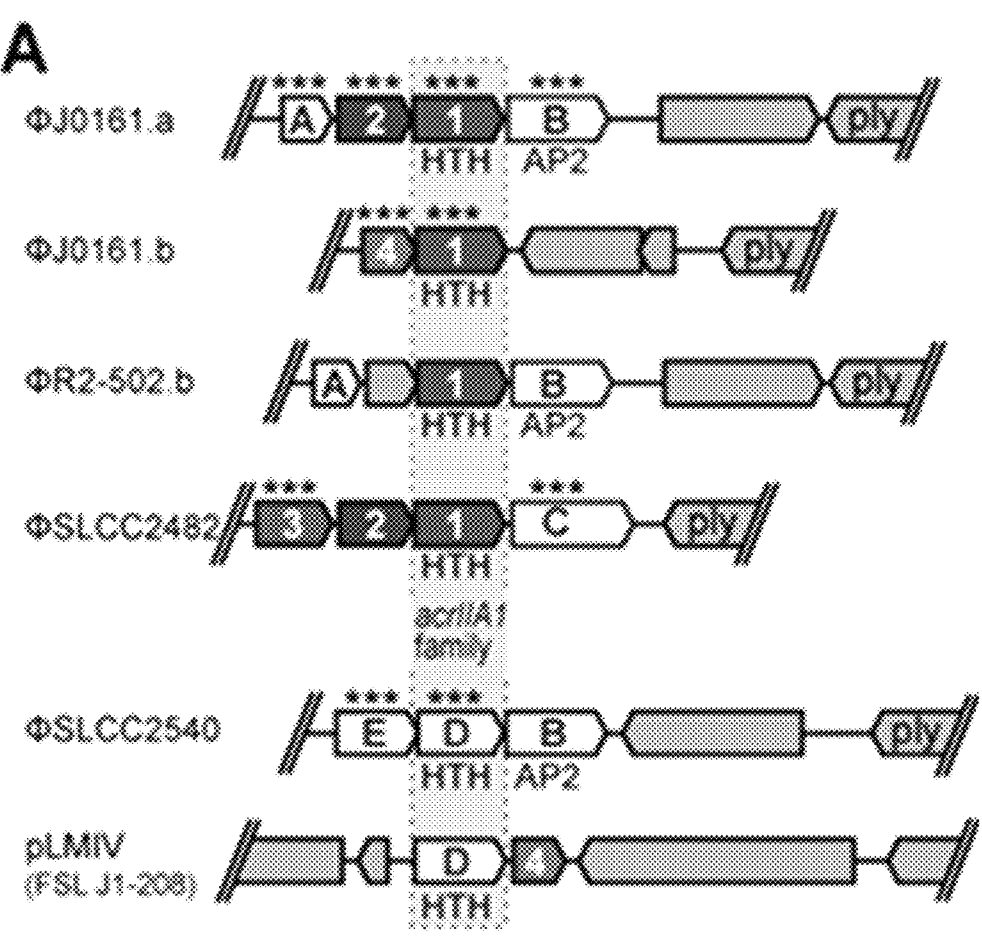
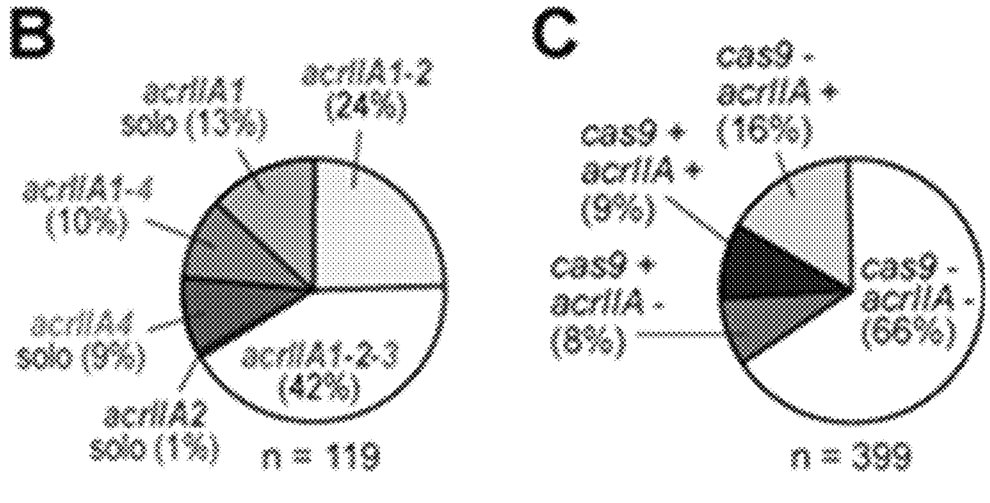
FIG. 3B
FIG. 3C

GRAPHICAL ABSTRACT

AcrIIA2 superfamily alignment

AcrIIA2a.1: Functions in Listeria, modest heterologous function

AcrIIA2b.1: Strong function in heterologous bacteria

AcrIIA2b.3: Strong function in heterologous bacteria

AcrIIA2c.1: Toxic in bacteria

| Name | %ID to AcrIIA2a.1 | Accession |
|---|---|---|
| AcrIIA2a.1 | 100 | WP_003722517.1 |
| AcrIIA2b.1 | 36 | WP_061112069.1 |
| AcrIIA2b.3 | 35 | KXX34219.1 |
| AcrIIA2c.1 | 50 | WP_015967155.1 |

53% ID (AcrIIA2b.1 / AcrIIA2b.3)

AcrIIA3 homolog searches

Listeria
3a
Streptococcus
3b
AcrIIA3 phylogeny
homologs confined to:
*Listeria* and *Streptococcus* siphophages

| Species | Cas9 %ID | acrIIA3 | Accession # | Acr %ID | Toxic? | Acr? |
|---|---|---|---|---|---|---|
| S. pyogenes | 100% | acrIIA3b.1 | WP_023611744.1 | 100% | YES | N/A |
| S. phocae | 70% | acrIIA3b.2 | KGR72913.1 | 67% | NO | YES |
| S. cuniculi | 63% | acrIIA3b.3 | OLF47316.1 | 39% | NO | YES |
| S. pseudopneuo. | 63% | acrIIA3b.4 | WP_049537331.1 | 46% | NO | YES |
| L. monocytogenes | 53% | acrIIA3a.1 | WP_014930691.1 | 43% | YES | N/A |

*FIG. 17*

- AcrIIA2
  - Original gene (2a) has modest activity in *E. coli, P. aeruginosa*, human.
  - New homolog (2b.1/2b.3) has enhanced activity in *P. aeruginosa*
  - New homolog (2c) is toxic in *P. aeruginosa*
- AcrIIA3
  - Original genes (3a, Lmo and 3b, Spy) were both toxic in *E. coli, P. aeruginosa* and non-toxic but non-functional in human
  - New homologs (3b.2, 3b.3, 3b.4, all from Streptococcal species) are functional and non-toxic in *P. aeruginosa*
- AcrIIA4
  - Original gene (4a) functions in *E. coli, P. aeruginosa,* human cells.
  - New homolog (4b) functional in *P. aeruginosa* but less active than 4a
  - New homolog (4c) is toxic in *P. aeruginosa*

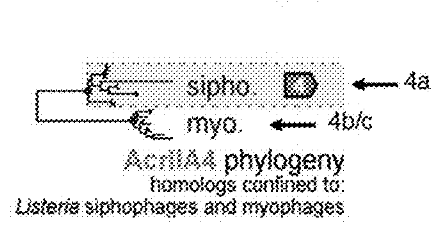

*FIG. 19*

SEQUENCE LISTING

```
Sequence total quantity: 209
SEQ ID NO: 1            moltype = AA  length = 149
FEATURE                 Location/Qualifiers
REGION                  1..149
                        note = Unknown bacterial, unknown viral (phage), or
                         syntheticCas9-inhibiting polypeptide
source                  1..149
                        mol_type = protein
                        organism = unidentified
SEQUENCE: 1
MTIKLLDEFL KKHDLTRYQL SKLTGISQNT LKDQNEKPLN KYTVSILRSL SLISGLSVSD  60
VLFELEDIEK NSDDLAGFKH LLDKYKLSFP AQEFELYCLI KEFESANIEV LPFTFNRFEN  120
EEHVNIKKDV CKALENAITV LKEKKNELL                                    149

SEQ ID NO: 2            moltype = AA  length = 149
FEATURE                 Location/Qualifiers
REGION                  1..149
                        note = Unknown bacterial, unknown viral (phage), or
                         syntheticCas9-inhibiting polypeptide
source                  1..149
                        mol_type = protein
                        organism = unidentified
SEQUENCE: 2
MTIKLLDEFL KKHDLTRYQL SKLTGISQNT LKDQNEKPLN KYTVSILRSL SLISGLSVSD  60
VLFELEDIEK NSDDLAGFKH LLDKYKLSFP AQEFELYCLI KEFESTNIEV LPFTFNRFEN  120
EEHVNIKKDV CKALENAITV LKEKKNELL                                    149

SEQ ID NO: 3            moltype = AA  length = 148
FEATURE                 Location/Qualifiers
REGION                  1..148
                        note = Unknown bacterial, unknown viral (phage), or
                         syntheticCas9-inhibiting polypeptide
source                  1..148
                        mol_type = protein
                        organism = unidentified
SEQUENCE: 3
MTIKLLDEFL KKHDLTRYQL SKLTGISQNT LKDQNEKPLN KYTVSILRSL SLISGLSVSD  60
VLFELEDIEK NSDDLAGFKH LLDKYKLSFP AQEFELYCLI KEFESNIEVL PFTFNRFENE  120
EHVNIGKDVC KALENAITVL KEKKNELL                                     148

SEQ ID NO: 4            moltype = AA  length = 149
FEATURE                 Location/Qualifiers
REGION                  1..149
                        note = Unknown bacterial, unknown viral (phage), or
                         syntheticCas9-inhibiting polypeptide
```

```
source                1..149
                      mol_type = protein
                      organism = unidentified
SEQUENCE: 4
MTIKLLDEFL KKHDLTRYQL SKLTGISQNT LKDQNEKPLN KYTVSILRSL SLISGLSVSD  60
VLFELEDIEK NSDDLAGFKH LLDKYKLSFP AQEFELYCLI KEFESANIEV LPFTFNRFEN  120
EEHVNIEKDV CKALENAITV LKEKKNELL                                   149

SEQ ID NO: 5          moltype = AA  length = 148
FEATURE               Location/Qualifiers
REGION                1..148
                      note = Unknown bacterial, unknown viral (phage), or
                       syntheticCas9-inhibiting polypeptide
source                1..148
                      mol_type = protein
                      organism = unidentified
SEQUENCE: 5
MTIKLLDEFL KKHDLTRYQL SKLTGISQNT LKDQNEKPLN KYTVSILRSL SLISGLSVSD  60
VLFELEDIEK NSDDLAGFKH LLDKYKLSFP AQEFELYCLI KEFESNIEVL PFTFNRFENE  120
KHVNIKKDVC KALENAITVL KEKKNELL                                    148

SEQ ID NO: 6          moltype = AA  length = 149
FEATURE               Location/Qualifiers
REGION                1..149
                      note = Unknown bacterial, unknown viral (phage), or
                       syntheticCas9-inhibiting polypeptide
source                1..149
                      mol_type = protein
                      organism = unidentified
SEQUENCE: 6
MTIKLLDEFL KKHDLTRYQL SKLTGISQNT LKDQNEKPLN KYTVSILRSL SLISGLSVSD  60
VLFELEDIEK NSDDLAGFKH LLNKYKLSFP AQEFELYCLI KEFESANIEV LPFTFNRFEN  120
EEHVNIEKDV CKALENAITV LKEKKNELL                                   149

SEQ ID NO: 7          moltype = AA  length = 149
FEATURE               Location/Qualifiers
REGION                1..149
                      note = Unknown bacterial, unknown viral (phage), or
                       syntheticCas9-inhibiting polypeptide
source                1..149
                      mol_type = protein
                      organism = unidentified
SEQUENCE: 7
MAIKLLDEFL KKHDLTRYQL SKLTGISQNT LKDQNEKPLN KYTVSILRSL SLISGLSVSD  60
VLFELEDIEK NSDDLAGFKH LLDKYKLSFP AQEFELYCLI KEFESANIEV LPFTFNRFEN  120
EKHVNIKKDV CKALENAITV LKEKKNELL                                   149

SEQ ID NO: 8          moltype = AA  length = 149
FEATURE               Location/Qualifiers
REGION                1..149
                      note = Unknown bacterial, unknown viral (phage), or
                       syntheticCas9-inhibiting polypeptide
source                1..149
                      mol_type = protein
                      organism = unidentified
SEQUENCE: 8
MSIKLLDEFL KKHNKTRYQL SKLTGISQNT LKDQNEKPLN KYTVSILRSL SLISGLSVSD  60
VLFELEDIEK NSDDLAGFKH LLDKYKLSFP AQEFELYCLI KEFESANIEV LPFTFNRFEN  120
EEHVNIEKDV CKALENAITV LKEKKNELL                                   149

SEQ ID NO: 9          moltype = AA  length = 147
FEATURE               Location/Qualifiers
REGION                1..147
                      note = Unknown bacterial, unknown viral (phage), or
                       syntheticCas9-inhibiting polypeptide
source                1..147
                      mol_type = protein
                      organism = unidentified
SEQUENCE: 9
MKLLDEFLKK HDLTRYQLSK LTGISQNTLK DQNEKPLNKY TVSILRSLSL ISGLSVSDVL  60
FELEDIEKNS DDLAGFKHLL DKYKLSFPAQ EFELYCLIKE FESANIEVLP FTFNRFENEK  120
HVNIKKDVCK ALENAITVLK EKKNELL                                     147

SEQ ID NO: 10         moltype = AA  length = 149
FEATURE               Location/Qualifiers
REGION                1..149
                      note = Unknown bacterial, unknown viral (phage), or
                       syntheticCas9-inhibiting polypeptide
source                1..149
```

```
                       mol_type = protein
                       organism = unidentified
SEQUENCE: 10
MTIKLLDEFL KKHDLTRYQL SKLTGISQNT LKDQNEKPLN KYTVSILRSL SLISGLSVSD  60
VLFELEDIEK NSDDLAGFKH LLNKYKLSFP AQEFELYCLI KEFESANIEV LPFTFNRFEN  120
ETHVDIEKDV RKALENAITV LKEKKNELL                                    149

SEQ ID NO: 11          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 11
MTIKLLDEFL KKHDLTRYQL SKLTGISQNT LKDQNEKPLN KYTVSILRSL SLISGLSVSD  60
VLFELEDIEK NSDDLAGFKH LLDKYKLSFP AQEFELYCLI KEFESANIEV LPFTFNRFEN  120
ETHVDIEKDV RKALENAITV LKEKKNELI                                    149

SEQ ID NO: 12          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 12
MTIKLLDEFL KKHDLTRYQL SKLTGISQNT LKDQNEKSLN KYTVSILRSL SLISGLSVSD  60
VLFELEDIEK NSDDLAGFKH LLGKYKLSFP AQEFELYCLI KEFESANIEV LPFTFNRFEN  120
ETHVDIEKDV RKALENAITV LKEKKNELI                                    149

SEQ ID NO: 13          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 13
MTIKLLDEFL KKHDLTRYQL SKLTGISQNT LKDQNEKPLN KYTVSILRSL SLISGLSVSD  60
VLFELEDIEK NSDDLAGFKH LLDKYKLSFP AQEFELYCLI KEFESANIEV LTFTFNRFEN  120
EEHADIEKDV KKALNNAIAV LKEKKEELL                                    149

SEQ ID NO: 14          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 14
MTIKLLDEFL KKHDLTRYQL SKLTGISQNT LKDQNEKSLN KYTVSILRSL SLISGLSVSD  60
VLFELEDIEK NSDDLAGFKH LLGKYKLSFP AQEFELYCLI KEFESANIEV LTFTFNRFEN  120
EEHADIEKDV KKALNNAIAV LKEKKEELL                                    149

SEQ ID NO: 15          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 15
MTIKLLDEFL KKHDLTRYQL SKLTGISQNT LKDQNEKSLN KYTVSILRSL SLISGLSVSD  60
VLFELEDIEK NSDDLAGFKH LLGKYKLSFP AQEFELYCLI KEFESANIEV LTFTFNRFEN  120
EEHADIEKDV KKALNNAIAV LKAKKEELL                                    149

SEQ ID NO: 16          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
```

```
                         organism = unidentified
SEQUENCE: 16
MTIKLLDEFL KKHDLTRYQL SKLTGISQNT LKDQNEKSLN KYTVSILRSL SLISGLSVSD  60
VLFELEDIEK NSDDLAGFKH LLGKYKLSFP AQEFELYCLI KEFESANIEV LTFTFNRFEN  120
EEHADIEKDV KKTLNNAIAV LKEKKEELL                                    149

SEQ ID NO: 17            moltype = AA  length = 144
FEATURE                  Location/Qualifiers
REGION                   1..144
                         note = Unknown bacterial, unknown viral (phage), or
                          syntheticCas9-inhibiting polypeptide
source                   1..144
                         mol_type = protein
                         organism = unidentified
SEQUENCE: 17
MTIKLLDEFL KKHDLTRYQL SKLTGISQNT LKDQNEKPLN KYTVSILRSL SLISGLSVSD  60
VLFELEDIEK NSDDLAGFKH LLDKYKLSFP AQEFELYCLI KEFESANIEV LTFTFNRFEN  120
EEHADIEKDV KKALNNAIAV LKEK                                         144

SEQ ID NO: 18            moltype = AA  length = 152
FEATURE                  Location/Qualifiers
REGION                   1..152
                         note = Unknown bacterial, unknown viral (phage), or
                          syntheticCas9-inhibiting polypeptide
source                   1..152
                         mol_type = protein
                         organism = unidentified
SEQUENCE: 18
MTIKLLDEFL KKHDLTRYQL SKLTGISQNT LKDQNEKSLN KYTVSILRSL SLISGLSVSD  60
VLFELEDIEK NSDDLAGFKH LLGKYKLSFP AQEFELYCLI KEFESANIEV LTFTFNRFEN  120
EEHADIEKDV KKALNNAIAV LKEKKKNCYK NY                                152

SEQ ID NO: 19            moltype = AA  length = 149
FEATURE                  Location/Qualifiers
REGION                   1..149
                         note = Unknown bacterial, unknown viral (phage), or
                          syntheticCas9-inhibiting polypeptide
source                   1..149
                         mol_type = protein
                         organism = unidentified
SEQUENCE: 19
MSIKLLDEFL KKHDLTRYQL SKLTGISQNT LKDQNEKSLN KYTVSILRAL ALITGMPISD  60
VLFELEDLEK NADDLAGFKH LLDTYKLSFP AQEFELYCLI KEFESANIEV LPFTFNRFES  120
ETHVDIEKDV RKALENAITV LKEKKNEFM                                    149

SEQ ID NO: 20            moltype = AA  length = 133
FEATURE                  Location/Qualifiers
REGION                   1..133
                         note = Unknown bacterial, unknown viral (phage), or
                          syntheticCas9-inhibiting polypeptide
source                   1..133
                         mol_type = protein
                         organism = unidentified
SEQUENCE: 20
MTIKLLDEFL KKHDLTRYQL SKLTGISQNT LKDQNEKPLN KYTVSILRSL SLISGLSVSD  60
VLFELEDIEK NSDDLAGFKH LLDKYKLSFP AQEFELYCLI KEFESANIEV LPFTFNRFEN  120
EEHVNIEKDV CKA                                                     133

SEQ ID NO: 21            moltype = AA  length = 149
FEATURE                  Location/Qualifiers
REGION                   1..149
                         note = Unknown bacterial, unknown viral (phage), or
                          syntheticCas9-inhibiting polypeptide
source                   1..149
                         mol_type = protein
                         organism = unidentified
SEQUENCE: 21
MSIKLLDEFL KKHDLTRYQL SKLTGISQNT LKDQNEKTLN KYTVSILRAL ALITGMPISD  60
VLFELEDLEK NADDLAGFKH LLDTYKLSFP AQEFELYCLI KEFESANIEV LPFTFNRFES  120
ETHVDIEKDV QKALENAITV LKEKKNEFM                                    149

SEQ ID NO: 22            moltype = AA  length = 149
FEATURE                  Location/Qualifiers
REGION                   1..149
                         note = Unknown bacterial, unknown viral (phage), or
                          syntheticCas9-inhibiting polypeptide
source                   1..149
                         mol_type = protein
                         organism = unidentified
```

```
SEQUENCE: 22
MSIKLLDEFL KKHDLTRYQL SKLTGISQNT LKDQNEKTLN KYTVSILRAL ALITGMPISD  60
VLFELEDLEK NADDLAGFKQ LLDTHKLSFP AHEFELYCLI KEFESVNIEV LPFTFNRFES  120
ETHVDIEKDV RKALENAITV LKEKKNEFM                                    149

SEQ ID NO: 23          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 23
MSIKLLDEFL KKHDLTRYQL SKLTGISQNT LKDQNEKTLN KYTVSILRAL ALITGMPISD  60
VLFELEDLEK NADDLAGFKQ LLDTHKLSFP AHEFELYCLI KEFESVNIEV LPFTFNRFES  120
ETHVDIEKDV RKALENAITV LKEKKNEFI                                    149

SEQ ID NO: 24          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 24
MSIKLLDEFL KKHDLTRYQL SKLTGISQNT LKDQNEKTLN KYTVSILRAL ALITGMPISD  60
VLFELEDLEK NADDLAGFKQ LLDTHKLSFP AHEFELYCLI KEFESVNIEV LPFTFNRFES  120
ETHVDIEKDV QKALENAIAV LKEKKEELL                                    149

SEQ ID NO: 25          moltype = AA  length = 125
FEATURE                Location/Qualifiers
REGION                 1..125
                       note = Unknown bacterial, unknown viral (phage), or
                        syntheticCas9-inhibiting polypeptide
source                 1..125
                       mol_type = protein
                       organism = unidentified
SEQUENCE: 25
MTIKLLDEFL KKHDLTRYQL SKLTGISQNT LKDQNEKPLN KYTVSILRSL SLISGLSVSD  60
VLFELEDIEK NSDDLAGFKH LLDKYKLSFP AQEFELYCLI KEFESANIEV LPFTFNRFEN  120
EEHVN                                                              125

SEQ ID NO: 26          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 26
MSIKLLDEFL KKHNKTRYQL SKLTGISQNT LNDYNKKELN KYSVSFLRAL SMCAGISTFD  60
VFIELAELEK SYDDLAGFKH LLDKYKLSFP AQEFELYCLI KEFESANIEV LPFTFNRFEN  120
EEHVNIKKDV CKALENAITV LKEKKNELL                                    149

SEQ ID NO: 27          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 27
MSIKLLDEFL KKHSKTRYQL SKLTGISQNT LNDYNKKELN KYSVSFLRAL SMCAGISTFD  60
VFIELAELEK SYDDLAGFKH LLDKYKLSFP AQEFELYCLI KEFESANIEV LPFTFNRFEN  120
EEHVNIKKDV CKALENAITV LKEKKNELL                                    149

SEQ ID NO: 28          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 28
```

```
MSIKLLDEFL KKHSKTRYQL SKLTGISQNT LNDYNKKELN KYSVSFLRAL SMCAGISTFD  60
VFIELAELEK SYDDLAGFKH LLDKYKLSFP AQEFELYCLI KEFESANIEV LPFTFNRFEN  120
EEHVNIEKDV CKALENAITV LKEKKNELL                                    149

SEQ ID NO: 29          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 29
MSIKLLDEFL KKHNKTRYQL SKLTGISQNT LNDYNKKELN KYSVSFLRAL SMCTGISTFD  60
VFIELAELEK SYDDLAGFKH LLNKYKLSFP AQEFELYCLI KEFDSANIEV LPFTFNRFEN  120
EEHVNIEKDV CKALENAITV LKEKKNELL                                    149

SEQ ID NO: 30          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 30
MSIKLLDEFL KKHSKTRYQL SKLTGISQNT LNDYNKKELN KYSVSFLRAL SMCAGISTFD  60
VFIELAELEK SYDDLAGFKH LLDKYKLSFP AQEFELYCLI KEFESANIEV LPFTFNRFEN  120
EEHVNIEKDV CKALENAITV LKEKKNELI                                    149

SEQ ID NO: 31          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 31
MNIKLLDEFL KKHNKTRYQL SKLTGISQNT LNDYNKKELN KYSVSFLRAL SMCTGISTFD  60
VFIELAELEK SHDDLAGFKH LLDKHKLSFP AQEFELYCLI KEFESANIEV LPFTFNRFEN  120
EEHVNIEKDV CKALENAITV LKEKKNELL                                    149

SEQ ID NO: 32          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 32
MSIKLLDEFL KKHDLTRYQL SKLTGISQNT LNDYNKKELN KYSVSFLRAL SMCTGISTFD  60
VLIELAELEK SYDDLAGFKH LLDKYKLSFP AQEFELYCLI KEFESANIEV LPFTFNRFEN  120
ETHVDIEKDV RKALENAITV LKEKKNELI                                    149

SEQ ID NO: 33          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 33
MTIKLLDEFL KKHSLTRYQL SKLTGISQNT LNDYNKKELN KYSVSFLRAL SMCAGISTFD  60
VLIELAELEK SYDDLAGFKH LLDKYKLSFP AQEFELYCLI KEFESANIEV LPFTFNRFEN  120
ETHVDIEKDV RKALENAITV LKEKKNELI                                    149

SEQ ID NO: 34          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 34
MSIKLLDEFL KKHNKTRYQL SKLTGISQNT LNDYNKKELN KYSVSFLRAL SMCAGISTFD  60
```

```
VLIELAELEK SYDDLAGFKH LLDKYKLSFP AQEFELYCLI KEFESANIEV LPFTFNRFEN  120
ETHVDIEKDV RKALENAITV LKEKKNELI                                    149

SEQ ID NO: 35          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 35
MSIKLLDEFL KKHNKTRYQL SKLTGISQNT LNDYNKKELN KYSVSFLRAL SMCAGISTFD  60
VLIELAELEK SYDDLAGFKH LLDKYKLSFP AQEFELYCLI KEFECANIEV LPFTFNRFEN  120
ETHVDIEKDV RKALENAITV LKEKKNELI                                    149

SEQ ID NO: 36          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 36
MSIKLLDEFL KKHNKTRYQL SKLTGISQNT LNDYNKKELN KYSVSFLRAL SMCAGISTFD  60
VFIELAELEK SYDDLAGFKH LLDKYKLSFP AQEFELYCLI KEFESANIEV LPFTFNRFEN  120
ETHVDIEKDV RKALENAITV LKEKKNELI                                    149

SEQ ID NO: 37          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 37
MSIKLLDEFL KKHNKTRYQL SKLTGISQNT LNDYNKKELN KYSVSFLRAL SMCTGISTFD  60
VFIELAELEK NYDDLAGFKH LLDKYKLSFP AQEFELYCLI KEFECANIEV LPFTFNRFEN  120
ETHVDIEKDV RKALENAITV LKEKKNELI                                    149

SEQ ID NO: 38          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 38
MSIKLLDEFL KKHNKTRYQL SKLTGISQNT LNDYNKKELN KYSVSFLRAL SMCAGISTFD  60
VFNELEELEK NYDDLAGFKH LLDKYKLSFS AQEFELYCLI KEFESANIEV LPFTFNRFEN  120
ETHVDIEKDV RKALENAITV LKEKKNELI                                    149

SEQ ID NO: 39          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 39
MTIKLLDEFL KKHSKTRYQL SKLTGISQNT LNDYNKKELN KYSVSFLRAL SMCAGISTFD  60
VFIELAELEK SYDDLAGFKH LLDKYKLSFP AQEFELYCLI KEFECANIEV LPFTFNRFEN  120
ETHVDIEKDV RKALENAITV LKEKKNELI                                    149

SEQ ID NO: 40          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 40
MSIKLLDEFL KKHSKTRYQL SKLTGISQNT LNDYNKKELN KYSVSFLRAL SMCAGISTFD  60
VFIELAELEK SYDDLAGFKH LLDKYKLSFP AQEFELYCLI KEFESANIEV LPFTFNRFEN  120
```

```
ETHVDIEKDV RKALENAITV LKEKKNELI                                  149

SEQ ID NO: 41          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 41
MSIKLLDEFL KKHSKTRYQL SKLTGISQNT LNDYNKKELN KYSVSFLRAL SMCAGISTFD  60
VFIELAELEK SYDDLAGFKH LLDKYKLSFP AQEFELYCLI KEFECANIEV LPFTFNRFEN  120
ETHVDIEKDV RKALENAITV LKEKKNELL                                  149

SEQ ID NO: 42          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 42
MTIKLLDEFL KKHDLTRYQL SKLTGISQNT LNDYNKKELN KYSVSFLRAL SMCTGISTFD  60
VFIELAELEK SYDDLAGFKH LLDKYKLSFP AQEFELYCLI KEFESANIEV LPFTFNRFEN  120
EEHTDIEKDV KKTLNNAIAV LKEKKEELL                                  149

SEQ ID NO: 43          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 43
MSIKLLDEFL KKHNKTRYQL SKLTGISQNT LNDYNKKELN KYSVSFLRAL SMCAGISTFD  60
VFIELAELEK SYDDLAGFKH LLDKYKLSFP AQEFELYCLI KEFECANIEV LPFTFNRFEN  120
ETHVDIEKDV RKALENAITV LKEKKNELI                                  149

SEQ ID NO: 44          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 44
MSIKLLDEFL KKHSKTRYQL SKLTGISQNT LNDYNKKELN KYSVSFMRAL SMCAGISTFD  60
VFIELAELEK SYDDLAGFKH LLDKYKLSFP AQEFELYCLI KEFESANIEV LPFTFNRFEN  120
ETHVDIEKDV RKALENAITV LKEKKNELI                                  149

SEQ ID NO: 45          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 45
MSIKLLDEFL KKHNKTRYQL SKLTGISQNT LNDYNKKELN KYSVSFLRAL SMCAGISTFD  60
VFKELEELEK NYDDLAGFKH LLDKYKLSFS AQEFELYCLI KEFESANIEV LPFTFNRFEN  120
ETHVDIEKDV RKALENAITV LKEKKNELI                                  149

SEQ ID NO: 46          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 46
MSIKLLDEFL KKHSKTRYQL SKLTGISQNT LNDYNKKELN KYSVSFLRAL SMCAGISTFD  60
VFIELAELEK SYDDLSGFKH LLDKYKLSFP AQEFELYCLI KEFESANIEV LPFTFNRFEN  120
ETHVDIEKDV RKALENAITV LKEKKNELI                                  149
```

```
SEQ ID NO: 47          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 47
MSIKLLDEFL KKHSKTRYQL SKLTGISQNT LNDYNKKELN KYSVSFLRAL SMCAGISTFD  60
VFIELAELEK SYDDLAGFKH LLDKYKLSFP AQEFELYCLI KEFESASIEV LPFTFNRFEN  120
ETHVDIEKDV RKALENAITV LKEKKNELI                                   149

SEQ ID NO: 48          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 48
MSIKLLDEFL KKHNKTRYQL SKLTGISQNT LNDYNKKELN KYSVSFLRAL SMCTGISTFD  60
VFIELAELEK SHDDLAGFKH LLDKHKLSFP AQEFELYCLI KEFESANIEV LPFTFNRFEN  120
ETHVDIEKDV RKALENAITV LKEKKNELI                                   149

SEQ ID NO: 49          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 49
MSIKLLDEFL KKHSKTRYQL SKLTGISQNT LNDYNKKELN KYSVSFLRAL SMCAGISTFD  60
VFIELAELEK SYDDLAGFKH LLDKYKLSFP AQEFELYCLI KEFECANIEV LPFTFNRFEN  120
ETHVDIEKDV RKALENAITV LKEKKNELI                                   149

SEQ ID NO: 50          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 50
MSIKLLDEFL KKHSKTRYQL SKLTGISQNT LNDYNKKELN KYSVSFLRAL SMCAGISTFD  60
VFIELAELEK SYDDLAGFKH LLDKYKLSFP AQEFELYCLI KEFECANIEV LPFTFNRFEN  120
ETHVDIEKDI RKALENAITV LKEKKNELI                                   149

SEQ ID NO: 51          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 51
MSIKLLDEFL KKHNKTRYQL SKLTGISQNT LNDYNKKELN KYTVSFLRTL SMCVGMSTVD  60
VFIELAELEK NYDDLAGFKH LLDKYKLSFP AQEFELYCLI KEFESANIEV LPFTFNRFES  120
ETHVDIEKDV KKALNNAIAV LKEKKEELL                                   149

SEQ ID NO: 52          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 52
MSIKLLDEFL KKHSKTRYQL SKLTGISQNT LNDYNKKELN KYSVSFLRAL SMCAGISTFD  60
VFIELAELEK SYDDLAGFKH LLDKYKLSFP AQEFELYCLI KEFESANIEV LPFTFNRFEN  120
ETHVDIEKDV RKALNNAIAV LKEKKEELL                                   149
```

```
SEQ ID NO: 53          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 53
MSIKLLDEFL KKHNKTRYQL SKLTGISQNT LNDYNKKELN KYSVSFLRAL SMCAGISTFD  60
VFIELAELEK SYDDLAGFKY LLDKHKLSFP AQEFELYCLI KEFESANIEV LPFTFNRFEN  120
ETHVDIEKDV RKALENAITV LKEKKNELI                                   149

SEQ ID NO: 54          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 54
MNIKLLDEFL KKHDLTRYQL SKLTGISQNT LNDYNKKELN KYSVSFLRAL SMCTGISTFD  60
VFIELAELEK SYDDLAGFKH LLDKHKLSFP AQEFELYCLI KEFESANIEV LPFTFNRFEN  120
EEHADIEKDV KKALNNAIAV LKAKKEELL                                   149

SEQ ID NO: 55          moltype = AA  length = 130
FEATURE                Location/Qualifiers
REGION                 1..130
                       note = Unknown bacterial, unknown viral (phage), or
                        syntheticCas9-inhibiting polypeptide
source                 1..130
                       mol_type = protein
                       organism = unidentified
SEQUENCE: 55
MSIKLLDEFL KKHDLTRYQL SKLTGISQNT LKDQNEKTLN KYTVSILRAL ALITGMPISD  60
VLFELEDLEK NADDLAGFKQ LLDTHKLSFP AHEFELYCLI KEFESVNIEV LPFTFNRFES  120
ETHVDIEKDV                                                        130

SEQ ID NO: 56          moltype = AA  length = 134
FEATURE                Location/Qualifiers
REGION                 1..134
                       note = Unknown bacterial, unknown viral (phage), or
                        syntheticCas9-inhibiting polypeptide
source                 1..134
                       mol_type = protein
                       organism = unidentified
SEQUENCE: 56
TRYQLSKLTG ISQNTLNDYN KKELNKYSVS FLRALSMCAG ISTFDVFIEL AELEKSYDDL  60
AGFKHLLDKY KLSFPAQEFE LYCLIKEFES ANIEVLPFTF NRFENEEHVN IKKDVCKALE  120
NAITVLKEKK NELL                                                   134

SEQ ID NO: 57          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 57
MKINLLDEFL KRHNITRYRL SKLAGISQNT LKDYNEKSLN KYTVSFLRSL SFVTGEDVTD  60
VLIELAELEK GYDDLAGFKY LLDKYKLSFP ALEFELYCII KEFESANIEI SPFTFNRFEN  120
ETHVDIEKDV KKALQNAVTV LEERKEELL                                   149

SEQ ID NO: 58          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 58
MKNNLLDTFL KRHDITRYRL SKLAGISQNT LKDYNEKSLN KYTVSLLRSL SFVTGESITD  60
VLLELAEIEK DYDDLAGFKY LLDKYKLSFP ALEFELYCII KEFESANVEI SPFTFNRFEN  120
ETHADIEKDV KKALNNAITV LKEKKEELL                                   149

SEQ ID NO: 59          moltype = AA  length = 149
```

```
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 59
MSIKLLDEFL KKHNKTRYQL SKLTGISQNT LNDYNKKELN KYSVSFLRAL SMCAGISTFD  60
VFIELAELEK SYDDLAGFKY LLDKHKLSFP TQEFELYCLI KEFESANIEV LPFTFNRFEN  120
ETHADIEKDV KKALNNAIAV LEEKKEELL                                   149

SEQ ID NO: 60          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 60
MKINLLDAFL KRHNITRYRL SKLAGISQNT LKDYNEKSLN KYTVSFLRSL SFVTGEDVTD  60
VLIELAELEK GYDDLAGFKY LLDKYKLAFP ALEFELYCLI KEFEAANIEV SPFTFNRFEN  120
ETHADIEKDV KKALKNAIIV LKEKKEELL                                   149

SEQ ID NO: 61          moltype = AA  length = 133
FEATURE                Location/Qualifiers
REGION                 1..133
                       note = Unknown bacterial, unknown viral (phage), or
                        syntheticCas9-inhibiting polypeptide
source                 1..133
                       mol_type = protein
                       organism = unidentified
SEQUENCE: 61
MSIKLLDEFL KKHSKTRYQL SKLTGISQNT LNDYNKKELN KYSVSFLRAL SMCAGISTFD  60
VFIELAELEK SYDDLAGFKH LLDKYKLSFP AQEFELYCLI KEFESANIEV LPFTFNRFEN  120
EEHVNIEKDV CKA                                                    133

SEQ ID NO: 62          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 62
MKINLLDEFL KRHNITRYRL SKLAGISQNT LKDYTEKSLN KYTVSFLRSL SFATGESVTD  60
ILLELAELEK DYDDLAGFKY LLDKYKLAFP ALEFELYCLI KEFESANIEI SPFTFNRFES  120
ETHTDIEKDV KKALQNAVTV LEERKEELL                                   149

SEQ ID NO: 63          moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 63
MSIKLLDEFL KKHSKTRYQL SKLTGISQNT LNDYNKKELN KYSVSFLRSL SFATGESVTD  60
ILLELAELEK DYDDLAGFKY LLDKYKLAFP ALEFELYCLI KEFESANIEI SPFTFNRFES  120
ETHTDIEKDV KKALQNAVTV LEERKEELL                                   149

SEQ ID NO: 64          moltype = AA  length = 159
FEATURE                Location/Qualifiers
REGION                 1..159
                       note = Unknown bacterial, unknown viral (phage), or
                        syntheticCas9-inhibiting polypeptide
source                 1..159
                       mol_type = protein
                       organism = unidentified
SEQUENCE: 64
MSIKLLDEFL KKHNKTRYQL SKLTGISQNT LNDYNKKELN KYSVSFLRAL SMCAGISTFD  60
VFIELAELEK SYDDLAGFKY LLDKHKLSFP TQEFELYCLI KEFESANIEV LPFTFNRFEN  120
ETHADIEKDV KKALNNAIAV LEEKKRRTVI KTIDYYDYS                        159

SEQ ID NO: 65          moltype = AA  length = 148
FEATURE                Location/Qualifiers
```

```
REGION                  1..148
                        note = Unknown bacterial, unknown viral (phage), or
                         syntheticCas9-inhibiting polypeptide
source                  1..148
                        mol_type = protein
                        organism = unidentified
SEQUENCE: 65
MNNFAFITSF NYQQPRYQLS KLTGISQNTL NDYNKKELNK YSVSFLRALS MCAGISTFDV  60
LIELAELEKS YDDLAGFKHL LDKYKLSFPA QEFELYCLIK EFESANIEVL PFTFNRFENE  120
THVDIEKDVR KALENAITVL KEKKNELI                                    148

SEQ ID NO: 66           moltype = AA  length = 149
FEATURE                 Location/Qualifiers
REGION                  1..149
                        note = Unknown bacterial, unknown viral (phage), or
                         syntheticCas9-inhibiting polypeptide
source                  1..149
                        mol_type = protein
                        organism = unidentified
SEQUENCE: 66
MKTNLLDTFL KRHGITRYRL SKLAGISQNT LKDYTEKSLN KYTVSFLRSL SFVTGEDVTD  60
VLLELAEIEN GYDDLAGFKY LLDKYKLSFP ALEFELYCII KEFESANIEI SPFTFNRFEN  120
ETHADIEKDV KKALKNAVTV LEERKEELL                                   149

SEQ ID NO: 67           moltype = AA  length = 148
FEATURE                 Location/Qualifiers
REGION                  1..148
                        note = Unknown bacterial, unknown viral (phage), or
                         syntheticCas9-inhibiting polypeptide
source                  1..148
                        mol_type = protein
                        organism = unidentified
SEQUENCE: 67
MNNFAFITSF NYQQPRYQLS KLTGISQNTL NDYNKKELNK YSVSFLRALS MCAGISTFDV  60
LIELAELEKS YDDLAGFKHL LDKYKLSFPA QEFELYCLIK EFECANIEVL PFTFNRFENE  120
THVDIEKDVR KALENAITVL KEKKNELI                                    148

SEQ ID NO: 68           moltype = AA  length = 125
FEATURE                 Location/Qualifiers
REGION                  1..125
                        note = Unknown bacterial, unknown viral (phage), or
                         syntheticCas9-inhibiting polypeptide
source                  1..125
                        mol_type = protein
                        organism = unidentified
SEQUENCE: 68
MSIKLLDEFL KKHNKTRYQL SKLTGISQNT LNDYNKKELN KYSVSFLRAL SMCAGISTFD  60
VFIELAELEK SYDDLAGFKH LLDKYKLSFP AQEFELYCLI KEFESANIEV LPFTFNRFEN  120
EEHVN                                                             125

SEQ ID NO: 69           moltype = AA  length = 123
FEATURE                 Location/Qualifiers
REGION                  1..123
                        note = Unknown bacterial, unknown viral (phage), or
                         syntheticCas9-inhibiting polypeptide
source                  1..123
                        mol_type = protein
                        organism = unidentified
SEQUENCE: 69
MTLTRAQKKY AEAMHEFINM VDDFEESTPD FAKEVLHDSD YVVITKNEKY AVALCSLSTD  60
ECEYDTNLYL DEKLVDYSTV DVNGVTYYIN IVETNDIDDL EIATDEDEMK SGNQEIILKS  120
ELK                                                               123

SEQ ID NO: 70           moltype = AA  length = 123
FEATURE                 Location/Qualifiers
REGION                  1..123
                        note = Unknown bacterial, unknown viral (phage), or
                         syntheticCas9-inhibiting polypeptide
source                  1..123
                        mol_type = protein
                        organism = unidentified
SEQUENCE: 70
MTLTRAQKKY AEAMHEFINM VDDFEESTPD FAKEVLHDSD YVVITKNEKY AVALCSLSTD  60
ECEYDTNLYL DEKLVDYSTV DVNGVTYYIN IVETNDIDDL EIATDEDEMK SGNQEIILKS  120
ELN                                                               123

SEQ ID NO: 71           moltype = AA  length = 123
FEATURE                 Location/Qualifiers
REGION                  1..123
```

```
                         note = Unknown bacterial, unknown viral (phage), or
                          syntheticCas9-inhibiting polypeptide
source                   1..123
                         mol_type = protein
                         organism = unidentified
SEQUENCE: 71
MTITRAQKKY AEAMHEFINM VDDFEESTPD FAKEVLHDSD YVVITKNEKY AVALCSLSTD  60
ECEYDTNLYL DEKLVDYSTV DVNGVTYYIN IVETNDIDDL EIATDEDEMK SGNQEIILKS  120
ELK                                                               123

SEQ ID NO: 72            moltype = AA  length = 124
FEATURE                  Location/Qualifiers
REGION                   1..124
                         note = Unknown bacterial, unknown viral (phage), or
                          syntheticCas9-inhibiting polypeptide
source                   1..124
                         mol_type = protein
                         organism = unidentified
SEQUENCE: 72
KMTLTRAQKK YAEAMHEFIN MVDDFEESTP DFAKEVLHDS DYVVITKNEK YAVALCSLST  60
DECEYDTNLY LDEKLVDYST VDVNGVTYYI NIVETNDIDD LEIATDEDEM KSGNQEIILK  120
SELN                                                              124

SEQ ID NO: 73            moltype = AA  length = 122
FEATURE                  Location/Qualifiers
REGION                   1..122
                         note = Unknown bacterial, unknown viral (phage), or
                          syntheticCas9-inhibiting polypeptide
source                   1..122
                         mol_type = protein
                         organism = unidentified
SEQUENCE: 73
MTLTRAQKKY AEAMHEFINM VDDFEESTPD FAKEVLHDSD YVVITKNEKY AVALCSLSTD  60
ECEYDTNLYL DEKLVDYSTV DVNGVTYYIN IVETNDIDDL EIATDEDEMK SGNQEIILKS  120
EL                                                                122

SEQ ID NO: 74            moltype = AA  length = 123
FEATURE                  Location/Qualifiers
REGION                   1..123
                         note = Unknown bacterial, unknown viral (phage), or
                          syntheticCas9-inhibiting polypeptide
source                   1..123
                         mol_type = protein
                         organism = unidentified
SEQUENCE: 74
MTLTRAQKKY AEAMHEFINM VDDFEESTPD FAKEVLHDSD YVVITKNEKY AVALCSLSTD  60
ECEYDTNLYL DEKLVDYSTV DVNGVTYYIN IVETNDIDDL EIATDEDEMK SDNQEIILKS  120
ELK                                                               123

SEQ ID NO: 75            moltype = AA  length = 123
FEATURE                  Location/Qualifiers
REGION                   1..123
                         note = Unknown bacterial, unknown viral (phage), or
                          syntheticCas9-inhibiting polypeptide
source                   1..123
                         mol_type = protein
                         organism = unidentified
SEQUENCE: 75
MTITRAQKKY AEAMHEFINM VDDFEESTPD FAKEVLHDSD YVVITKNEKY AVALCSLSTD  60
GCEYDTNLYL DEKLVDYSTV DVNGVTYYIN IVETNDIDDL EIATDEDEMK SGNQEIILKS  120
ELK                                                               123

SEQ ID NO: 76            moltype = AA  length = 123
FEATURE                  Location/Qualifiers
REGION                   1..123
                         note = Unknown bacterial, unknown viral (phage), or
                          syntheticCas9-inhibiting polypeptide
source                   1..123
                         mol_type = protein
                         organism = unidentified
SEQUENCE: 76
MTLTRAQKKY AEAMHEFINM VDDFEESTPD FAKEVLHDSD YVVITKNEKY AVALCSLSTD  60
ECEYDTNLYL DEKLVDYSTV DVNGVTYYIN IVETKDIDDL EIATDEDEMK SDNQEIILKS  120
ELK                                                               123

SEQ ID NO: 77            moltype = AA  length = 123
FEATURE                  Location/Qualifiers
REGION                   1..123
                         note = Unknown bacterial, unknown viral (phage), or
```

```
                         syntheticCas9-inhibiting polypeptide
source                  1..123
                        mol_type = protein
                        organism = unidentified
SEQUENCE: 77
MTITTAQKKY AEAMHEFINM VDDFEESTPD FAKEVLHDSD YVVITKNEKY AVALCSLSTD  60
ECEYDTNLYL DEKLVDYSTV DVNGVTYYIN IVETNDIDDL EIATDEDEMK SGNQEIILKS  120
ELK                                                               123

SEQ ID NO: 78           moltype = AA  length = 123
FEATURE                 Location/Qualifiers
REGION                  1..123
                        note = Unknown bacterial, unknown viral (phage), or
                         syntheticCas9-inhibiting polypeptide
source                  1..123
                        mol_type = protein
                        organism = unidentified
SEQUENCE: 78
MTITTAQRKY NEAMHEFINM VDDFEESTPD FAKEVLHDSD YVVITKNEKY AVALCSLSTD  60
ECEYDTNLYL DEKLVDYSTV DVNGVTYYIN IVETNDIDDL EIATDEDEMK SGNQEIILKS  120
ELK                                                               123

SEQ ID NO: 79           moltype = AA  length = 123
FEATURE                 Location/Qualifiers
REGION                  1..123
                        note = Unknown bacterial, unknown viral (phage), or
                         syntheticCas9-inhibiting polypeptide
source                  1..123
                        mol_type = protein
                        organism = unidentified
SEQUENCE: 79
MTITTAQRKY NEAMHEFINM VDDFEESTPD FAKEVLHDCD YVVVTKNEKY AVALCTLSTD  60
ECEYDTNLYL DEKLVDYSTV NVNGVTYYIN IVETNDIDDL EIATDEDEMK SDNQEIILKS  120
ELK                                                               123

SEQ ID NO: 80           moltype = AA  length = 123
FEATURE                 Location/Qualifiers
REGION                  1..123
                        note = Unknown bacterial, unknown viral (phage), or
                         syntheticCas9-inhibiting polypeptide
source                  1..123
                        mol_type = protein
                        organism = unidentified
SEQUENCE: 80
MTITTAQRKY NEAMHEFINM VDDFEESTPD FAKEVLHDCD YVVVTKNEKY AVALCTLSTD  60
ECEYDTNLYL DEKLVDYSTV NVNGVTYYIN IVETNDIDDL EIATDEDEMK SDNQKIILKS  120
ELK                                                               123

SEQ ID NO: 81           moltype = AA  length = 123
FEATURE                 Location/Qualifiers
REGION                  1..123
                        note = Unknown bacterial, unknown viral (phage), or
                         syntheticCas9-inhibiting polypeptide
source                  1..123
                        mol_type = protein
                        organism = unidentified
SEQUENCE: 81
MTLTRAQKKY AEAMHEFINM VDDFEESTPD FAKEVLHDSD YVVITKNEKY AVALCSLSTD  60
ECEYDTNLYL DEKLVDYSTV DVNGVTYYIN IVETKDIDDL EIATDEDKEK HDKQEVIIKS  120
ELN                                                               123

SEQ ID NO: 82           moltype = AA  length = 110
FEATURE                 Location/Qualifiers
REGION                  1..110
                        note = Unknown bacterial, unknown viral (phage), or
                         syntheticCas9-inhibiting polypeptide
source                  1..110
                        mol_type = protein
                        organism = unidentified
SEQUENCE: 82
MHEFINMVDD FEESTPDFAK EVLHDSDYVV ITKNEKYAVA LCSLSTDECE YDTNLYLDEK  60
LVDYSTVDVN GVTYYINIVE TNDIDDLEIA TDEDEMKSGN QEIILKSELK            110

SEQ ID NO: 83           moltype = AA  length = 122
FEATURE                 Location/Qualifiers
REGION                  1..122
                        note = Unknown bacterial, unknown viral (phage), or
                         syntheticCas9-inhibiting polypeptide
source                  1..122
```

```
                        mol_type = protein
                        organism = unidentified
SEQUENCE: 83
MTLTRAQKKY AEAMHEFINM VDDFEESKPN FAKEVLHDSD YVVITKNEKY AVALCSLSTD  60
ECEYDTNLYL DEKLVDYSTV DVNGVTYYIN IVVTNEDDFK LATDKDKEKH DKQEVIVKSE  120
LN                                                                122

SEQ ID NO: 84           moltype = AA  length = 122
FEATURE                 Location/Qualifiers
REGION                  1..122
                        note = Unknown bacterial, unknown viral (phage), or
                         syntheticCas9-inhibiting polypeptide
source                  1..122
                        mol_type = protein
                        organism = unidentified
SEQUENCE: 84
MTLTTAQRKY NEAMHEFINM VDDFEESTPE FSKEVLNDSD YVVITKNEKY AGALCHVSTD  60
ECEDGSNLYI DEKLIDYSTL NVGGVTYYIN IVERCEDDLE IATDEDKMKS DNQEIILKNE  120
LN                                                                122

SEQ ID NO: 85           moltype = AA  length = 103
FEATURE                 Location/Qualifiers
REGION                  1..103
                        note = Unknown bacterial, unknown viral (phage), or
                         syntheticCas9-inhibiting polypeptide
source                  1..103
                        mol_type = protein
                        organism = unidentified
SEQUENCE: 85
MVDDFEESTP EFSKEVLNDS DYVVITKNEK YAGALCHVST DECEDGSNLY IDEKLIDYST  60
LNVGGVTYYI NIVERCEDDL EIATDEDKMK SDNQEIILKN ELN                   103

SEQ ID NO: 86           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 86
MTLTTAQKRY YDAMNEFEAI TSKKLEQTPE FSQDLLNDSD YLVITKNEAY AVALCMLDDD  60
KLYLDETLVQ STCLDVEGET YYINFVVTNE DDFKLATDED KEKHDKQEVI VKSELN      116

SEQ ID NO: 87           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 87
MTLTTAQKRY YDAMNEFEAI TSKELEQTPE FSQDLLNDSD YLVITKNEAY AVALCMLDDD  60
KLYLDETLVQ STCLDVEGET YYINFVVTNE DDFKLATDED KEKHDKQEVI VKSELN      116

SEQ ID NO: 88           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 88
MTLTTAQKRY YDAMNEFEAI TSKELEQTPE FSQDLLNDSD YLVITKNEAY AVALCMLDDD  60
KLYLDETLVQ STCLDVEGET YYINFVVTNE DDFKLATDKD KEKHDKQEVI VKSELN      116

SEQ ID NO: 89           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 89
MTITTAQKRY YDAMNEFEAI ISKELEQTPA FSQDLLNDSD YLVITKNEAY AVALCMLDDD  60
KLYLDETLVQ STRLDIEDET YYINFVVTNE DDFKLATDED KEKHDKQEVI IKSELN      116
```

```
SEQ ID NO: 90           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 90
MTITTAQKRY YDAMNEFEAI TSKELEQTPE FSQDLLNDSD YLVITKNEAY AVALCMLDDD  60
KLYIDETLVQ STCLDVEGET YYINFVVTNE DDFKLATDKD KEKHDKQEVI IKSELN      116

SEQ ID NO: 91           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 91
MTLTTAQKRY YDAMNEFEAI ISKELEQTRA FSQDLLNDSD YLVITKNEAY AVDLCMLDDD  60
KLYLDETLVQ STRLDIEDET YYINFVVTNE DDFKLATDED KEKHDRQEVI IKSELN      116

SEQ ID NO: 92           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 92
MTITTAQKRY YDAMNEFEAI TSKELEQTPE FSQDLLNDSD YLVVTKNEAY AAALCMLDDD  60
KLYLDETLVQ STCLDVEGEI YYINFVVTNE DDFKLATDKD KEKHDKQEVI VKSELN      116

SEQ ID NO: 93           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 93
MTITTAQKRY YDAMNEFEAI TSKGLEQTPE FSQDLLNDFD YLVITKNEAY AAALCMLDDE  60
KLYLDETLVH STRLDIEDDT YYINFVVTNE DDFKLATDED KEKHDKQEVI IKRELN      116

SEQ ID NO: 94           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 94
MTITTAQKRY YDAMNEFEAI ISKELEQTPA FSQDLLNDSD YLVITKNEAY AVALCLLDDD  60
KLYLDETLVH STRLDIEDET YYINFVVTNE DDFKLATDED KEKHDKQEVI IKSELN      116

SEQ ID NO: 95           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 95
MTITTAQKRY YDAMNEFEAI ISKELEQTPA FSQNLLNDSD YLVITKNEAY AVALCLLDDD  60
KLYLDETLVH STRLDIEDET YYINFVVTNE DDFKLATDED KEKHDKQEVI IKSELN      116

SEQ ID NO: 96           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
```

```
                        mol_type = protein
                        organism = unidentified
SEQUENCE: 96
MTITTAQKRY YDAMNEFEAI TSKELEQTPA FSQDLLNDSD YLVITKNEAY AVALCLLDDD  60
KLYLDETLVH STRLDIEDET YYINFVVTNE DDFKLATDED KEKHDKQEVI VKSELN      116

SEQ ID NO: 97           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 97
MTITTAQKRY YDAMNEFEAI ISKELEQTPA FSQDLLNDSD YLVITKNEAY AVALCLLDDD  60
KLYLDETLVH STRLNIEDET YYINFVVTNE DDFKLATDED KEKHDKQEVI IKSEFN      116

SEQ ID NO: 98           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 98
MTLTTAQKRY YDAMNEFEAI TSKELEQTPE FSQDLLNDSD YLAVTKNEAY AVALCLLDDD  60
KLYLDETLVH STRLDIEDET YYINFVVTNE DDFKLATDED KEKHDKQEVI IKSGLN      116

SEQ ID NO: 99           moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 99
MTVTTAQKRY YDAMNEFEAI TSKELEQTPE FSQDLLNDSD YLAVTKNEAY AVALCLLDDD  60
KLYLDETLVH STRLDIEDET YYINFVVTNE DDFKLATDED KEKHDKQEVI IKSELN      116

SEQ ID NO: 100          moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 100
MTLTTVQKRY YDAMNEFEAI TSKELEQTPE FSQDLLNDSD YLAVTKNEAY AVALCLLDDD  60
KLYLDETLVH STRFDIEDET YYINFVVTNE DDFKLATDED KEKHDKQEVI IKSELN      116

SEQ ID NO: 101          moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 101
MTLTTVQKRY YDAMNEFEAI TSKELEQTPE FSQDSLNDSD YLAVTKNEAY AVALCLLDDD  60
KLYLDETLVH STRFDIEDET YYINFVVTNE DDFKLATDED KEKHDKQEVI IKSELN      116

SEQ ID NO: 102          moltype = AA  length = 116
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 102
MTITTAQKRY YDAMNEFEAI ISKELEQTPA FSQDLLNDSD YLAVTKNEAY AVALCLLDDD  60
KLYLDETLVH STRLDIEDET YYINFVVTNE DDFKLATDED KEKHDKQEVI IKSGLN      116

SEQ ID NO: 103          moltype = AA  length = 116
```

```
FEATURE                 Location/Qualifiers
REGION                  1..116
                        note = Unknown bacterial, unknown viral (phage), or
                         syntheticCas9-inhibiting polypeptide
source                  1..116
                        mol_type = protein
                        organism = unidentified
SEQUENCE: 103
MTITTAQKRY YDAMNEFEAI TSKELEQTPA FSQDLLNDSD YLAVTKNEAY AVALCLLDDD  60
KLYLDETLVH STRLDIEDET YYINFVVTNE DDFKLATDED KEKHDKQEVI IKSGLN      116

SEQ ID NO: 104          moltype = AA  length = 130
FEATURE                 Location/Qualifiers
REGION                  1..130
                        note = Unknown bacterial, unknown viral (phage), or
                         syntheticCas9-inhibiting polypeptide
source                  1..130
                        mol_type = protein
                        organism = unidentified
SEQUENCE: 104
MAITLSQRKF YEAINEFEEM TENEVVTSPR IPQDYLNDGD YVVITKSENY ALNLCTTNLE  60
GFEDRHFLDE KLIYSTFVET YSGETYYIYI TQTAEFDEDD AVEFLATQEQ IYEYHKQEEQ  120
KTVILKMELS                                                         130

SEQ ID NO: 105          moltype = AA  length = 130
FEATURE                 Location/Qualifiers
REGION                  1..130
                        note = Unknown bacterial, unknown viral (phage), or
                         syntheticCas9-inhibiting polypeptide
source                  1..130
                        mol_type = protein
                        organism = unidentified
SEQUENCE: 105
MAQTEAQKIF YEAINEFEEM TNEEVVTSPR IPQDYLNDGD YVVITKSENY ALNLCTTDLE  60
GFEDRYFLDE KLIYSTSVET YTDETYYIYI TQTTEFEEDN AVEFLATQEQ IYEYHKQEEQ  120
KTVILKMELS                                                         130

SEQ ID NO: 106          moltype = AA  length = 130
FEATURE                 Location/Qualifiers
REGION                  1..130
                        note = Unknown bacterial, unknown viral (phage), or
                         syntheticCas9-inhibiting polypeptide
source                  1..130
                        mol_type = protein
                        organism = unidentified
SEQUENCE: 106
MTTARKKFYQ AISEFEAMTG KDVERTPQIA DEVLNDAEYI AFTKTEKYAL YLCTSNVEGL  60
EDRYFLDEEC LDSTFLETED NETYYIHFLQ ETEFSEDDNE DELPLATEEQ IEAYDKQEEL  120
KAVILKKELN                                                         130

SEQ ID NO: 107          moltype = AA  length = 129
FEATURE                 Location/Qualifiers
REGION                  1..129
                        note = Unknown bacterial, unknown viral (phage), or
                         syntheticCas9-inhibiting polypeptide
source                  1..129
                        mol_type = protein
                        organism = unidentified
SEQUENCE: 107
MRTTAQERLD NAINEFEEIT NEEVVTSPRI PQDYLNDGDY VVITKSENYA LNLCTTNLEG  60
FEDRHFLDEK LIYSTFVETY SGETYYIYIT QTAEFDEDDA VEFLATQEQI YEYHKQEEQK  120
TVILKMELS                                                          129

SEQ ID NO: 108          moltype = AA  length = 129
FEATURE                 Location/Qualifiers
REGION                  1..129
                        note = Unknown bacterial, unknown viral (phage), or
                         syntheticCas9-inhibiting polypeptide
source                  1..129
                        mol_type = protein
                        organism = unidentified
SEQUENCE: 108
MRTTAQERLD NAINEFEEIT NEEVVTSPRI PQDYLNDGDY VVITKSENYA LNLCTTNLEG  60
FEDRHFLDEK LIYSTFVETY AGETYYIYIT QTAEFDEDDA VEFLATQEQI YEYHKQEEQK  120
TVILKMELS                                                          129

SEQ ID NO: 109          moltype = AA  length = 129
FEATURE                 Location/Qualifiers
REGION                  1..129
```

```
                        note = Unknown bacterial, unknown viral (phage), or
                         syntheticCas9-inhibiting polypeptide
source                  1..129
                        mol_type = protein
                        organism = unidentified
SEQUENCE: 109
MRTTAQERLD NAINEFEEIT NEEVVTSPLI PQDYLNDGDY VVITKSENYA LNLCTTNLEG  60
FEDRHFLDEK LIYSTFVETY SGETYYIYIT QTAEFDEDDA VEFLATQEQI YEYHKQEEQK  120
TVILKMELS                                                         129

SEQ ID NO: 110          moltype = AA  length = 125
FEATURE                 Location/Qualifiers
REGION                  1..125
                        note = Unknown bacterial, unknown viral (phage), or
                         syntheticCas9-inhibiting polypeptide
source                  1..125
                        mol_type = protein
                        organism = unidentified
SEQUENCE: 110
MFNKAEIMKQ AWNWFNDSNI WLSDIEWVSY TDKEKSFSVC LKAAWSKAKE EVEESKKESK  60
HIAKSEELKA WNWAERKLGL HFNISDDEKF TSVKDETKIN FGLSVWACAM KAVKLHNDLF  120
PQTAA                                                             125

SEQ ID NO: 111          moltype = AA  length = 125
FEATURE                 Location/Qualifiers
REGION                  1..125
                        note = Unknown bacterial, unknown viral (phage), or
                         syntheticCas9-inhibiting polypeptide
source                  1..125
                        mol_type = protein
                        organism = unidentified
SEQUENCE: 111
MYNKAEIMKQ AWNWFNDSNI WLSDIEWVSY TDKEKSFSVC LKAAWSKAKE EVEESKKESK  60
HIAKSEELKA WNWAERKLGL HFNISDDEKF TSVKDETKIN FGLSVWACAM KAVKLHNDLF  120
PQTAA                                                             125

SEQ ID NO: 112          moltype = AA  length = 125
FEATURE                 Location/Qualifiers
REGION                  1..125
                        note = Unknown bacterial, unknown viral (phage), or
                         syntheticCas9-inhibiting polypeptide
source                  1..125
                        mol_type = protein
                        organism = unidentified
SEQUENCE: 112
MYNKAEIMKQ AWNWFNDSNI WLSDIEWVSY TDKEKSFSVC LKGAWSKAKE EVEESKKESK  60
HIAKSEELKA WNWAERKLGL HFNISDDEKF TSVKDETKIN FGLSVWACAM KAVKLHNDLF  120
PQTAA                                                             125

SEQ ID NO: 113          moltype = AA  length = 125
FEATURE                 Location/Qualifiers
REGION                  1..125
                        note = Unknown bacterial, unknown viral (phage), or
                         syntheticCas9-inhibiting polypeptide
source                  1..125
                        mol_type = protein
                        organism = unidentified
SEQUENCE: 113
MYNKAEIMKQ AWNWFNDSNI WLSDIEWVSY TDKEKSFSVC LKAAWSKAKE EVEESKKESK  60
HIAKSEELKA WNWAERKLGL HFNISDDEKF TSVKDETKIN FGLSLWACAM KAVKLHNDLF  120
PQTAA                                                             125

SEQ ID NO: 114          moltype = AA  length = 125
FEATURE                 Location/Qualifiers
REGION                  1..125
                        note = Unknown bacterial, unknown viral (phage), or
                         syntheticCas9-inhibiting polypeptide
source                  1..125
                        mol_type = protein
                        organism = unidentified
SEQUENCE: 114
MYNKAEIMKQ AWNWFNDSNV WLSDIEWISY TDKEKTFSVC LKAAWSKAKE EVEESKKESK  60
HIAKSEELKA WNWAERKLGL HFNISDDEKF TSVKDETKIN FGLSVWACAM KAVKLHNDLF  120
PQTAA                                                             125

SEQ ID NO: 115          moltype = AA  length = 125
FEATURE                 Location/Qualifiers
REGION                  1..125
                        note = Unknown bacterial, unknown viral (phage), or
```

```
                        syntheticCas9-inhibiting polypeptide
source                 1..125
                       mol_type = protein
                       organism = unidentified
SEQUENCE: 115
MYNKAEIMKQ AWNWFNDSNI WLSDIEWVSY TDKEKSFSVC LKAAWSKAKE EVEESKKESK  60
YIAKSEELKA WNWAERKLGL RFNISDDEKF TSVKDETKIN FGLSVWACAM KAVKLHNDLF  120
PQTAA                                                              125

SEQ ID NO: 116         moltype = AA  length = 125
FEATURE                Location/Qualifiers
REGION                 1..125
                       note = Unknown bacterial, unknown viral (phage), or
                        syntheticCas9-inhibiting polypeptide
source                 1..125
                       mol_type = protein
                       organism = unidentified
SEQUENCE: 116
MFNKAEIMKQ AWNWFTDSNV WLSDIEWASY TDKEKSFSVC LKAAWSKAKE EVEESKKESK  60
HIAKSEELKA WNWAERKLGL HFNISDDEKF TSVKDETKIN FGLSVWACAM KAVKLHNDLF  120
PQTAA                                                              125

SEQ ID NO: 117         moltype = AA  length = 125
FEATURE                Location/Qualifiers
REGION                 1..125
                       note = Unknown bacterial, unknown viral (phage), or
                        syntheticCas9-inhibiting polypeptide
source                 1..125
                       mol_type = protein
                       organism = unidentified
SEQUENCE: 117
MYNKAEIMKQ AWNWFNDSNI WLSDIEWVSY TDKEKSFSVC LKAAWSKAKE EVEEFKKESK  60
YIAKSEELKA WNWAERKLGL RFNISDDEKF TSVKDETKIN FGLSVWACAM KAVKLHNDLF  120
PQTAA                                                              125

SEQ ID NO: 118         moltype = AA  length = 118
FEATURE                Location/Qualifiers
REGION                 1..118
                       note = Unknown bacterial, unknown viral (phage), or
                        syntheticCas9-inhibiting polypeptide
source                 1..118
                       mol_type = protein
                       organism = unidentified
SEQUENCE: 118
MKQAWNWFND SNIWLSDIEW VSYTDKEKSF SVCLKAAWSK AKEEVEESKK ESKYIAKSEE  60
LKAWNWAERK LGLRFNISDD EKFTSVKDET KINFGLSVWA CAMKAVKLHN DLFPQTAA    118

SEQ ID NO: 119         moltype = AA  length = 125
FEATURE                Location/Qualifiers
REGION                 1..125
                       note = Unknown bacterial, unknown viral (phage), or
                        syntheticCas9-inhibiting polypeptide
source                 1..125
                       mol_type = protein
                       organism = unidentified
SEQUENCE: 119
MYNKAEIMKQ AWNWFNNSNV WLSDIEWVSY TDKEKTFSVC LKAAWSKAKE EVEESKEESK  60
HIAKSEELKA WNWAERKLGL HFNISDDEKF TSVKDETKIN FGLSVWACAM KAVKLHNDLF  120
PQTAA                                                              125

SEQ ID NO: 120         moltype = AA  length = 125
FEATURE                Location/Qualifiers
REGION                 1..125
                       note = Unknown bacterial, unknown viral (phage), or
                        syntheticCas9-inhibiting polypeptide
source                 1..125
                       mol_type = protein
                       organism = unidentified
SEQUENCE: 120
MYNKAEIMKQ AWNWFNNSNV WLSDIEWVSY TDKEKTFSVC LRAAWSKAKE EVEESKEESK  60
HIAKSEELKA WNWAERKLGL HFNISDDEKF TSVKDETKIN FGLSVWACAM KAVKLHNDLF  120
PQTAA                                                              125

SEQ ID NO: 121         moltype = AA  length = 125
FEATURE                Location/Qualifiers
REGION                 1..125
                       note = Unknown bacterial, unknown viral (phage), or
                        syntheticCas9-inhibiting polypeptide
source                 1..125
```

```
                         mol_type = protein
                         organism = unidentified
SEQUENCE: 121
MFNKAEIMKQ AWNWFTDSNV WLSDIEWVSY TDKEKTFSVC LKAAWSKAKE EVKEVEKEIK  60
HISKSEELKA WNWAERKLGL HFNISDDEKF TSVKDETKIN FGLSVWACAM KAVKLHNDLF  120
PQTAA                                                             125

SEQ ID NO: 122           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
                         organism = unidentified
SEQUENCE: 122
MYNKAEIMKQ AWNWFNDSNV WLSDIEWASY TDKEKTFSVC LKAAWSKAKE EVKEVEKEIK  60
HISKSEELKA WNWAERKLGL HFNISDDEKF TSVKDETKIN FGLSVWACAM KAVKLHNDLF  120
PQTAA                                                             125

SEQ ID NO: 123           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
                         organism = unidentified
SEQUENCE: 123
MFNKAEIMKQ AWNWFTDSNV WLSDIEWASY TDKEKTFSVC LKAAWSKAKE EVKEVEKEIK  60
HISKSEELKA WNWAERKLGL HFNISDDEKF TSVKDETKIN FGLSVWACAM KAVKLHNDLF  120
PQTAA                                                             125

SEQ ID NO: 124           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
                         organism = unidentified
SEQUENCE: 124
MYNKAEIMKQ AWNWFTDSNV WLSDIEWASY TDKEKTFSVC LKAAWSKAKE EVKEVEKEIK  60
HISKSEELKA WNWAERKLGL HFNISDDEKF TSVKDETKIN FGLSVWACAM KAVKLHNDLF  120
PQTAA                                                             125

SEQ ID NO: 125           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
                         organism = unidentified
SEQUENCE: 125
MFNKAEIMKQ AWNWFTDSNV WLSDIEWVSY TDKEKTFSVC LKAAWSKAKE EFKEVEKEIK  60
HISKSEELKA WNWAERKLGL HFNISDDEKF TSVKNETKMN FGLSVWACAM KAVKLHNDLF  120
PQTAA                                                             125

SEQ ID NO: 126           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
                         organism = unidentified
SEQUENCE: 126
MYNKAEIMKQ AWNWFTDSNV WLSDIEWASY TDKEKTFSVC LKAAWSKAKE EVKEVEKEIK  60
HISKSEELKA WNWAERKLGL HFNISDDEKF TSVKDETKIN FGLSVWACAM KAVKLHNDLF  120
PQTVA                                                             125

SEQ ID NO: 127           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
```

```
                         organism = unidentified
SEQUENCE: 127
MYNKAEIMKQ AWNWFNDSNV WLSDIEWASY TDKEKTFSVC LKAAWSKAKE EVKEVEKEIK  60
HISKSEELKA WNWAERKLGL HFNISDDEKF TSVKDETKIN FGLSVWACAM KAVKLHSHLF  120
PQTAA                                                             125

SEQ ID NO: 128           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
                         organism = unidentified
SEQUENCE: 128
MYNKAEIMKQ AWNWFTDSNV WLSDIEWASY TDKEKTFSVC LKAAWSKAKE EVKEVEKEIK  60
HISKREELKA WNWAERKLGL HFNISDDEKF TSVKDETKIN FGLSVWACAM KAVKLHNDLF  120
PQTVA                                                             125

SEQ ID NO: 129           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
                         organism = unidentified
SEQUENCE: 129
MFNKAEIMKQ AWNWFTDSNV WLSDIEWVSY TDKEKTFSVC LKAAWSKAKE EVKEVEKEIK  60
HISKSEELKA WNWAERKLGL RFNISDDEKF TSVKDETKQH FGLSVWACAM KAVKLHNDLF  120
PQTAA                                                             125

SEQ ID NO: 130           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
                         organism = unidentified
SEQUENCE: 130
MYNKAEIMKQ AWNWFNDSNI WLSDIEWVSY TDKEKSFSVC LKAAWSKAKE EVEESKKESK  60
HIAKSEELKA WNWAEIKLGL RFNISDDEKF TSVKDETKMN FDLNVWACAM KAVKLHNDLF  120
PQTAA                                                             125

SEQ ID NO: 131           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
                         organism = unidentified
SEQUENCE: 131
MYNKAEIMKQ AWNWFTDSNV WLSDIEWVSY TDKEKTFSVC LKAAWSKAKE EVKEVEKEIK  60
HISKSEELKA WNWAERKLGL RFNISDDEKF TSVKDETKQH FGLSVWACAM KAVKLHNDLF  120
PQTAA                                                             125

SEQ ID NO: 132           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
                         organism = unidentified
SEQUENCE: 132
MYNKAEIMKQ AWNCFNDSNV WLSDIEWVSY TDKEKTFSVC LKAAWSKAKE EIEKSKKESK  60
HIAKSEELKA WNWAERKLGL RFNISDDEKF TSVKDETKQH FGLSVWACAM KAVKLHNDLF  120
PQTAA                                                             125

SEQ ID NO: 133           moltype = AA  length = 125
FEATURE                  Location/Qualifiers
REGION                   1..125
                         note = Unknown bacterial, unknown viral (phage), or
                          syntheticCas9-inhibiting polypeptide
source                   1..125
                         mol_type = protein
                         organism = unidentified
```

```
SEQUENCE: 133
MYNKAEIMKQ AWNCFNDSNV WLSDIEWVSY TDKEKTFSVC LKAAWSKAKE EIEESKKESK  60
HIAKSEELKA WNWAERKLGL RFNISDDEKF TSVKDETKQH FGLSVWACAM KAVKLHNDLF  120
PQTAA                                                              125

SEQ ID NO: 134         moltype = AA  length = 125
FEATURE                Location/Qualifiers
REGION                 1..125
                       note = Unknown bacterial, unknown viral (phage), or
                        syntheticCas9-inhibiting polypeptide
source                 1..125
                       mol_type = protein
                       organism = unidentified
SEQUENCE: 134
MYNKSEIMQQ AWNWFRDSSV WLSDIEWVSY TDKEKTFSVC LKAAWSKAKE EVEESKKESK  60
HIAKSEELKA WNWAESKLGL RFNISDDEKF TSVKDETKIN FGLSVWACAM KAVKLHNDLF  120
PQTAA                                                              125

SEQ ID NO: 135         moltype = AA  length = 125
FEATURE                Location/Qualifiers
REGION                 1..125
                       note = Unknown bacterial, unknown viral (phage), or
                        syntheticCas9-inhibiting polypeptide
source                 1..125
                       mol_type = protein
                       organism = unidentified
SEQUENCE: 135
MYNKAEIMKQ AWNWFTDSNV WLSDIEWASY TDKEKTFSVC LKAAWSKAKE EVKEVEKEIK  60
HISKREELKA WNLAERKLGL HFNISDDEKF TSVKDETKIN FGLSVWACAM KAVKLHNDLF  120
PQTVA                                                              125

SEQ ID NO: 136         moltype = AA  length = 117
FEATURE                Location/Qualifiers
REGION                 1..117
                       note = Unknown bacterial, unknown viral (phage), or
                        syntheticCas9-inhibiting polypeptide
source                 1..117
                       mol_type = protein
                       organism = unidentified
SEQUENCE: 136
MFNKAEIMKQ AWNWFTDSNV WLSDIEWASY TDKEKTFSVC LKAAWSKAKE EVKEVEKEIK  60
HISKSEELKA WNWAERKLGL HFNISDDEKF TSVKDETKIN FGLSVWACAM KAVKLHN     117

SEQ ID NO: 137         moltype = AA  length = 128
FEATURE                Location/Qualifiers
REGION                 1..128
                       note = Unknown bacterial, unknown viral (phage), or
                        syntheticCas9-inhibiting polypeptide
source                 1..128
                       mol_type = protein
                       organism = unidentified
SEQUENCE: 137
MKKVTYDKSG IMKEAWNLFN NDDITLADFE HLGWMEWKSE KTFALCLKEA WGREKEVVER  60
VNQKFANAET SEEAKAWDWA CKKLGVAFEM DAYTKMTNVE DMEKEAWPGT SVWSLAMRAV  120
KLHMEVAA                                                           128

SEQ ID NO: 138         moltype = AA  length = 123
FEATURE                Location/Qualifiers
REGION                 1..123
                       note = Unknown bacterial, unknown viral (phage), or
                        syntheticCas9-inhibiting polypeptide
source                 1..123
                       mol_type = protein
                       organism = unidentified
SEQUENCE: 138
MRYNKSEIMK NAWAMFNSCN WGAENFKFVS VEEKTFAACL KEAWAEEKEY VEEKIKESAN  60
APKSEEAKAW DWACRKLNAN KLQNVEATDK VAWVSEMAKE MWSSNIWAQA IKAVKLHIKL  120
FAA                                                                123

SEQ ID NO: 139         moltype = AA  length = 126
FEATURE                Location/Qualifiers
REGION                 1..126
                       note = Unknown bacterial, unknown viral (phage), or
                        syntheticCas9-inhibiting polypeptide
source                 1..126
                       mol_type = protein
                       organism = unidentified
SEQUENCE: 139
MKYNKSEIMK NAWTMFNDDN FDTSYYEYAT AEVYGQKTFS ECLKESWGRE KAYQEEKEKR  60
```

```
LVDAPKSEEA KAWDWACRKL NVNELQNIDA TDKVFYVEGM AKEMWSSNVW AQAIKAVKLH  120
IELFVA                                                              126

SEQ ID NO: 140          moltype = AA  length = 129
FEATURE                 Location/Qualifiers
REGION                  1..129
                        note = Unknown bacterial, unknown viral (phage), or
                         syntheticCas9-inhibiting polypeptide
source                  1..129
                        mol_type = protein
                        organism = unidentified
SEQUENCE: 140
MKKVAYDKSG IMKEAWEMFN RNYQICDFEY ADFSGREYFE YASFADCLKE AWAHEKEVVE  60
RVNQKYADAE TSEEVKAWDW ACKKLGVAFE MDAYTKITNV EGMEKEAWPG TSVWSLAMRA  120
VKLHMEVAA                                                           129

SEQ ID NO: 141          moltype = AA  length = 123
FEATURE                 Location/Qualifiers
REGION                  1..123
                        note = Unknown bacterial, unknown viral (phage), or
                         syntheticCas9-inhibiting polypeptide
source                  1..123
                        mol_type = protein
                        organism = unidentified
SEQUENCE: 141
MAKYNKSEIM TQAWTLFNSD NFDTCDYEYT TALVYGQKNF SDCLKEAWGR EKAIVERMAE  60
QEANAPLSEE AKAWDWACRK LGVTAEVTAV EKVRYVDDMA KEMWSANVWK QAIKAVQLYA  120
TVA                                                                 123

SEQ ID NO: 142          moltype = AA  length = 123
FEATURE                 Location/Qualifiers
REGION                  1..123
                        note = Unknown bacterial, unknown viral (phage), or
                         syntheticCas9-inhibiting polypeptide
source                  1..123
                        mol_type = protein
                        organism = unidentified
SEQUENCE: 142
MAKYNKSEIM TQAWTLFNSD NFDTCDYEYA TALVYGQKTF SDCLKEAWGR EKAIVERMAE  60
KEANAPLSEE AKAWDWACRK LGVTAEVTAV EKVRYVDDMA KEMWSTNVWK QAIKAVQLYA  120
TVA                                                                 123

SEQ ID NO: 143          moltype = AA  length = 124
FEATURE                 Location/Qualifiers
REGION                  1..124
                        note = Unknown bacterial, unknown viral (phage), or
                         syntheticCas9-inhibiting polypeptide
source                  1..124
                        mol_type = protein
                        organism = unidentified
SEQUENCE: 143
MAKYNKSEIM KNAWAMFNSY EWDVENFKFV SAENKTFSNC LKEAWAEEKE YVERKAKETA  60
EAPKSEEAKA WDWACRKLNV NDLQNIDATD KVFYVVDMQK EMWTSNVWAQ AIKAVELYVK  120
LGLA                                                                124

SEQ ID NO: 144          moltype = AA  length = 124
FEATURE                 Location/Qualifiers
REGION                  1..124
                        note = Unknown bacterial, unknown viral (phage), or
                         syntheticCas9-inhibiting polypeptide
source                  1..124
                        mol_type = protein
                        organism = unidentified
SEQUENCE: 144
MTKYNKSEIM KNAWAMFNSY EWDVENFKFV SAENKTFSNC LKEAWAEEKE YVERKAKETA  60
EAPRSEEAKA WDWACRKLNV NDLQNIDATD KVFYVVDMQK EMWTSNVWAQ AIKAVELYVK  120
LGLA                                                                124

SEQ ID NO: 145          moltype = AA  length = 124
FEATURE                 Location/Qualifiers
REGION                  1..124
                        note = Unknown bacterial, unknown viral (phage), or
                         syntheticCas9-inhibiting polypeptide
source                  1..124
                        mol_type = protein
                        organism = unidentified
SEQUENCE: 145
MTKYNKSEIM KNAWAMFNSY EWDVENFKFV SAENKTFSNC LKEAWAEEKE YVERKAKETA  60
EAPKSEEAKA WDWACRKLNV NDLQNIDATD KVFYVVDMQK EMWTSNIWAQ AIKAVELYVK  120
```

```
LGLA                                                              124

SEQ ID NO: 146          moltype = AA  length = 124
FEATURE                 Location/Qualifiers
REGION                  1..124
                        note = Unknown bacterial, unknown viral (phage), or
                         syntheticCas9-inhibiting polypeptide
source                  1..124
                        mol_type = protein
                        organism = unidentified
SEQUENCE: 146
MTKYNKSEIM KNAWAMFNSY EWDVENFKFV SAENKTFSNC LKEAWAEEKE YVERKAKEAA  60
EASKSEEAKA WDWACRKLNV NDLQNIDATN KVFYVVDMQK EMWTSNVWAQ AIKAVELYVK  120
LGLA                                                              124

SEQ ID NO: 147          moltype = AA  length = 87
FEATURE                 Location/Qualifiers
REGION                  1..87
                        note = Unknown bacterial, unknown viral (phage), or
                         syntheticCas9-inhibiting polypeptide
source                  1..87
                        mol_type = protein
                        organism = unidentified
SEQUENCE: 147
MNINDLIREI KNKDYTVKLS GTDSNSITQL IIRVNNDGNE YVISESENES IVEKFISAFK  60
NGWNQEYEDE EEFYNDMQTI TLKSELN                                     87

SEQ ID NO: 148          moltype = AA  length = 87
FEATURE                 Location/Qualifiers
REGION                  1..87
                        note = Unknown bacterial, unknown viral (phage), or
                         syntheticCas9-inhibiting polypeptide
source                  1..87
                        mol_type = protein
                        organism = unidentified
SEQUENCE: 148
MNINELIREI KNKDYTAKLS GTDSNSITQL IIRVNNDGNE YVISESENES IVEKFISAFK  60
NGWNQEYEDE EEFYNDMQTI TLKSELN                                     87

SEQ ID NO: 149          moltype = AA  length = 87
FEATURE                 Location/Qualifiers
REGION                  1..87
                        note = Unknown bacterial, unknown viral (phage), or
                         syntheticCas9-inhibiting polypeptide
source                  1..87
                        mol_type = protein
                        organism = unidentified
SEQUENCE: 149
MNINELIREV KNKDYTAKLS GTDSNSITQL IIRVNNDGNE YVISESENES IVEKFISAFK  60
NGWNQEYEDE EEFYNDMQTI TLKSELN                                     87

SEQ ID NO: 150          moltype = AA  length = 87
FEATURE                 Location/Qualifiers
REGION                  1..87
                        note = Unknown bacterial, unknown viral (phage), or
                         syntheticCas9-inhibiting polypeptide
source                  1..87
                        mol_type = protein
                        organism = unidentified
SEQUENCE: 150
MNINELIREI KNKDYTAKLS GTDSNSIAQL IIRVNNDGNE YVISESENES IVEKFISAFK  60
NGWNQEYEDE EEFYNDMQTI TLKSELN                                     87

SEQ ID NO: 151          moltype = AA  length = 87
FEATURE                 Location/Qualifiers
REGION                  1..87
                        note = Unknown bacterial, unknown viral (phage), or
                         syntheticCas9-inhibiting polypeptide
source                  1..87
                        mol_type = protein
                        organism = unidentified
SEQUENCE: 151
MNINELIREI KNKDYTAKLS GTDSNSITQL IIHVNNDGNE YVISESENES IVEKFISAFK  60
NGWNQEYEDE EEFYNDMQTI TLKSELN                                     87

SEQ ID NO: 152          moltype = AA  length = 87
FEATURE                 Location/Qualifiers
REGION                  1..87
                        note = Unknown bacterial, unknown viral (phage), or
```

```
                         syntheticCas9-inhibiting polypeptide
source                   1..87
                         mol_type = protein
                         organism = unidentified
SEQUENCE: 152
MNINDLIREI KNKDYTVKLS GTDSNSITQL IINVNNDGNE YGISESNFES IVEKFVSNFE  60
NGWDGAYEDE EEFYNDMQAI ILKSELN                                     87

SEQ ID NO: 153           moltype = AA  length = 87
FEATURE                  Location/Qualifiers
REGION                   1..87
                         note = Unknown bacterial, unknown viral (phage), or
                          syntheticCas9-inhibiting polypeptide
source                   1..87
                         mol_type = protein
                         organism = unidentified
SEQUENCE: 153
MNINDLIREI KNKDYTVKLS GTDSNSITQL IINVNNDGNE YGISESNFES IVEKFVSNFE  60
NGWDGAYEDE EEFYNDMQAI ILKSESN                                     87

SEQ ID NO: 154           moltype = AA  length = 87
FEATURE                  Location/Qualifiers
REGION                   1..87
                         note = Unknown bacterial, unknown viral (phage), or
                          syntheticCas9-inhibiting polypeptide
source                   1..87
                         mol_type = protein
                         organism = unidentified
SEQUENCE: 154
MNISELIREI KNKDYTVRLE GTDDNSITKL IIDVDNDGNE YVISESKNES IAEKFASTFK  60
NGWNKEYEDE EEFYNDMQSI ILKSELN                                     87

SEQ ID NO: 155           moltype = AA  length = 87
FEATURE                  Location/Qualifiers
REGION                   1..87
                         note = Unknown bacterial, unknown viral (phage), or
                          syntheticCas9-inhibiting polypeptide
source                   1..87
                         mol_type = protein
                         organism = unidentified
SEQUENCE: 155
MNISELIREI KNKDYAVRLE GTDDNSITKL IIDVDNDGNE YVISESKNES IAEKFASTFK  60
NGWNKEYEDE EEFYNDMQSI ILKSELN                                     87

SEQ ID NO: 156           moltype = AA  length = 160
FEATURE                  Location/Qualifiers
REGION                   1..160
                         note = Unknown bacterial, unknown viral (phage), or
                          syntheticCas9-inhibiting polypeptide
source                   1..160
                         mol_type = protein
                         organism = unidentified
SEQUENCE: 156
MAGYLKRYAE DRGWTLYRLA KESHLSDSTL RTADLTTLNK LSVINIKKIS EAVGETPGEV  60
LDDLIKFEER VEKMNISELI REIKNKDYAV RLEGTDDNSI TKLIIDVDND GNEYVISESK  120
NESIAEKFAS TFKNGWNKEY EDEEEFYNDM QSIILKSELN                        160

SEQ ID NO: 157           moltype = AA  length = 86
FEATURE                  Location/Qualifiers
REGION                   1..86
                         note = Unknown bacterial, unknown viral (phage), or
                          syntheticCas9-inhibiting polypeptide
source                   1..86
                         mol_type = protein
                         organism = unidentified
SEQUENCE: 157
MNLKELVREI KNKDYTAKLS GTDSNSITQL IIHVNNDGNE YGISESNFES IVEKFVSTFE  60
NGWDGAYEDE EEFYNDMQDI VNRHFK                                      86

SEQ ID NO: 158           moltype = AA  length = 86
FEATURE                  Location/Qualifiers
REGION                   1..86
                         note = Unknown bacterial, unknown viral (phage), or
                          syntheticCas9-inhibiting polypeptide
source                   1..86
                         mol_type = protein
                         organism = unidentified
SEQUENCE: 158
MNLKELVREI KNKDYTAKLS GTDSNSITQL IIHVNNDGNE YGISESNFES IVEKFVSNFE  60
```

```
NGWDGAYEDE EEFYNDMQDI VNRHFK                                        86

SEQ ID NO: 159          moltype = AA  length = 151
FEATURE                 Location/Qualifiers
REGION                  1..151
                        note = Unknown bacterial, unknown viral (phage), or
                         syntheticCas9-inhibiting polypeptide
source                  1..151
                        mol_type = protein
                        organism = unidentified
SEQUENCE: 159
MKINELVREI KSRDYTVRLN GTDSNSITKL IIDVNNDGNE YVISERQDTS IVESFADSFI  60
DGWTGTYEDE EDFYNDMQEI AQDIILETLK EAFENNNYNT DEVDTDLFDG YQIKLAMEYD  120
NIGELATSVN KTKHFTAYMD ASTDFMIIEK Y                                  151

SEQ ID NO: 160          moltype = AA  length = 147
FEATURE                 Location/Qualifiers
REGION                  1..147
                        note = Unknown bacterial, unknown viral (phage), or
                         syntheticCas9-inhibiting polypeptide
source                  1..147
                        mol_type = protein
                        organism = unidentified
SEQUENCE: 160
MSIIAIKKEI HAKGYKVTGT HQGYIAQINF DGTGNEYPLP ATWDEFIETF KDGWNGTYED  60
EQAFFNDMQE VALKEILDEL TGALFCQDIT TYDFTIDDVK KKVITLDKPT FEEDAEDLII  120
EFDSTCFWDA TVENDKIKIT VRNKSRY                                       147

SEQ ID NO: 161          moltype = AA  length = 99
FEATURE                 Location/Qualifiers
REGION                  1..99
                        note = Unknown bacterial, unknown viral (phage), or
                         syntheticCas9-inhibiting polypeptide
source                  1..99
                        mol_type = protein
                        organism = unidentified
SEQUENCE: 161
MSIIAIKKEI HAKGYKVTGT HQGYIAQINF DGTGNEYPLP ATWDEFIETF KDGWNGTYED  60
EQAFFNDMQE IALDEILDEL IDVLYNLDIT TYNFTIDDS                          99

SEQ ID NO: 162          moltype = AA  length = 147
FEATURE                 Location/Qualifiers
REGION                  1..147
                        note = Unknown bacterial, unknown viral (phage), or
                         syntheticCas9-inhibiting polypeptide
source                  1..147
                        mol_type = protein
                        organism = unidentified
SEQUENCE: 162
MSIIAIKKEI HAKGYKVTGT HQGYIAQINF DGTGNEYPLP ATWDEFIETF KDGWNGTYED  60
EQAFFNDMQE IALEEILDEL TGALFCQDIT TYDFTIDDVK KKVITLDKPT FEEDAEDLII  120
EFDSTCFWDA TVENDKIKIT VRNKSRY                                       147

SEQ ID NO: 163          moltype = AA  length = 149
FEATURE                 Location/Qualifiers
REGION                  1..149
                        note = Unknown bacterial, unknown viral (phage), or
                         syntheticCas9-inhibiting polypeptide
source                  1..149
                        mol_type = protein
                        organism = unidentified
SEQUENCE: 163
MSIIAINKEI RAKGYKVTGT HQGYIAQINF EGTGNEYPLP ATWDEFIETF KDGWNGTYED  60
EQAFFNDMQE IALDEILDEL IDVLYNLDIT TYNFTIDDVK KKVITLNKPI DEEETEDLVQ  120
EFNVTCFWDA TVEDDKVKVT IRNKNRAIS                                     149

SEQ ID NO: 164          moltype = AA  length = 146
FEATURE                 Location/Qualifiers
REGION                  1..146
                        note = Unknown bacterial, unknown viral (phage), or
                         syntheticCas9-inhibiting polypeptide
source                  1..146
                        mol_type = protein
                        organism = unidentified
SEQUENCE: 164
MSTTAINKEI HAKGYKVTGT HQGYIAQINF DGTGNEYPLP ATWEKFIETF KDGWDGTYED  60
EQAFFNDMQE IALDEILDEL IDVLYNLDIT TYNFTIDDVK KKVITLNKPI DEEETEDLVQ  120
EFNVTCFWNA IVEDDKVKIT VRNKSK                                        146
```

```
SEQ ID NO: 165         moltype = AA  length = 146
FEATURE                Location/Qualifiers
REGION                 1..146
                       note = Unknown bacterial, unknown viral (phage), or
                        syntheticCas9-inhibiting polypeptide
source                 1..146
                       mol_type = protein
                       organism = unidentified
SEQUENCE: 165
MSTTAINKEI HAKGYKVTGT HQGYIAQINF DGTGNEYPLP ATWEEFIETF KDGWDGTYED  60
EQAFFNDMQE IALDEILDEL IDVLYNLDIT TYNFTIDDVK KKVITLNKPI DEEETEDLVQ  120
EFNVTCFWNA IVEDDKVKIT VRNKSK                                      146

SEQ ID NO: 166         moltype = AA  length = 146
FEATURE                Location/Qualifiers
REGION                 1..146
                       note = Unknown bacterial, unknown viral (phage), or
                        syntheticCas9-inhibiting polypeptide
source                 1..146
                       mol_type = protein
                       organism = unidentified
SEQUENCE: 166
MSTTAINKEI HAKGYKVTGT HQGYVAQINF DGTGNEYPLP ATWEEFIETF KDGWDGTYKD  60
EQAFFNDMQE IALDEILDEL IDTLYNLDIT TYDFTIDDIK KKVITLDKPT DREETEDLVQ  120
EFNVTCFWNA IVEDDKVKVT VRNKSK                                      146

SEQ ID NO: 167         moltype = AA  length = 130
FEATURE                Location/Qualifiers
REGION                 1..130
                       note = Unknown bacterial, unknown viral (phage), or
                        syntheticCas9-inhibiting polypeptide
VARIANT                112
                       note = Xaa can any amino acid
source                 1..130
                       mol_type = protein
                       organism = unidentified
SEQUENCE: 167
MTGTHQGYIA QINFDGTGNE YPLPATWDEF IETFKDGWNG TYEDEQAFFN DMQEVALKEI  60
LDELIDVLYN LDITTYNFTI DDVKKKVITL NKPTDEEDAE DLVIEFDSTC FXDATVENDK  120
IKVTVRNKSK                                                        130

SEQ ID NO: 168         moltype = AA  length = 149
FEATURE                Location/Qualifiers
REGION                 1..149
                       note = Unknown bacterial, unknown viral (phage), or
                        syntheticCas9-inhibiting polypeptide
source                 1..149
                       mol_type = protein
                       organism = unidentified
SEQUENCE: 168
MSTTAINKEI HAKGYKVTGT HQGYMAQINF DGTGNEFPLP ATWEEFIETF KDGWDGTYED  60
EQAFFNDMQE VALEELLDEL TDVFYNLDIT AYDFTVDDVK KKVITLDKPT DREETEDLVQ  120
EFKATCFWNA VVEDDKVKVT IRNKNRAIS                                   149

SEQ ID NO: 169         moltype = AA  length = 119
FEATURE                Location/Qualifiers
REGION                 1..119
                       note = Unknown bacterial, unknown viral (phage), or
                        syntheticCas9-inhibiting polypeptide
source                 1..119
                       mol_type = protein
                       organism = unidentified
SEQUENCE: 169
MQFVVTNKSE LFKFAWKIFK ANKDIAFSEC LQNAWFQYKR YLNREAIKAA QQRKLAKFIA  60
DTENEEVKAW NWAEKKLGVA LNLTDAEKER NVRNMYKEMW NANVWATAIK AVKLHMEIG   119

SEQ ID NO: 170         moltype = AA  length = 148
FEATURE                Location/Qualifiers
REGION                 1..148
                       note = Unknown bacterial, unknown viral (phage), or
                        syntheticCas9-inhibiting polypeptide
source                 1..148
                       mol_type = protein
                       organism = unidentified
SEQUENCE: 170
MNELRSLEMS INAKKYDTRL ESGNRVLNIG FGDGEDYPVC SSSRYSLKES FIECFKDGWS  60
GTYRDEKELM EDMQEIAQEL ILEELTDIFE YYEFNTDEID TDLFKGFTFD VDSDLEDSMA  120
LMKAINATKY FEARSSSWYA SFEVSYIG                                    148
```

```
SEQ ID NO: 171          moltype = RNA  length = 28
FEATURE                 Location/Qualifiers
misc_feature            1..28
                        note = synthetic crRNA spacer sequence
source                  1..28
                        mol_type = other RNA
                        organism = synthetic construct
SEQUENCE: 171
gatagcaaga tggatagtta gttttaga                                     28

SEQ ID NO: 172          moltype = DNA  length = 36
FEATURE                 Location/Qualifiers
misc_feature            1..36
                        note = synthetic protospacer sequence (phiJ0161a prophage))
source                  1..36
                        mol_type = other DNA
                        organism = synthetic construct
SEQUENCE: 172
acgctccgta actatccatc ttgctatctg tatatg                            36

SEQ ID NO: 173          moltype = DNA  length = 36
FEATURE                 Location/Qualifiers
misc_feature            1..36
                        note = synthetic protospacer sequence (phiJ0161a prophage))
                         - complement
source                  1..36
                        mol_type = other DNA
                        organism = synthetic construct
SEQUENCE: 173
catatacaga tagcaagatg gatagttacg gagcgt                            36

SEQ ID NO: 174          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 174
tggttctttc gctttcacaa gatacttttg                                   30

SEQ ID NO: 175          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 175
acccgtttct gatgaacgat acactgttgt                                   30

SEQ ID NO: 176          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 176
catctatcaa gctacaaatt ggatgtacac                                   30

SEQ ID NO: 177          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 177
aagacgaagt gaacgaagag tctttcccag                                   30

SEQ ID NO: 178          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 178
```

```
taacgtttgg aaccctaggc attatgttgc                                   30

SEQ ID NO: 179          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 179
gagaatgcaa gaattaatta atgagtacag                                   30

SEQ ID NO: 180          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 180
tgttgttata aacactgtta actgttgttc                                   30

SEQ ID NO: 181          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 181
tctatgcctt gatattttaa atgaccgagt                                   30

SEQ ID NO: 182          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 182
taagcaagtt gcagataaga aaaccatgtc                                   30

SEQ ID NO: 183          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 183
ttttgatgat gaaccagaat ggatttatta                                   30

SEQ ID NO: 184          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 184
ctatccgcaa acacatgttg atggcgtcgt                                   30

SEQ ID NO: 185          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
SEQUENCE: 185
aaaaaaatat taacacgaat tagatactaa                                   30

SEQ ID NO: 186          moltype = DNA  length = 30
FEATURE                 Location/Qualifiers
misc_feature            1..30
                        note = synthetic spacer sequence from FIG. 7B
source                  1..30
                        mol_type = other DNA
                        organism = synthetic construct
```

```
SEQUENCE: 186
caaggcactt ttcatttttt gaacacgcca                                 30

SEQ ID NO: 187         moltype = DNA  length = 30
FEATURE                Location/Qualifiers
misc_feature           1..30
                       note = synthetic spacer sequence from FIG. 7B
source                 1..30
                       mol_type = other DNA
                       organism = synthetic construct
SEQUENCE: 187
aactgttgtg ccttcctttg cgtgcacttg                                 30

SEQ ID NO: 188         moltype = DNA  length = 30
FEATURE                Location/Qualifiers
misc_feature           1..30
                       note = synthetic spacer sequence from FIG. 7B
source                 1..30
                       mol_type = other DNA
                       organism = synthetic construct
SEQUENCE: 188
tctttttgat gtattcattt attgttagaa                                 30

SEQ ID NO: 189         moltype = DNA  length = 30
FEATURE                Location/Qualifiers
misc_feature           1..30
                       note = synthetic spacer sequence from FIG. 7B; includes
                        self-targetingspacer
source                 1..30
                       mol_type = other DNA
                       organism = synthetic construct
SEQUENCE: 189
agcatataca gatagcaaga tggatagtta                                 30

SEQ ID NO: 190         moltype = DNA  length = 30
FEATURE                Location/Qualifiers
misc_feature           1..30
                       note = synthetic spacer sequence from FIG. 7B
source                 1..30
                       mol_type = other DNA
                       organism = synthetic construct
SEQUENCE: 190
ttcaaggtca agatcaagag caagaatgcc                                 30

SEQ ID NO: 191         moltype = DNA  length = 30
FEATURE                Location/Qualifiers
misc_feature           1..30
                       note = synthetic spacer sequence from FIG. 7B
source                 1..30
                       mol_type = other DNA
                       organism = synthetic construct
SEQUENCE: 191
cgtcgcataa tactgttcct ctgccgttcg                                 30

SEQ ID NO: 192         moltype = DNA  length = 29
FEATURE                Location/Qualifiers
misc_feature           1..29
                       note = synthetic spacer sequence from FIG. 7B
source                 1..29
                       mol_type = other DNA
                       organism = synthetic construct
SEQUENCE: 192
gaatattctt ccccccatga ctaacaggg                                  29

SEQ ID NO: 193         moltype = DNA  length = 36
FEATURE                Location/Qualifiers
misc_feature           1..36
                       note = synthetic spacer sequence from FIG. 7B
source                 1..36
                       mol_type = other DNA
                       organism = synthetic construct
SEQUENCE: 193
gttttagagc tatgttattt tgaatgctac caaaac                          36

SEQ ID NO: 194         moltype = RNA  length = 38
FEATURE                Location/Qualifiers
misc_feature           1..38
                       note = synthetic crRNA spacer sequence
source                 1..38
```

```
                        mol_type = other RNA
                        organism = synthetic construct
SEQUENCE: 194
agcatataca gatagcaaga tggatagtta gttttaga                          38

SEQ ID NO: 195          moltype = DNA  length = 46
FEATURE                 Location/Qualifiers
misc_feature            1..46
                        note = synthetic target DNA sequence
source                  1..46
                        mol_type = other DNA
                        organism = synthetic construct
SEQUENCE: 195
acgctccgta actatccatc ttgctatctg tatatgcttt tgcaga                 46

SEQ ID NO: 196          moltype = DNA  length = 46
FEATURE                 Location/Qualifiers
misc_feature            1..46
                        note = synthetic target DNA sequence (complement)
source                  1..46
                        mol_type = other DNA
                        organism = synthetic construct
SEQUENCE: 196
tctgcaaaag catatacaga tagcaagatg gatagttacg gagcgt                 46

SEQ ID NO: 197          moltype = DNA  length = 154
FEATURE                 Location/Qualifiers
source                  1..154
                        mol_type = genomic DNA
                        organism = Streptocococcus pyogenes
SEQUENCE: 197
tatggctgat aaatttcttt gaatttctcc ttgattattt gttataaaag ttataaaata  60
atcttgttgg aaccattcaa aacagcatag caagttaaaa taaggctagt ccgttatcaa  120
cttgaaaaag tggcaccgag tcggtgcttt tttt                              154

SEQ ID NO: 198          moltype = DNA  length = 157
FEATURE                 Location/Qualifiers
source                  1..157
                        mol_type = genomic DNA
                        organism = Listeria monocytogenes
SEQUENCE: 198
catattcttc atcccttcaa cctgttttta gttgcattct ttttataatt tggtacaatg  60
tatatattgt tagtattcaa aataacatag caagttaaaa taaggctttg tccgttatca  120
acttttaatt aagtagcgct gtttcggcgc ttttttt                           157

SEQ ID NO: 199          moltype = DNA  length = 157
FEATURE                 Location/Qualifiers
source                  1..157
                        mol_type = genomic DNA
                        organism = Listeria monocytogenes
SEQUENCE: 199
catattcttc atcccttcaa cctgttttta gttgcattct ttttataatt tggtacaatg  60
tatatattgt tagtattcaa aataacatag caagttaaaa taaggctttg tccgttatca  120
acttttaatt aagtagcgct gtttcggcgc ttttttt                           157

SEQ ID NO: 200          moltype = DNA  length = 157
FEATURE                 Location/Qualifiers
source                  1..157
                        mol_type = genomic DNA
                        organism = Listeria innocua
SEQUENCE: 200
catattcttc atcccttcaa cctattttta gttgcattct ttttataatt tggtacaatg  60
tatatattgt tagtattcaa aataacatag caagttaaaa taaggctttg tccgttatca  120
acttttaatt aagtagcgct gtttcggcgc ttttttt                           157

SEQ ID NO: 201          moltype = DNA  length = 246
FEATURE                 Location/Qualifiers
source                  1..246
                        mol_type = genomic DNA
                        organism = Streptocococcus pyogenes
SEQUENCE: 201
ttagatgaag attatttctt aataactaaa aatatggtat aatactctta ataaatgcag  60
taatacaggg gcttttcaag actgaagtct agctgagaca aatagtgcga ttacgaaatt  120
ttttagacaa aaatagtcta cgaggtttta gagctatgct gttttgaatg gtcccaaaac  180
tgcgctggtt gatttcttct tgcgcttttt gttttagagc tatgctgttt tgaatggtcc  240
caaaac                                                             246

SEQ ID NO: 202          moltype = DNA  length = 233
FEATURE                 Location/Qualifiers
```

```
source                  1..233
                        mol_type = genomic DNA
                        organism = Listeria monocytogenes
SEQUENCE: 202
taaggtaacc gctgttcttt gaaaacaaaa taaattttat gtaaaccata aaatagcatt  60
caaaattgaa atcttgctat ggatgaatgg cgcgattacg gaatcttgga ggaaagaaaa  120
aattctgcga ggttttagag ctatgttatt ttgaatgcta ccaaaactcg tgatttcttc  180
ctcatgcgcg cttttgagtt ttagagctat gttattttga atgctaccaa aac         233

SEQ ID NO: 203          moltype = DNA  length = 233
FEATURE                 Location/Qualifiers
source                  1..233
                        mol_type = genomic DNA
                        organism = Listeria monocytogenes
SEQUENCE: 203
taaggtaacc gctgttcttt gaaaacaaaa taaattttat gtaaaccata aaatagcatt  60
caaaattgaa atcttgctat ggatgaatgg cgcgattacg gaatcttgga ggaaagaaaa  120
aattctgcga ggttttagag ctatgttatt ttgaatgcta ccaaaactgg ttctttcgct  180
ttcacaagat acttttggtt ttagagctat gttattttga atgctaccaa aac         233

SEQ ID NO: 204          moltype = DNA  length = 231
FEATURE                 Location/Qualifiers
source                  1..231
                        mol_type = genomic DNA
                        organism = Listeria innocua
SEQUENCE: 204
tagagttcaa atgatctttg aaaactaaat agattttatg tgaaccataa aataagcatt  60
caaaattgaa atcttgctat ggatgaatgg cgcgattacg aaatctagga gaataaaaaa  120
ttctacgagg ttttagagct atgttatttt gaatgctaac aaaaccgtag cgctttggta  180
actttgccta ggatagtttt agagctatgt tattttgaat gctaacaaaa c           231

SEQ ID NO: 205          moltype = AA  length = 1368
FEATURE                 Location/Qualifiers
source                  1..1368
                        mol_type = protein
                        organism = Streptocococcus pyogenes
SEQUENCE: 205
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD               1368

SEQ ID NO: 206          moltype = AA  length = 1334
FEATURE                 Location/Qualifiers
source                  1..1334
                        mol_type = protein
                        organism = Listeria monocytogenes
SEQUENCE: 206
MKNPYTIGLD IGTNSVGWAV LTNQYDLVKR KMKVAGNSDK KQIKKNFWGV RLFDDGQTAV  60
DRRMNRTARR RIERRRNRIS YLQEIFAVEM ANIDANFFCR LNDSFYVDSE KRNSRHPFFA  120
TIEEEVAYHK NYRTIYHLRE ELVNSSEKAD LRLVYLALAH IIKYRGNFLI EGALDTKNTS  180
VDGVYEQFIQ TYNQVFMSNI EEGTLAKVEE NIEVANILAG KFTRREKFER ILQLYPGEKS  240
TGMFAQFISL IVGSKGNFQK VFDLIEKTDI ECAKDSYEED LEALLAIIGD EYAELFVAAK  300
NTYNAVVLSS IITVTATETN AKLSASMIER FDAHEKDLGE LKAFIKLHLP KQYQEIFNNA  360
AIDGYAGYID GKTKQVDFYK YLKTILENIE GADYFIAKIE EENFLRKQRT FDNGAIPHQL  420
HLEELEAIIH QQAKYYPFLR EDYEKIKSLV TFRIPYFVGP LAKGQSEFAW LTRKADGEIR  480
PWNIEEKVDF GKSAVDFIEK MTNKDTYLPK ENVLPKHSLC YQKYMVYNEL TKVRYIDDQG  540
KTNYFSGQEK QQIFNDLFKQ KRKVKKKDLE LFLRNINHIE SPTIEGLEDS FNASYATYHD  600
LLKVGMKQEI LDNPLNTEML EDIVKILTVF EDKPMIKEQL QQFSDVLDGG VLKKLERRHY  660
TGWGRLSAKL LVGIREKQSH LTILDYLMND DGLNRNLMQL INDSNLSFKS IIEKEQVSTT  720
```

```
DKDLQSIVAD LAGSPAIKKG ILQSLKIVDE LVSIMGYPPQ TIVVEMAREN QTTGKGKNNS  780
KPRYKSLEKA IKEFGSKILK EHPTDNQELK NNRLYLYYLQ NGKDMYTGQE LDIHNLSNYD  840
IDHIVPQSFI TDNSIDNLVL TSSAGNREKG GDVPPLEIVR KRKVFWEKLY QGNLMSKRKF  900
DYLTKAERGG LTDADKARFI HRQLVETRQI TKNVANILHQ RFNNETDNHG NTMEQVRIVT  960
LKSALVSQFR KQFQLYKVRE VNDYHHAHDA YLNGVVANTL LKVYPQLEPE FVYGEYHQFD  1020
WFKANKATAK KQFYTNIMLF FGQKERIIDE NGEILWDKKY LETIKKVLDY RQMNIVKKTE  1080
IQKGEFSKAT IKPKGNSSKL IPRKENWDPM KYGGLDSPNM AYAVIIEHAK GKKKLIFEKK  1140
IIRITIMERK MFEKDEEAFL EEKGYRHPKV LTKLPKYTLY ECEKGRRRML ASANEAQKGN  1200
QLVLSNHLVS LLYHAKNCEA SDGKSLKYIE AHRETFSELL AQVSEFATRY TLADANLSKI  1260
NNLFEQNKEG DIQAIAQSFV DLMAFNAMGA PASFKFFEAT IDRKRYTNLK ELLSSTIIYQ  1320
SITGLYESRK RLDD                                                   1334

SEQ ID NO: 207          moltype = AA  length = 1334
FEATURE                 Location/Qualifiers
source                  1..1334
                        mol_type = protein
                        organism = Listeria monocytogenes
SEQUENCE: 207
MKNPYTIGLD IGTNSVGWAV LTNQYDLVKR KMKVAGNSDK KQIKKNFWGV RLFDDGQTAV  60
DRRMNRTARR RIERRRNRIS YLQEIFAVEM ANIDANFFCR LNDSFYVDSE KRNSRHPFFA  120
TIEEEVAYHD NYRTIYHLRE KLVNSSEKAD LRLVYLALAH IIKYRGNFLI EGALDTKNTS  180
VDEVYKQFIE TYNQVFMSNI EEGALAKVEE NIEVANILAG KFTRREKFER ILQLYPGEKS  240
TGMFAQFISL IVGSKGNFQK VFDLIEKTDI ECAKDSYEED LETLLAIIGD EYAELFVAAK  300
NTYNAVVLSS IITVTDTETN AKLSASMIER FDAHEKDLVE LKAFIKLNLP KQYEEIFSNA  360
AIDGYAGYID GKTKQVDFYK YLKTILENIE GSDYFIAKIE EENFLRKQRT FDNGAIPHQL  420
HLEELEAIIH QQAKYYPFLK EDYDKIKSLV TFRIPYFVGP LANGQSEFAW LTRKADGEIR  480
PWNIEEKVDF GKSAVDFIEK MTNKDTYLPK ENVLPKHSLC YQKYMVYNEL TKIRYIDDQG  540
KTNYFSGREK QQVFNDLFKQ KRKVKKKDLE LFLRNINHIE SPTIEGLEDS FNASYATYHD  600
LLKVGMKQEI LDNPLNTEML EDIVKILTVF EDKPMIKEQL QQFSDVLDGG VLKKLERRHY  660
TGWGRLSAKL LVGIREKQSH LTILDYLMND DGLNRNLMQL INDSNLSFKS IIEKEQVSTT  720
DKDLQSIVAE LAGSPAIKKG ILQSLKIVDE LVSIMGYPPQ TIVVEMAREN QTTGKGKNNS  780
KPRYKSLEKA IKEFGSQILK EHPTDNQELK NNRLYLYYLQ NGKDMYTGQE LDIHNLSNYD  840
IDHIVPQSFI TDNSIDNLVL TSSAGNREKG GDVPPLEIVR KRKVFWEKLY QGNLMSKRKF  900
DYLTKAERGG LTEADKARFI HRQLVETRQI TKNVANILYQ RFNKETDNHG NTMEQVRIVT  960
LKSALVSQFR KQFQLYKVRE VNGYHHAHDA YLNGVVANTL LKVYPQLEPE FVYGEYHQFD  1020
WFKANKATAK KQFYTNIMLF FAQKERIIDE NGEILWDKKY LETIKKVLDY RQMNIVKKTE  1080
IQKGEFSKAT IKPKGNSSKL IPRKENWDPM KYGGLDSPNM AYAVIIEHAK GKKKIVIEKK  1140
LIQINIMERK MFEKDEEAFL EEKGYRHPKV LTKLPKYTLY ECEKGRRRML ASANEAQKGN  1200
QLVLSNHLVS LLYHAKNCEA SDGKSLKYIE AHRETFSELL AQVSEFATRY TLADANLSKI  1260
NNLFEQNKEG DIKAIAQSFV DLMAFNAMGA PASFKFFEAT IDRKRYTNLK ELLSSTIIYQ  1320
SITGLYESRK RLDD                                                   1334

SEQ ID NO: 208          moltype = AA  length = 1334
FEATURE                 Location/Qualifiers
source                  1..1334
                        mol_type = protein
                        organism = Listeria innocua
SEQUENCE: 208
MKKPYTIGLD IGTNSVGWAV LTDQYDLVKR KMKIAGDSEK KQIKKNFWGV RLFDEGQTAA  60
DRRMARTARR RIERRRNRIS YLQGIFAEEM SKTDANFFCR LSDSFYVDNE KRNSRHPFFA  120
TIEEEVEYHK NYPTIYHLRE ELVNSSEKAD LRLVYLALAH IIKYRGNFLI EGALDTQNTS  180
VDGIYKQFIQ TYNQVFASGI EDGSLKKLED NKDVAKILVE KVTRKEKLER ILKLYPGEKS  240
AGMFAQFISL IVGSKGNFQK PFDLIEKSDI ECAKDSYEED LESLLALIGD EYAELFVAAK  300
NAYSAVVLSS IITVAETETN AKLSASMIER FDTHEEDLGE LKAFIKLHLP KHYEEIFSNT  360
EKHGYAGYID GKTKQADFYK YMKMTLENIE GADYFIAKIE KENFLRKQRT FDNGAIPHQL  420
HLEELEAILH QQAKYYPFLK ENYDKIKSLV TFRIPYFVGP LANGQSEFAW LTRKADGEIR  480
PWNIEEKVDF GKSAVDFIEK MTNKDTYLPK ENVLPKHSLC YQKYLVYNEL TKVRYINDQG  540
KTSYFSGQEK EQIFNDLFKQ KRKVKKKDLE LFLRNMSHVE SPTIEGLEDS FNSSYSTYHD  600
LLKVGIKQEI LDNPVNTEML ENIVKILTVF EDKRMIKEQL QQFSDVLDGV VLKKLERRHY  660
TGWGRLSAKL LMGIRDKQSH LTILDYLMND DGLNRNLMQL INDSNLSFKS IIEKEQVTTA  720
DKDIQSIVAD LAGSPAIKKG ILQSLKIVDE LVSVMGYPPQ TIVVEMAREN QTTGKGKNNS  780
RPRYKSLEKA IKEFGSQILK EHPTDNQELR NNRLYLYYLQ NGKDMYTGQD LDIHNLSNYD  840
IDHIVPQSFI TDNSIDNLVL TSSAGNREKG DDVPPLEIVR KRKVFWEKLY QGNLMSKRKF  900
DYLTKAERGG LTEADKARFI HRQLVETRQI TKNVANILHQ RFNYEKDDHG NTMKQVRIVT  960
LKSALVSQFR KQFQLYKVRD VNDYHHAHDA YLNGVVANTL LKVYPQLEPE FVYGDYHQFD  1020
WFKANKATAK KQFYTNIMLF FAQKDRIIDE NGEILWDKKY LDTVKKVMSY RQMNIVKKTE  1080
IQKGEFSKAT IKPKGNSSKL IPRKTNWDPM KYGGLDSPNM AYAVVIEYAK GKNKLVFEKK  1140
IIRVTIMERK AFEKDEKAFL EEQGYRQPKV LAKLPKYTLY ECEEGRRRML ASANEAQKGN  1200
QQVLPNHLVT LLHHAANCEV SDGKSLDYIE SNREMFAELL AHVSEFAKRY TLAEANLNKI  1260
NQLFEQNKEG DIKAIAQSFV DLMAFNAMGA PASFKFFETT IERKRYNNLK ELLNSTIIYQ  1320
SITGLYESRK RLDD                                                   1334

SEQ ID NO: 209          moltype = AA  length = 132
FEATURE                 Location/Qualifiers
REGION                  1..132
                        note = Unknown bacterial, unknown viral (phage), or
                         syntheticCas9-inhibiting polypeptide
source                  1..132
                        mol_type = protein
```

-continued

```
                        organism = unidentified
SEQUENCE: 209
MGMTTARKKF YQAISEFEAM TGKDVERTPQ IADEVLNDAE YIAFTKTEKY ALYLCTSNVE  60
GLEDRYFLDE ECLDSTFLET EDNETYYIHF LQETEFSEDD NEDELPLATE EQIEAYDKQE  120
ELKAVILKKE LN                                                      132
```

CRISPR-Cas9-INHIBITING POLYPEPTIDE

CROSS REFERENCE TO RELATED PATENT APPLICATIONS

The present application is a divisional of U.S. patent application Ser. No. 16/349,253, filed May 10, 2019 (allowed); which is a U.S. National Phase Application Under 371 of PCT/US2017/061932, filed Nov. 16, 2017, which claims benefit of priority to U.S. Provisional Patent Application No. 62/422,850, filed Nov. 16, 2016, which is incorporated by referenced for all purposes.

STATEMENT AS TO RIGHTS TO INVENTIONS MADE UNDER FEDERALLY SPONSORED RESEARCH OR DEVELOPMENT

This invention was made with government support under grant no. OD021344, awarded by the National Institutes of Health. The government has certain rights in the invention.

SEQUENCE LISTING

A Sequence Listing conforming to the rules of WIPO Standard ST.26 is hereby incorporated by reference. The Sequence Listing has been filed as an electronic document via EFS-Web in ASCII format encoded as XML. The electronic document, created on Oct. 13, 2022, is entitled "2022-12-08_081906-1350802-224820US_ST26.xml", and is 296,353 bytes in size.

BACKGROUND OF THE INVENTION

The ability to prevent attack from viruses is a hallmark of cellular life. Bacteria employ multiple mechanisms to resist infection by bacterial viruses (phages), including restriction enzymes and CRISPR-Cas systems (Labrie, S. J., Samson, J. E., and Moineau, S. (2010). *Nat Rev Micro,* 8, 317-327). CRISPR arrays possess the sequence-specific remnants of previous encounters with mobile genetic elements as small spacer sequences located between their clustered regularly interspaced short palindromic repeats (Mojica, F. J. M et al. (2005). *J. Mol. Evol.,* 60, 174-182). These spacers are utilized to generate guide RNAs that facilitate the binding and cleavage of a programmed target (Brouns, S. J. J et al. (2008). *Science,* 321, 960-964; Garneau, J. E. et al. (2010). *Nature,* 468, 67-71). CRISPR-associated (cas) genes that are required for immune function are often found adjacent to the CRISPR array (Marraffini, L. A. (2015). CRISPR-Cas immunity in prokaryotes. *Nature,* 526, 55-61; Wright, A. V., Nuñez, J. K., and Doudna, J. A. (2016). *Cell,* 164, 29-44). Cas proteins not only carry out the destruction of a foreign genome (Garneau, J. E. et al. (2010). *Nature,* 468, 67-71), but also facilitate the production of mature CRISPR RNAs (crRNAs) (Deltcheva; Haurwitz, R. E et al. (2010). *Science,* 329, 1355-1358) and the acquisition of foreign sequences into the CRISPR array (Nuñez, J. K. et al. (2014). *Nat. Struct. Mol. Biol,* 21, 528-534; Yosef, I., Goren, M. G., and Qimron, U. (2012). *Nucleic Acids Research,* 40, 5569-5576).

CRISPR-Cas adaptive immune systems are common and diverse in the bacterial world. Six different types (I-VI) have been identified across bacterial genomes (Abudayyeh, O. O et al. (2016). *Science* aaf5573; Makarova, K. S. et al. (2015). *Nat Rev Micro,* 13, 722-736). *Nat Rev Micro,* 13, 722-736), with the ability to cleave target DNA or RNA sequences as specified by the RNA guide. The facile programmability of CRISPR-Cas systems has been widely exploited, opening up the door to many novel genetic technologies (Barrangou, R., and Doudna, J. A. (2016), *Nature Biotechnology,* 34, 933-941). Most of these technologies use Cas9 from *Streptococcus pyogenes* (Spy), together with an engineered single guide RNA as the foundation for such applications, including gene editing in animal cells (Cong, L. et al. (2013). *Science* 339, 819-823; Jinek, M. et al. (2012). *Science,* 337, 816-821; Mali, P. et al. (2013). *Science,* 339, 823-826; Qi, L. S. et al. (2013). *Cell,* 152, 1173-1183). Additionally, Cas9 orthologs within the II-A subtype have been investigated for gene editing applications (Ran, F. A. et al. (2015). *Nature* 520, 186-191), and new Class 2 CRISPR single protein effectors such as Cpf1 (Type V (Zetsche, B. et al. (2015). *Cell,* 163, 759-771)) and C2c2 (Type VI (Abudayyeh, O. O et al. (2016). *Science* aaf5573; East-Seletsky, A. et al. (2016). *Nature* 538, 270-273) are being characterized. Class 1 CRISPR-Cas systems (Type I, III, and IV) are RNA-guided multi-protein complexes and thus have been overlooked for most genomic applications due to their complexity. These systems are, however, the most common in nature being found in nearly half of all bacteria and ~85% of archaea (Makarova, K. S. et al. (2015). *Nat Rev Micro,* 13, 722-736). *Nat Rev Micro,* 13, 722-736).

In response to the bacterial war on phage infection, phages, in turn, often encode inhibitors of bacterial immune systems that enhance their ability to lyse their host bacterium or integrate into its genome (Samson, J. E. et al. (2013). *Nat Rev Micro,* 11, 675-687). The first examples of phage-encoded "anti-CRISPR" proteins came for the (Class 1) type I-E and I-F systems in *Pseudomonas aeruginosa* (Bondy-Denomy et al. (2013). *Nature,* 493, 429-432; Pawluk, A. et al. (2014). *mBio* 5, e00896). Remarkably, ten type I-F anti-CRISPR and four type I-E anti-CRISPR genes have been discovered to date (Pawluk, A. et al. (2016). *Nature Microbiology,* 1, 1-6), all of which encode distinct, small proteins (50-150 amino acids), previously of unknown function. Our biochemical investigation of four I-F anti-CRISPR proteins revealed that they directly interact with different Cas proteins in the multi-protein CRISPR-Cas complex to prevent either the recognition or cleavage of target DNA (Bondy-Denomy, J et al. (2015). *Nature,* 526, 136-139). Each protein has a distinct sequence, structure, and mode of action (Maxwell, K. L. et al. (2016). *Nature Communications,* 7, 13134; Wang, X. (2016). *Nat. Struct. Mol. Biol* 23, 868-870). These findings support the independent evolution of CRISPR-Cas inhibitors and suggests that many more are yet to be discovered. In this light, a recent paper utilized the conservation of signature anti-CRISPR associated (aca) gene with a predicted helix-turn-helix (HTH) motif to identify anti-CRISPR genes outside of *P. aeruginosa*. This led to the authors finding anti-CRISPRs across proteobacteria, broadly spanning the type I-F CRISPR-Cas phylogeny (Pawluk, A. et al. (2016). *Nature Microbiology,* 1, 1-6). This suggests that anti-CRISPRs may exist for all CRISPR systems, with methods needed to enable their discovery.

The type I anti-CRISPRs in *P. aeruginosa* are expressed from integrated phage genomes (prophages), leading to the constitutive inactivation of the host CRISPR-Cas system (Bondy-Denomy et al. (2013). *Nature,* 493, 429-432. This can often lead to a situation where a prophage possesses a DNA target with perfect identity to a co-occurring CRISPR spacer in the same cell, called "self-targeting" (FIG. 1A). This situation makes CRISPR-Cas inactivation a requirement for survival, as in the absence of prophage anti-CRISPR genes, the host genome is cleaved in the act of targeting the prophage (Bondy-Denomy et al. (2013). *Nature,* 493, 429-432; Edgar, R., and Qimron, U. (2010). *J.*

*Bacteriol* 192, 6291-6294). Expression of an anti-CRISPR neutralizes this risk, however, allowing lysogen survival. We surmised that genomes possessing a CRISPR system with apparent self-targeting would be candidates for the identification of new CRISPR-Cas inhibitors. Here, we describe the identification of previously unknown phage-encoded CRISPR-Cas9 inhibitors in *Listeria monocytogenes* using a bioinformatics approach to identify incidents of self-targeting. We show that two of these inhibitors can also block the activity of *S. pyogenes* Cas9 in bacterial and human cells.

Definitions

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term "gene" means the segment of DNA involved in producing a polypeptide chain. It may include regions preceding and following the coding region (leader and trailer) as well as intervening sequences (introns) between individual coding segments (exons).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. The promoter can be a heterologous promoter.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. The promoter can be a heterologous promoter. In the context of promoters operably linked to a polynucleotide, a "heterologous promoter" refers to a promoter that would not be so operably linked to the same polynucleotide as found in a product of nature (e.g., in a wild-type organism).

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. In some cases, conservatively modified variants of Cas9 or sgRNA can have an increased stability, assembly, or activity as described herein.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or specified subsequences that are the same. Two sequences that are "substantially identical" have at least 60% identity, preferably 65%, 70%, 75%, 80%, 85%, 90%, 91%, 92%, 93, 94%, 95%, 96%, 97%, 98%, 99%, or 100% identity, when compared and aligned for maximum correspondence over a comparison window, or designated region as measured using a sequence comparison algorithm or by manual alignment and visual inspection where a specific region is not designated. With regard to polynucleotide sequences, this definition also refers to the complement of a test sequence. With regard to amino acid sequences, in some cases, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST 2.0 algorithm and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

An algorithm for determining percent sequence identity and sequence similarity is the BLAST 2.0 algorithm, which are described in Altschul et al., (1990) J. Mol. Biol. 215: 403-410. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The "CRISPR/Cas" system refers to a class of bacterial systems for defense against foreign nucleic acid. CRISPR/Cas systems are found in a wide range of eubacterial and archaeal organisms. CRISPR/Cas systems include type I, II, III, V, and VI sub-types. Wild-type type II CRISPR/Cas systems utilize the RNA-mediated nuclease, Cas9 in complex with guide and activating RNA to recognize and cleave foreign nucleic acid.

Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 polypeptide is the *Streptococcus pyogenes* Cas9 polypeptide. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21. The Cas9 protein can be nuclease defective. For example, the Cas9 protein can be a nicking endonuclease that nicks target DNA, but does not cause double strand breakage. Cas9 can also have both nuclease domains deactivated to generate "dead Cas9" (dCas9), a programmable DNA-binding protein with no nuclease activity. In some embodiments, dCas9 DNA-binding is inhibited by the polypeptides described herein.

BRIEF SUMMARY OF THE INVENTION

In one aspect, methods of inhibiting a Cas9 polypeptide in a cell are provided. In some embodiments, the method comprises, introducing a Cas9-inhibiting polypeptide into a cell, wherein: the Cas9-inhibiting polypeptide is heterologous to the cell, and the Cas9-inhibiting polypeptide is substantially (e.g., at least 60%, 70%, 80%, 90%, 95%) identical to any one or more of SEQ ID NO: 1-170, thereby inhibiting the Cas9 polypeptide in a cell. In some embodiments, the method comprises contacting the Cas9 inhibiting polypeptide with a Cas9 polypeptide in the cell. In some embodiments, the method comprises contacting the Cas9 inhibiting polypeptide with other components of the CRISPR-Cas9 system in the cell, thereby indirectly inhibiting Cas9 polypeptide activity.

In some embodiments, the Cas9-inhibiting polypeptide comprises one of SEQ ID NO: 1-170.

In some embodiments, the cell comprises the Cas9 polypeptide before the introducing. In some embodiments, the cell comprises an expression cassette comprising a promoter operably linked to a polynucleotide encoding the Cas9 polypeptide. In some embodiments, the promoter is inducible and the method comprises contacting the cell with an agent or condition that induces expression of the Cas9 polypeptide in the cell prior to the introducing.

In some embodiments, the cell comprises the Cas9 polypeptide after the introducing. In some embodiments, the promoter is inducible and the method comprises contacting the cell with an agent or condition that induces expression of the Cas9 polypeptide in the cell after to the introducing.

In some embodiments, the introducing comprises expressing the Cas9-inhibiting polypeptide in the cell from an expression cassette that is present in the cell and heterologous to the cell, wherein the expression cassette comprises a promoter operably linked to a polynucleotide encoding the Cas9-inhibiting polypeptide. In some embodiments, the promoter is an inducible promoter and the introducing comprises contacting the cell with an agent that induces expression of the Cas9-inhibiting polypeptide.

In some embodiments, the introducing comprises introducing an RNA encoding the Cas9-inhibiting polypeptide into the cell and expressing the Cas9-inhibiting polypeptide in the cell from the RNA.

In some embodiments, the introducing comprises inserting the Cas9-inhibiting polypeptide into the cell or contacting the cell with the Cas9-inhibiting polypeptide.

In some embodiments, the cell is a eukaryotic cell. In some embodiments, the cell is a mammalian cell. In some embodiments, the cell is a human cell. In some embodiments, the cell is a blood or an induced pluripotent stem cell. In some embodiments, the cell is a prokaryotic cell.

In some embodiments, the method occurs ex vivo. In some embodiments, the cells are introduced into a mammal after the introducing and contacting. In some embodiments, the cells are autologous to the mammal.

Also provided is a cell (optionally isolated) comprising a Cas9-inhibiting polypeptide, wherein the Cas9-inhibiting polypeptide is heterologous to the cell and the Cas9-inhibiting polypeptide is substantially identical to any one or more of SEQ ID NO: 1-170. In some embodiments, the cell is a eukaryotic cell. In some embodiments, the cell is a mammalian cell. In some embodiments, the cell is a human cell In some embodiments, the cell is a prokaryotic cell.

Also provided is a polynucleotide comprising a nucleic acid encoding a Cas9-inhibiting polypeptide. In some embodiments, the Cas9-inhibiting polypeptide is substantially identical to any one or more of SEQ ID NO: 1-170. In some embodiments, the polynucleotide comprises an expression cassette, the expression cassette comprising a promoter operably linked to the nucleic acid. In some embodiments, the promoter is heterologous to the polynucleotide encoding the Cas9-inhibiting polypeptide. In some embodiments, the promoter is inducible. In some embodiments, the polynucleotide is DNA or RNA.

Also provided is a vector comprising the expression cassette as described above or elsewhere herein. In some embodiments, the vector is a viral vector.

Also provided is a (optionally isolated) Cas9-inhibiting polypeptide. In some embodiments, the Cas9-inhibiting polypeptide is substantially identical to any one or more of SEQ ID NO:1-170.

Also provided is a pharmaceutical composition comprising the polynucleotide or the polypeptide as described above or elsewhere herein.

Also provided is a delivery vehicle comprising the polynucleotide or the polypeptide as described above or elsewhere herein. In some embodiments, the delivery vehicle is a liposome or nanoparticle.

Other aspects are described in the remainder of this document.

BRIEF DESCRIPTION OF THE DRAWINGS

FIG. 1A-C. A survey for CRISPR-Cas9 genomic self-targeting (ST) in *Listeria monocytogenes.*

FIG. 1A A schematic depicting the principle of genomic self-targeting, where a mobile genetic element (MGE) possesses a target sequence for a spacer in a CRISPR array in the same genome. CRISPR-Cas9 function in this "self-targeting genome" is presumably inactive for continued cell viability.

FIG. 1B The abundance of genomes with cas9-linked self-targeting (red) and those without ST (grey), in *L. monocytogenes* genomes.

FIG. 1C An example of an ST event, where spacer 16 in the CRISPR array of strain J0161 has a perfect PAM and protospacer match with a resident prophage (ϕJ0161 (spacer sequences: crRNA (SEQ ID NO:171), protospacer and protospacer complement (SEQ ID NOS:172-173)).

FIG. 2A The type II-A CRISPR-Cas locus in *L. monocytogenes* 10403s. Four cas genes are indicated, along with tracrRNA and CRISPR array, containing 30 spacers. The predicted direction of transcription is indicated with black arrows. Subsequent experiments utilize a non-targeted plasmid (pNT) and a targeted plasmid (pT) that has a protospacer matching spacer 1 in this strain.

FIG. 2B Representative pictures of transformed colonies after CRISPR-Cas-targeted (pT) or non-targeted (pNT) plasmids were electroporated into phage-cured (ϕcure) strains of *L. monocytogenes* 10403s and wild type (wt) J0161 (contains the ϕJ0161a prophage) is shown in red to denote self-targeting. Analyzed ϕcure 10403s variants include a cas9-deletion strain (Δcas9), a lysogen of ϕJ0161a (::ϕJ0161a), strains constitutively expressing individual CRISPR-Cas9 inhibitor genes from ϕJ0161a (+acrIIA1, +acrIIA2) and a lysogen of ϕJ0161a with CRISPR-Cas9 inhibitor genes deleted (:: ϕJ0161aΔacrIIA1-2). See FIG. 7 for a comparison of wt and ϕcure 10403s.

FIG. 2C 10403s ϕcure and wt J0161 strains were assessed for transformation efficiency. The 10403s ϕcure cas9-deletion strain (Δcas9), constitutively expressed cas9 (Δcas9+cas9) and ϕJ0161a lysogens of these strains (::ϕJ0161a) were analyzed. Error bars reflect the standard deviation of three biological replicates. L.D. limit of detection.

FIG. 2D Comparison of the open reading frames from two similar prophages from *L. monocytogenes* 10403s and J0161. Unique genes (red) comprising ten fragments of ϕJ0161 were tested for CRISPR-Cas9 inhibition in 10403s. n.e., No effect on CRISPR-Cas9 activity, tox., fragment toxic when expressed, t., location of self-targeted protospacer. The encircled fragment exhibited anti-CRISPR activity with two genes (acrAII1, acrAII2) independently capable of inhibiting CRISPR-Cas activity. Conserved (grey) genes were not tested. For reference, phage genes involved in cell lysis, capsid assembly and host integration (int.) are labeled.

FIG. 3A-C. Genomic organization and prevalence of acrIIA genes

FIG. 3A The genomic context of acrIIA1 (1) and its homolog from *L. monocytogenes* (orfD) are depicted to scale as cartoons with acrIIA1 homologs in vertical alignment. Typically, acrIIA genes are encoded within prophages adjacent to or near the phage lysin (ply) gene. Genomic neighbors of acrIIA1 and orfD (acrIIA1-4, orfA-E) are shown. Individual genes (***) were assayed for CRISPR-Cas9 inhibition in *L. monocytogenes* 10403s (see FIG. 9). Helix-turn-helix (HTH) and AP2 DNA binding motifs were detected in some proteins using hidden markov model (HMM) prediction software (Söding, J., Biegert, A., and Lupas, A. N. (2005). *Nucleic Acids Research,* 33, W244-W248).

FIG. 3B Pie-graph representation of the frequency of each acrIIA gene co-occurrences FIG. 3C Pie-graph representation of the prevalence of acrIIA and cas9 genes in the *L. monocytogenes* pan-genome. See Supplementary Table 1 for relevant accession numbers.

A phylogenetic reconstruction of full-length protein sequences identified following an iterative psi-BLASTp search to query all non-redundant protein sequences within GenBank for (FIG. 4A) AcrIIA1.

Figures 4A, 4B, 4C, 4D:
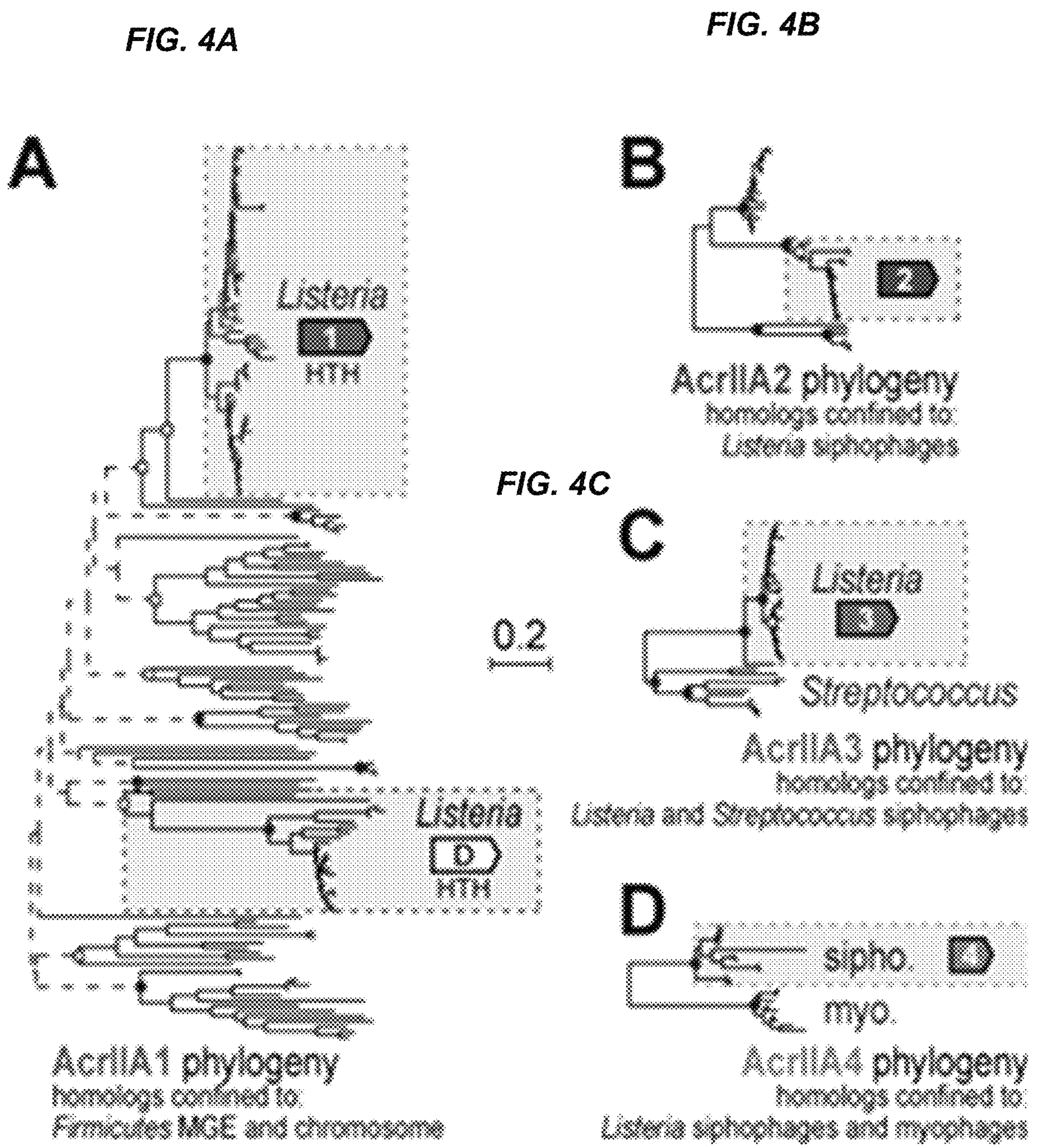
FIG. 4A. Phylogenetic analysis of AcrIIA1-4 homologs

BLASTp was used to construct a similar tree for (FIG. 4B) AcrIIA2, (FIG. 4C) AcrIIA3, and FIG. 4D AcrIIA4 (see Methods). Selected bootstrapping support values are denoted with filled ovals (≥90%), open rectangles (≥70%) or dashed lines (<70%). The sequence family that is boxed-in represents the family that was tested for anti-CRISPR function. Other homologs reflect distinct sequence families present in the genomes described under the tree.

FIG. 5A-D. Inhibition of *Streptococcus pyogenes* dCas9 and Cas9.

Figures 5A, 5B, 5C, 5D:
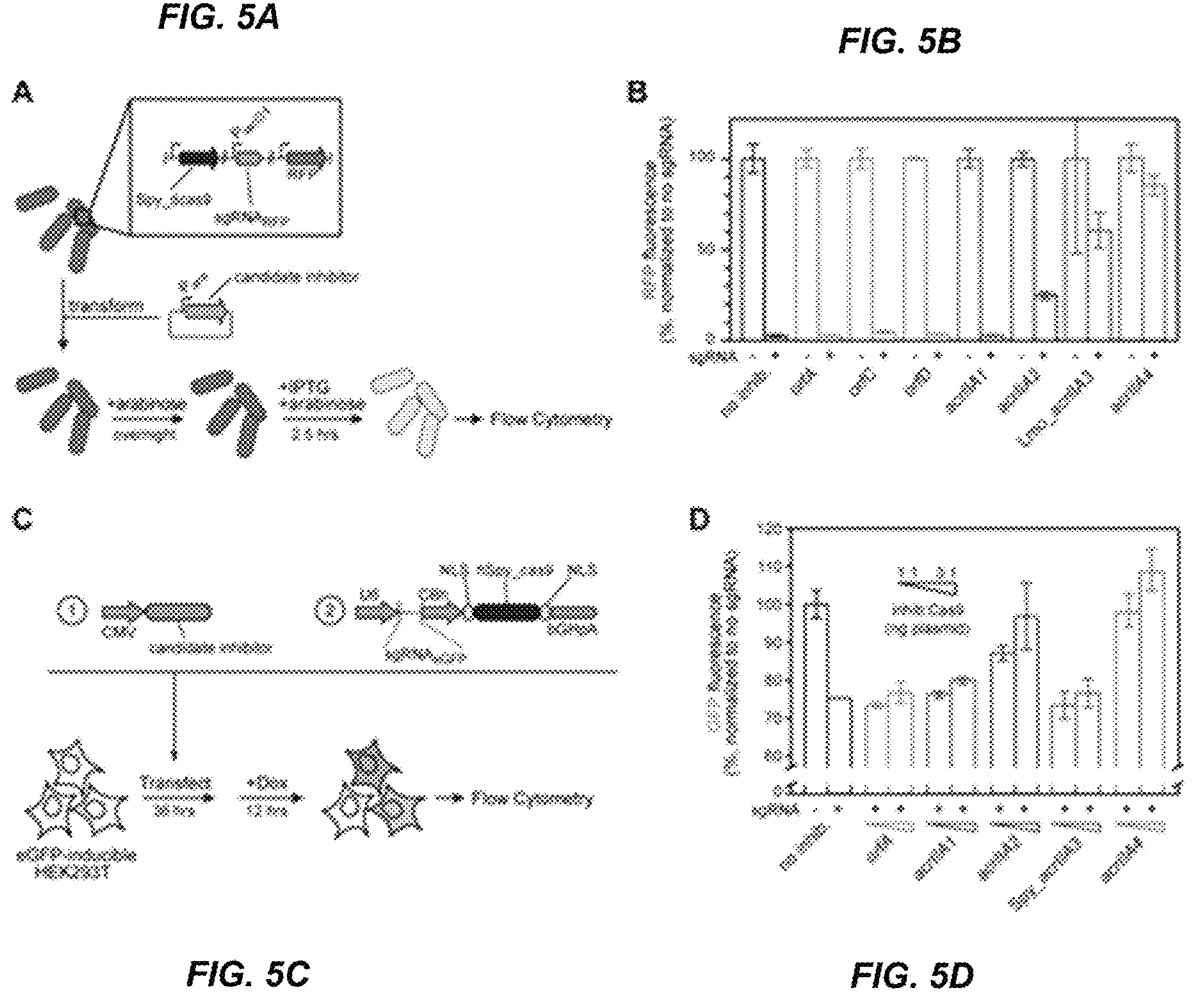

FIG. 5A A schematic outlining the experimental setup, where single-cell fluorescence of *E. coli* BW25113 with *Streptococcus pyogenes* (Spy) dCas9 and a guide RNA targeted towards a chromosomal red fluorescent protein (RFP) gene was measured.

FIG. 5B Candidate (orf) and validated (acr) acrIIA genes were tested for their ability to inhibit dCas9-based repression. Measurements taken reflect the median RFP fluorescence value of a single cell in a unimodal population normalized for each candidate gene to a guide RNA-free control. Error bars represent the standard deviation of at least three biological replicates. See FIG. 2 and FIG. 9 for gene-identification information.

FIG. 5C A schematic outlining the experimental setup, where HEK293T cells with a doxycycline-inducible eGFP cassette were transfected with a plasmid encoding a single transcript tracrRNA/eGFP-targeting guide RNA and NLS-SpyCas9 alongside expression constructs encoding one of five codon-optimized phage genes at different ratios. The percent of eGFP positive cells was measured 12 hours after induction by flow cytometry.

FIG. 5D Average percent of eGFP positive cells is depicted+/−standard deviation across biological triplicates. An increasing amount of inhibitor plasmid (in ng) was added from left to right, at a ratio to the Cas9/sgRNA plasmid of 1:1 and 3:1. Data were normalized to transfection with no phage ORF as the baseline.

Figure 6:
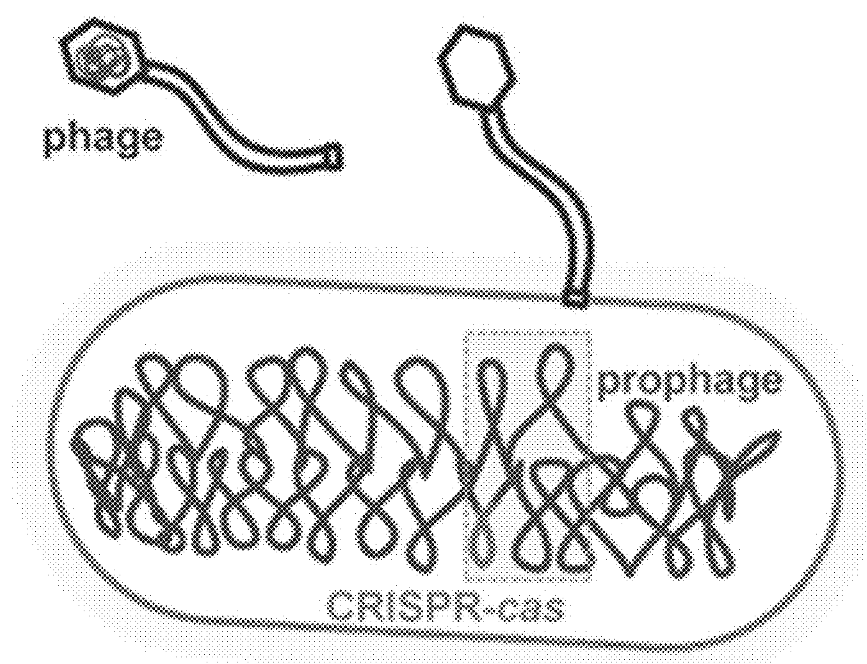
Figure 6:
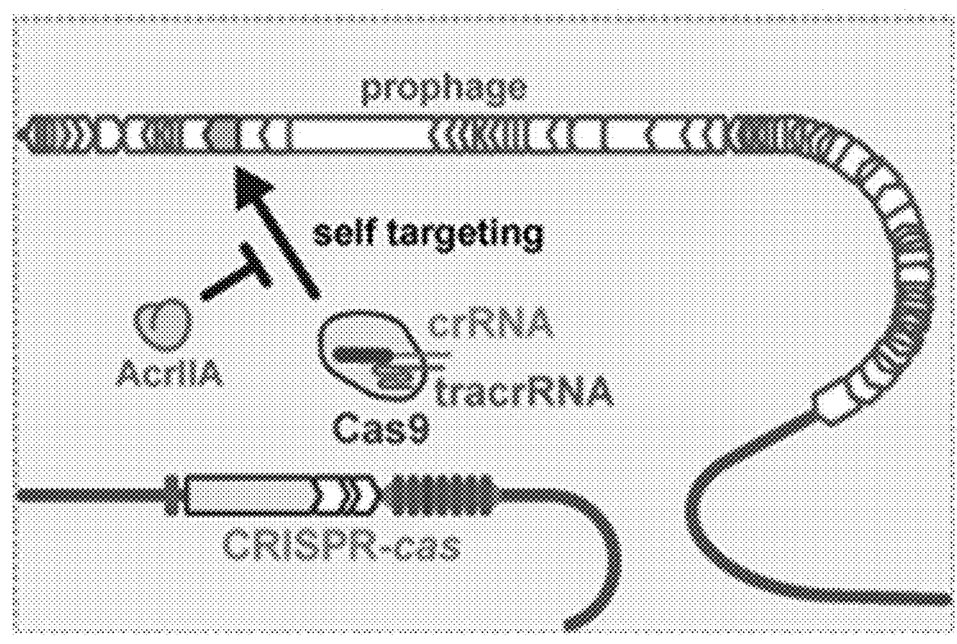

FIG. 6 is a cartoon depiction of AcrIIA-inhibition of Cas9.

FIG. 7A-F. Self-Targeting by CRISPR-Cas9 in *Listeria monocytogenes* J0161 is Not Associated with Loss-of-Function Mutations, Related to FIG. 1

Figures 7A, 7B, 7C, 7D:
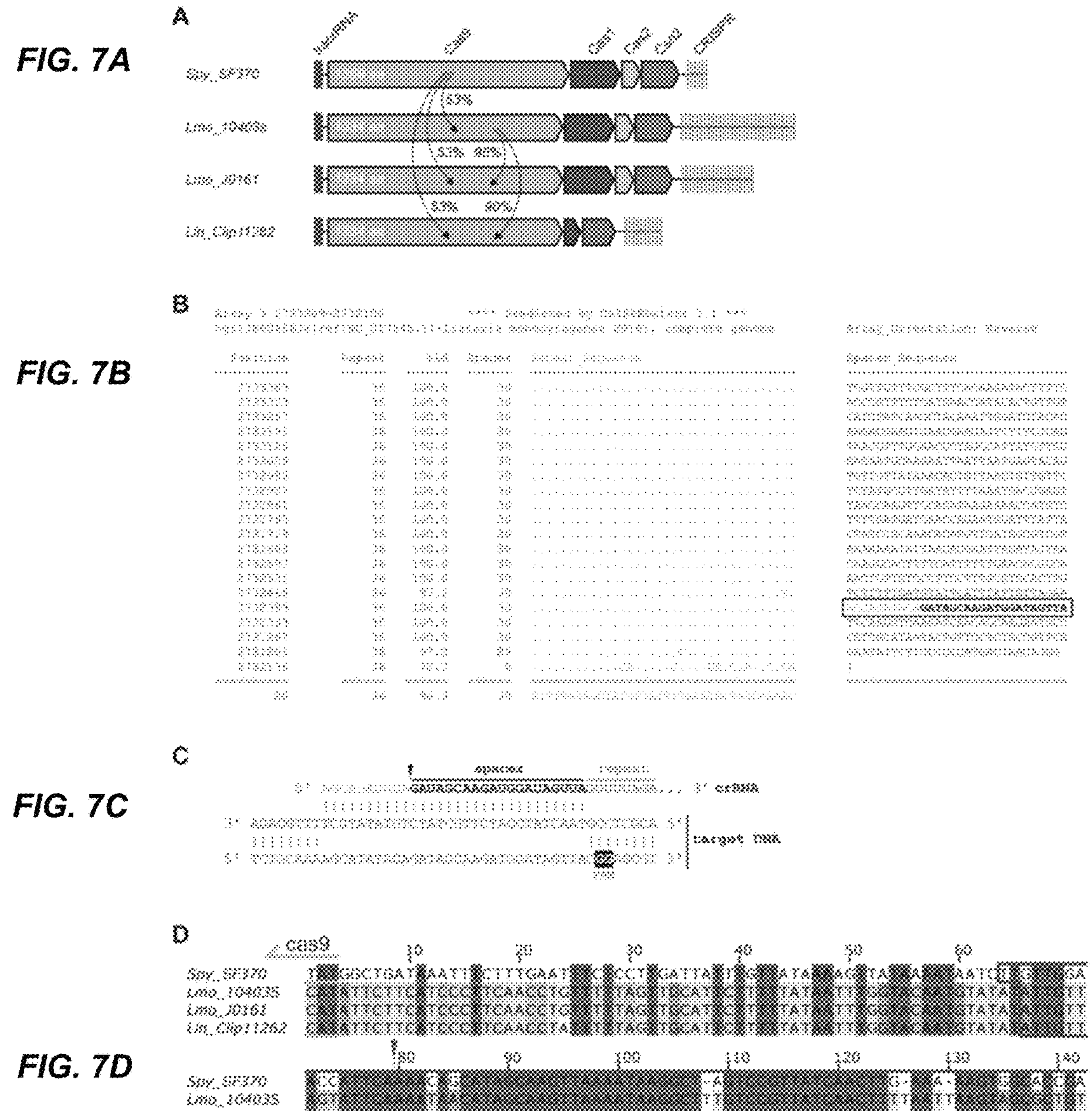

FIG. 7A Comparison of type II-A CRISPR-cas loci from *Streptococcus pyogenes* SF370 (Spy_SF370), *Listeria monocytogenes* 10403s (Lmo_10403s), *Listeria monocytogenes* J0161 (Lmo_J0161) and *Listeria innocua* (Lin_Clip11262). Percent identity between Cas9 protein sequences is shown.

FIG. 7B The CRISPR array of self-targeting strain Lmo J0161. A type II-A CRISPR array, predicted by the CRISPRDetect web utility is shown (Spacer Sequence: SEQ ID NOS:174-192, respectively; Repeat Sequence: SEQ ID NO:193). The self-targeting spacer (number 16 (SEQ ID NO:189) is boxed. In bold, are the RNA-coding nucleotides responsible for target recognition.

FIG. 7C A modified CRISPRtarget output, depicting self-targeting by *L. monocytogenes* J0161. The predicted crRNA processing site is identified by the wedge icon. (sequences: crRNA (SEQ ID NO:194), target DNA and target DNA complement (SEQ ID NOS:195-196)).

FIG. 7D Alignment of tracrRNA loci. (Spy_SF370 (SEQ ID NO:197); Lmo_10403s (SEQ ID NO:198); Lmo_J0161 (SEQ ID NO:199): Lin_Clip11262 (SEQ ID NO:200).

Figures 7E, 7F:
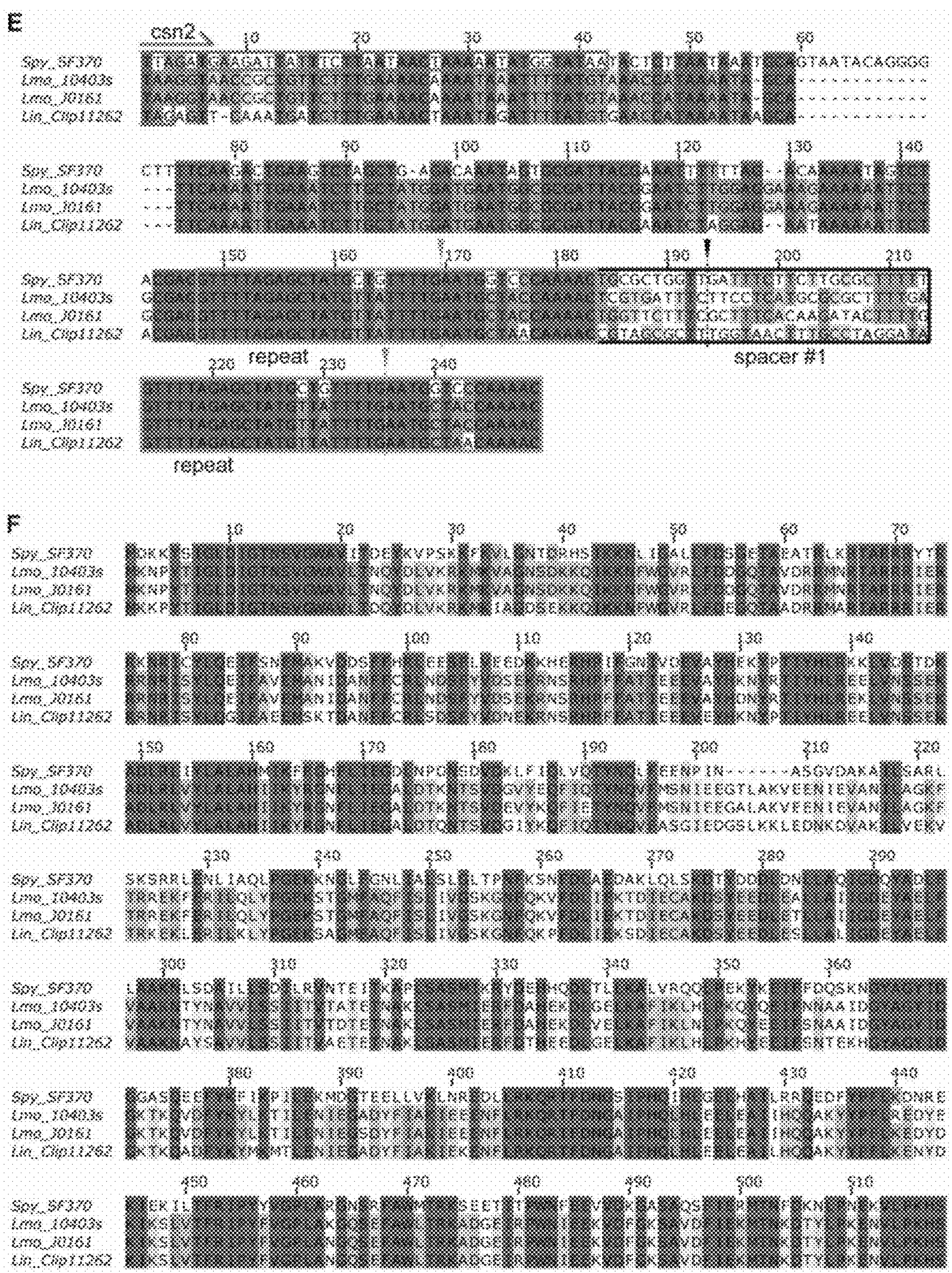
Figure 7F:
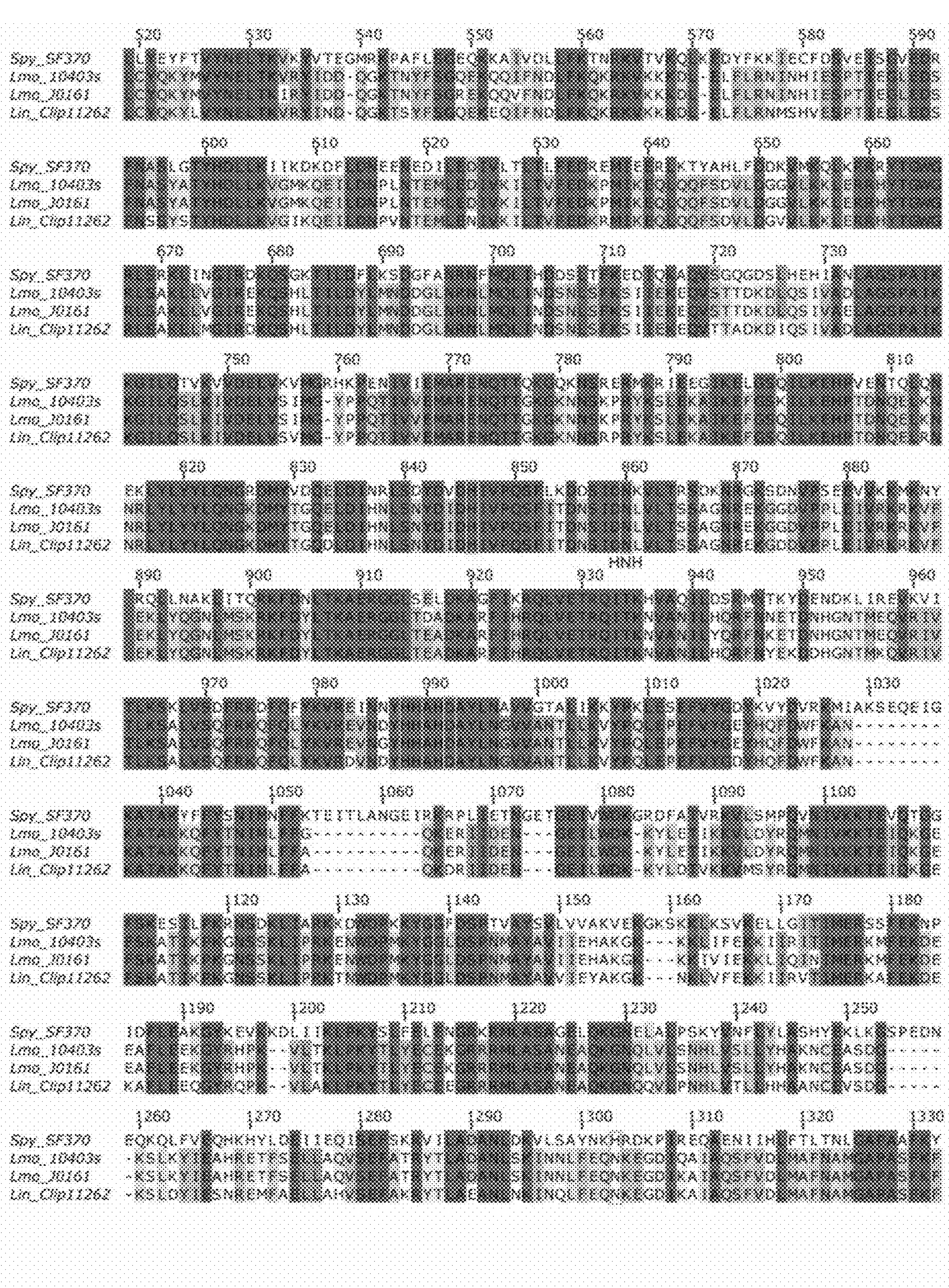
Figure 7F:
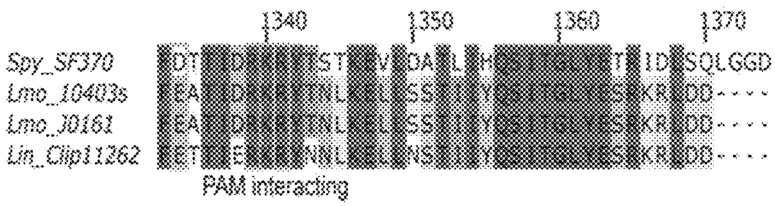

FIG. 7E Alignment of CRISPR loci. (Spy_SF370 (SEQ ID NO:201); Lmo_10403s (SEQ ID NO:202); Lmo_J0161 (SEQ ID NO:203): Lin_Clip11262 (SEQ ID NO:204).

FIG. 7F Alignment of Cas9 protein sequences. Residues with essential chemical functionalities are boxed. (Spy_SF370 (SEQ ID NO:205); Lmo_10403s (SEQ ID NO:206); Lmo_J0161 (SEQ ID NO:207): Lin_Clip11262 (SEQ ID NO:208).

Figure 8:
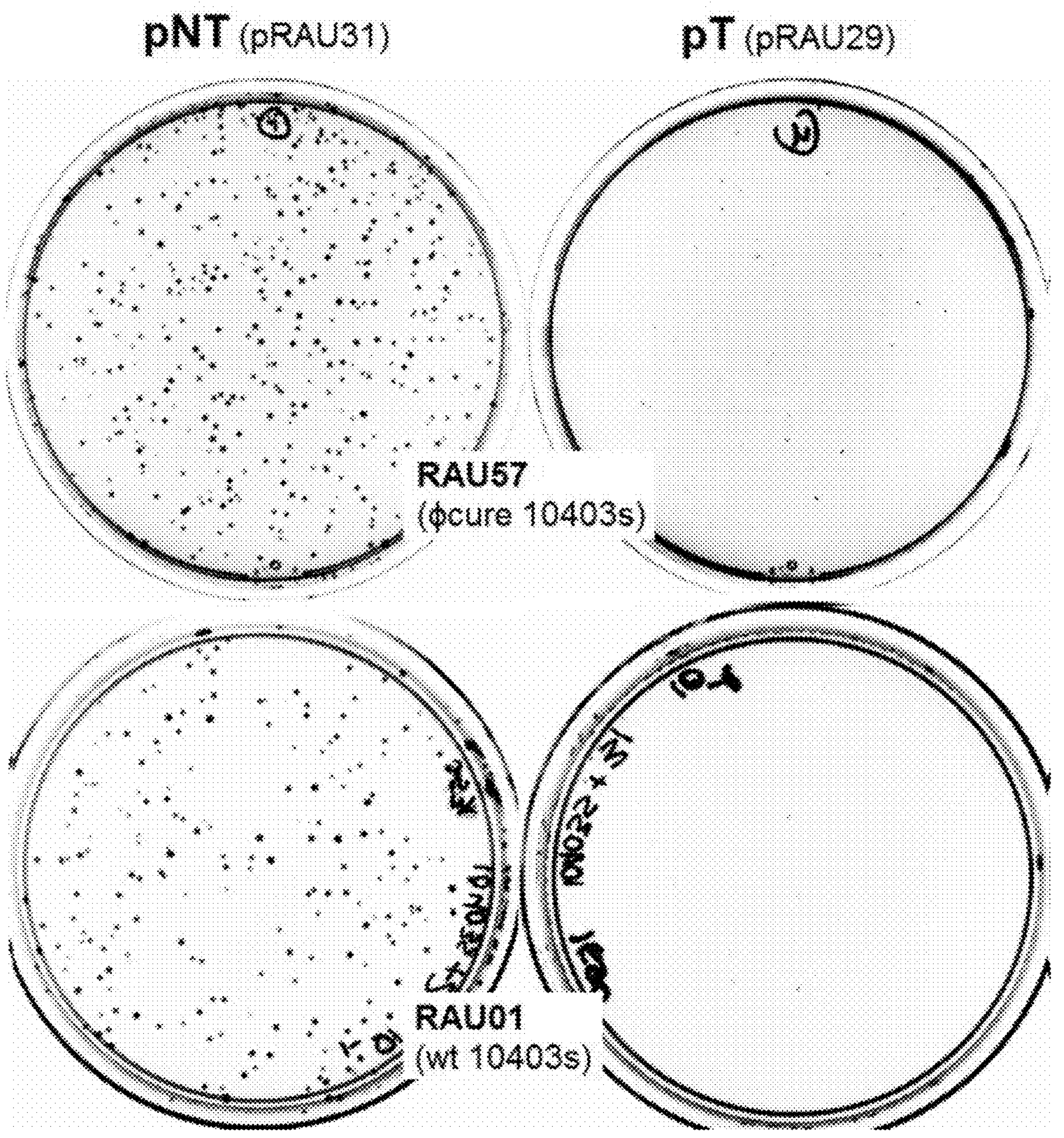

FIG. 8. The ϕ10403s Prophage Does Not Influence Plasmid Targeting in *L. monocytogenes* 10403s, Related to FIG. 2A-D. Representative plates depicting colonies after transformation and selection for targeted (pT; pRAU31) or non-targeted (pNT; pRAU29) plasmids. Wild type (wt) and nonlysogenic (ϕcure) strains of 10403s were analyzed. See Table S1 for additional information pertinent to plasmid and strain design and nomenclature.

Figure 9:
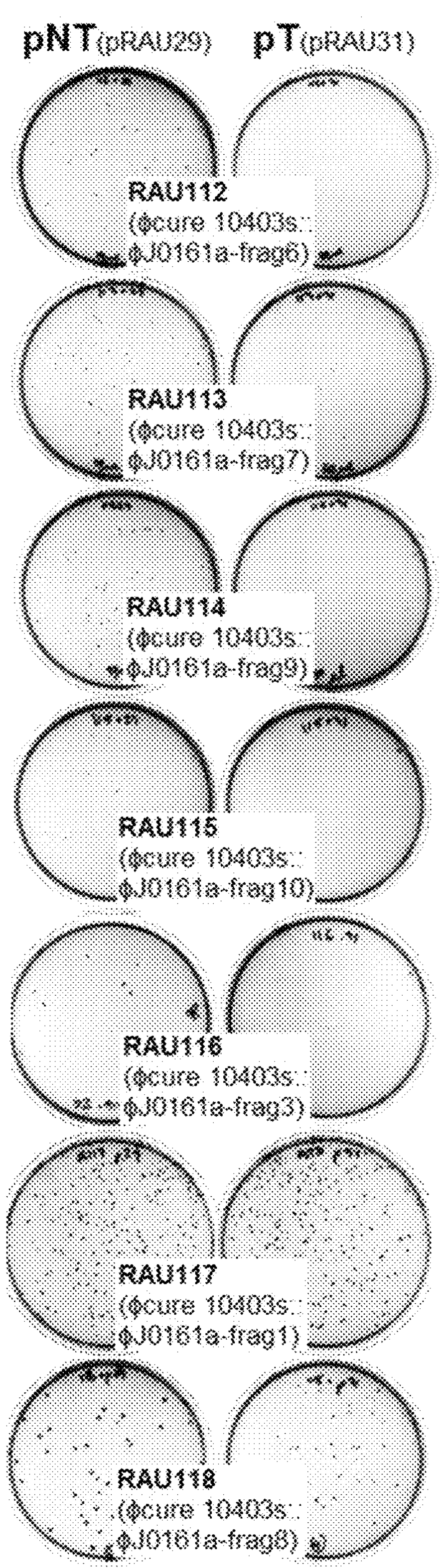

FIG. 9. Fragments of the ϕJ0161a Prophage that were Screened for CRISPR-Cas9 Inhibition Activity in *L. monocytogenes* 10403s, Related to FIG. 2. Representative plates depicting colonies after transformation and selection for targeted (pT; pRAU31) or non-targeted (pNT; pRAU29) plasmids. DNA sequence information is provided for all phage fragments as they are named in FIG. 2*d*. See Table 51 for additional information pertinent to plasmid and strain design and nomenclature.

Figure 10A:
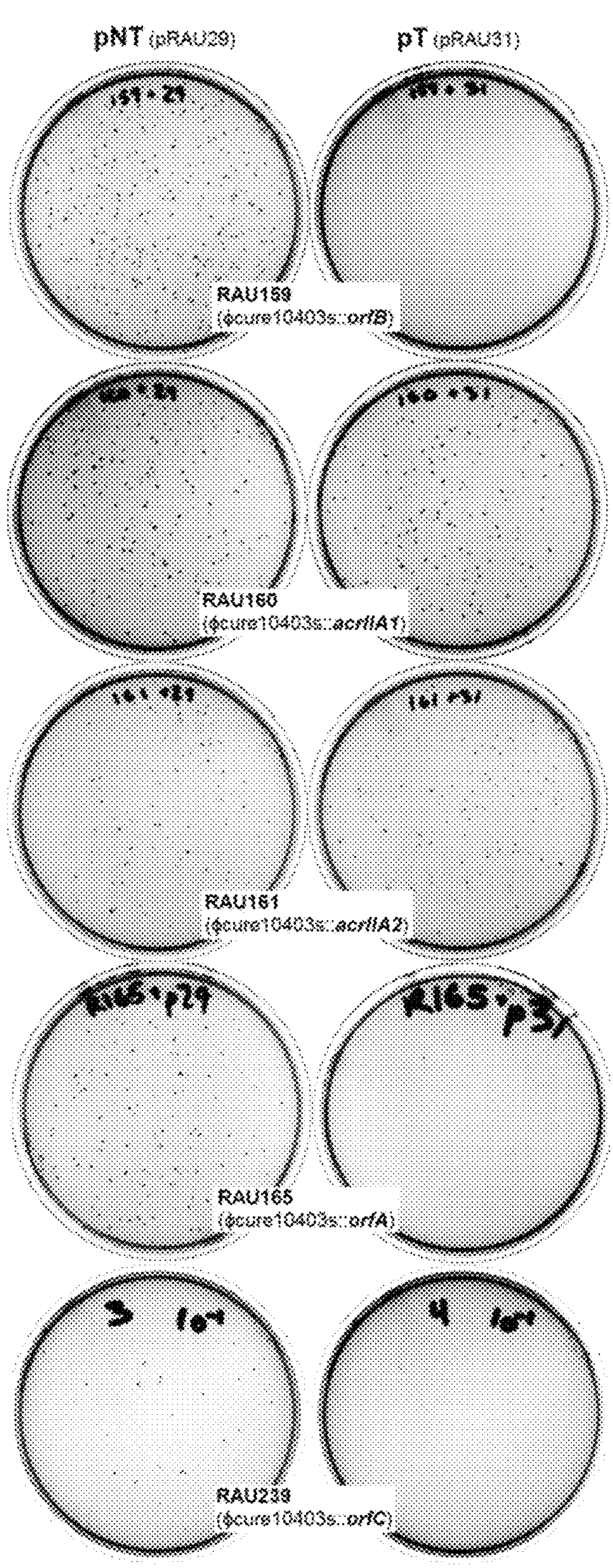
Figure 10B:
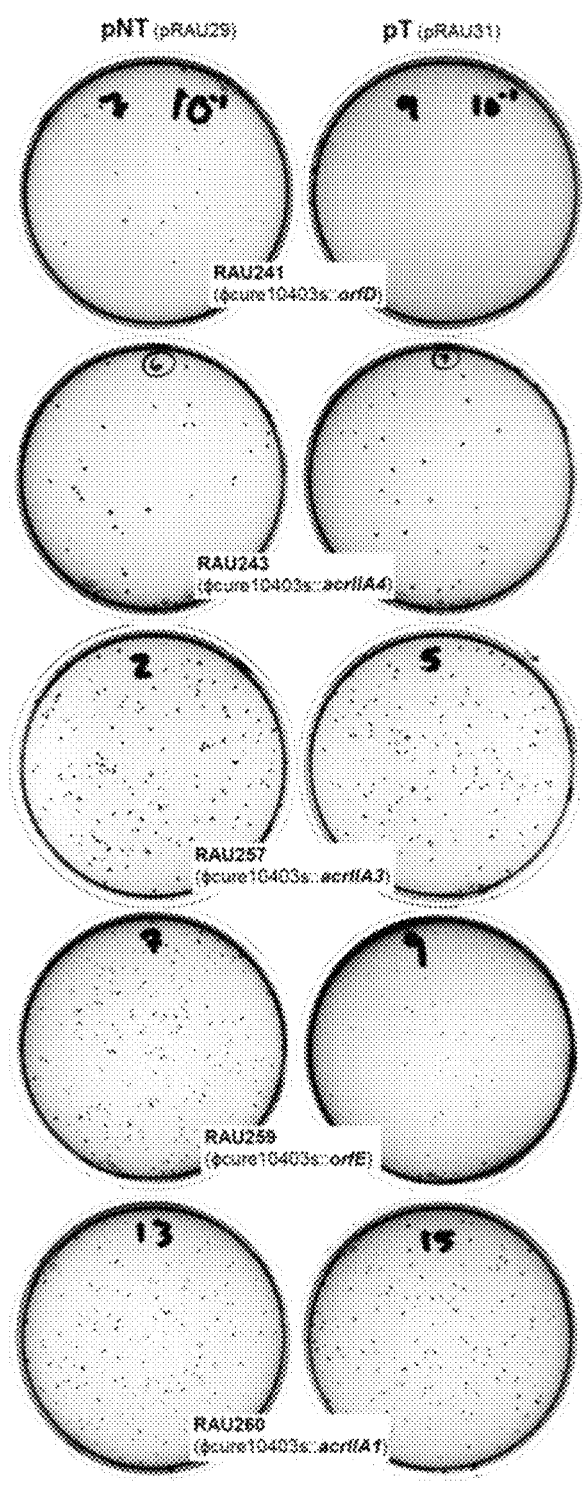

FIG. 10A-B. Individual Genes that were Screened for CRISPR-Cas9 Inhibition Activity in *L. monocytogenes* 10403s, Related to FIG. 2B and FIG. 3A. Representative plates depicting colonies after transformation and selection for targeted (pT; pRAU31) or non-targeted (pNT; pRAU29) plasmids. Given names, locus tags, accession numbers and DNA sequence information is provided for all candidate type II-A CRISPR-Cas inhibitors. See Table S1 for additional information pertinent to plasmid and strain design and nomenclature.

Figures 11A, 11B:
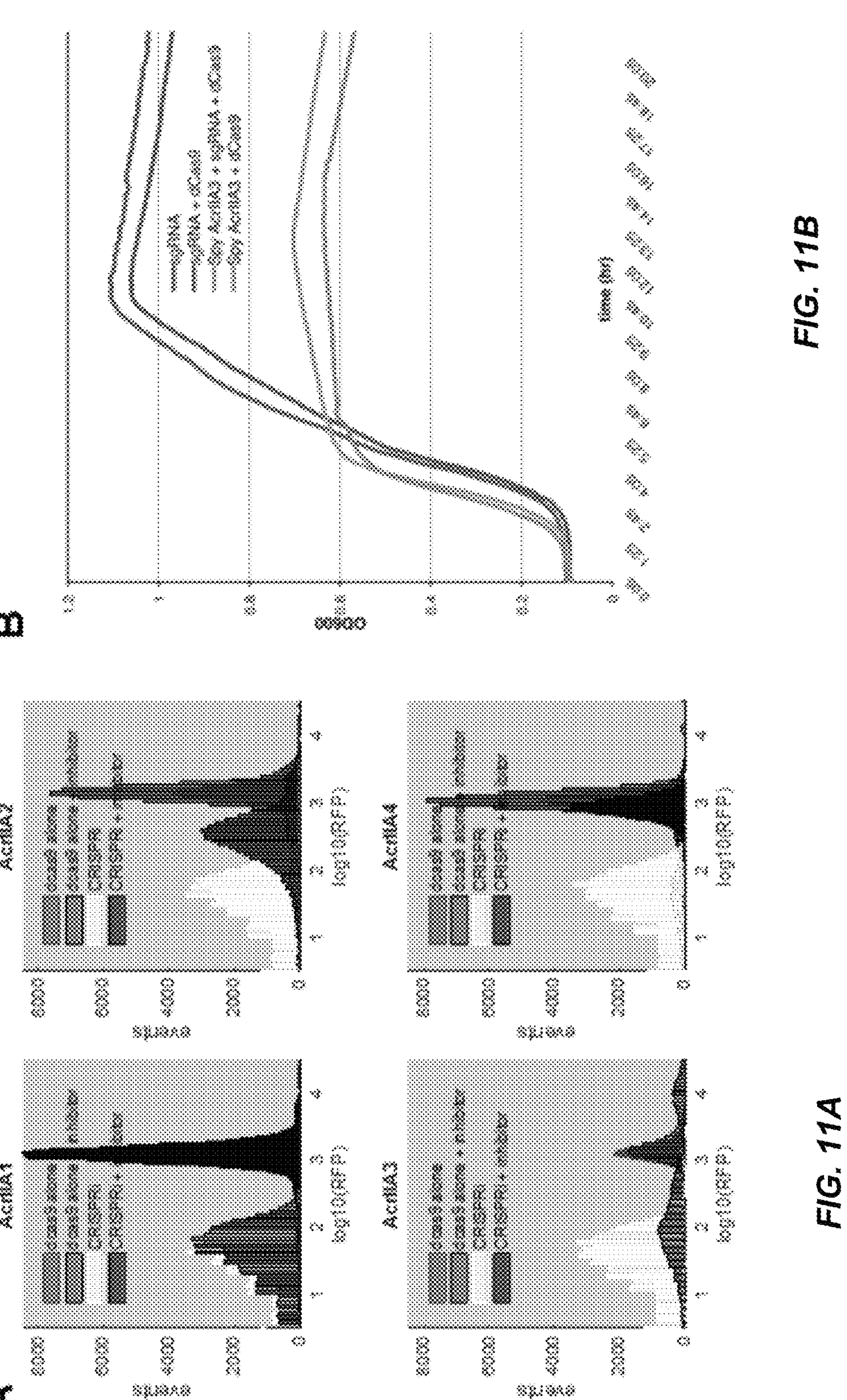

FIG. 11A-B. Toxicity of an AcrIIA3 Homolog from *S. pyogenes* in *E. coli*, Related to FIG. 5.

FIG. 11A Distribution of single-cell RFP fluorescence values for *E. coli* CRISPRi reporter strains with and without expression of AcrIIA proteins. Expression of AcrIIA proteins leads to unimodal shift in population fluorescence towards the sgRNA (no CRISPRi knockdown) state, indicating a uniform disruption of CRISPRi activity. Strains were grown for 2.5 hr in the presence of IPTG to induce CRISPRi, with or without expression of the AcrIIA inhibitor.

FIG. 11B Expression of Spy AcrIIA3 is toxic in *E. coli*. In the presence of IPTG (CRISPRi induction) and arabinose (AcrIIA3 induction), Spy AcrIIA3 is toxic in the presence or absence of sgRNA, indicating that its toxicity is independent of CRISPRi activity.

Figure 12:
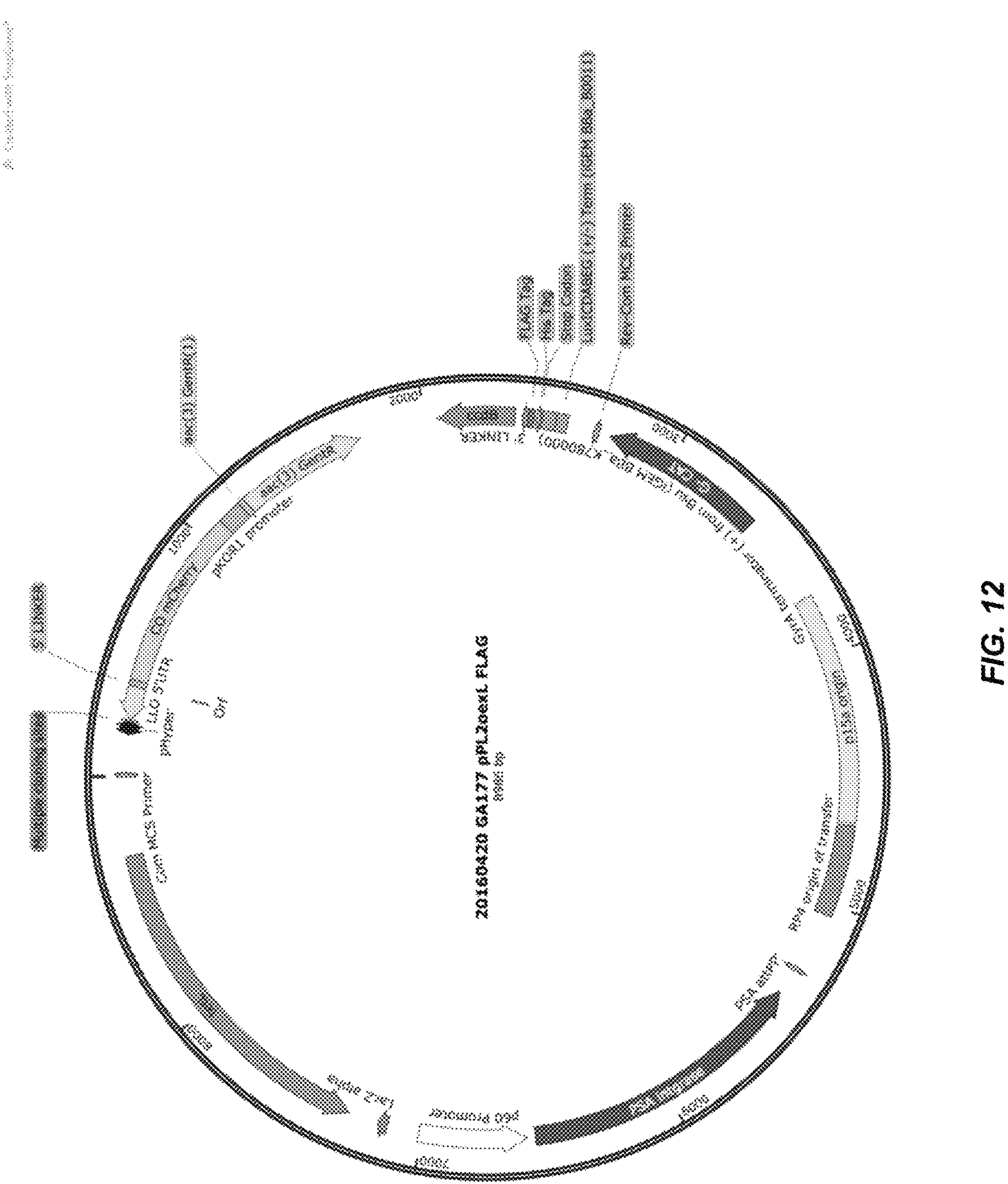

FIG. 12. Vector Map file for pPL2oexL, Related to FIG. 2 and FIG. 3. Genes and phage fragments to be tested for CRISPR-Cas9 inhibition in *L. monocytogenes* 10403s were cloned into pPL2oexL between pHyper and the FLAG tag. Native stop codons were included in pPL2oexL derivatives.

Figure 13:
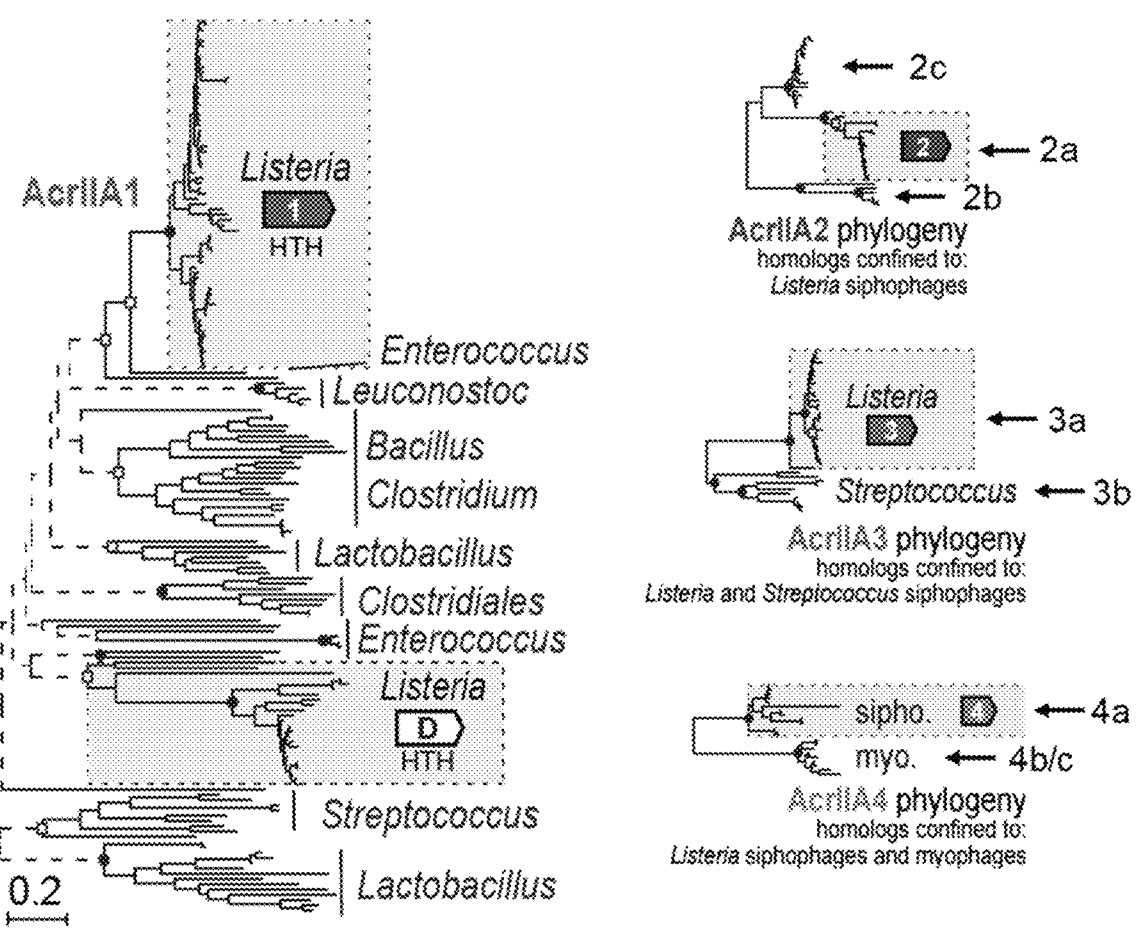

FIG. 13: acrIIA1 is very widespread across Firmicutes homologs are likely to inhibit Cas9 function in the organisms in which they are found. To identify new homologs of acrIIA genes with anti-CRISPR function, distinct members from the phylogenetic trees shown here were tested for anti-CRISPR activity in cell based assays. These homologs of known anti-CRISPR genes are being tested in a foreign bacterial system (*Pseudomonas aeruginosa*) to identify those with direct activity against SpyCas9.

Figure 14:
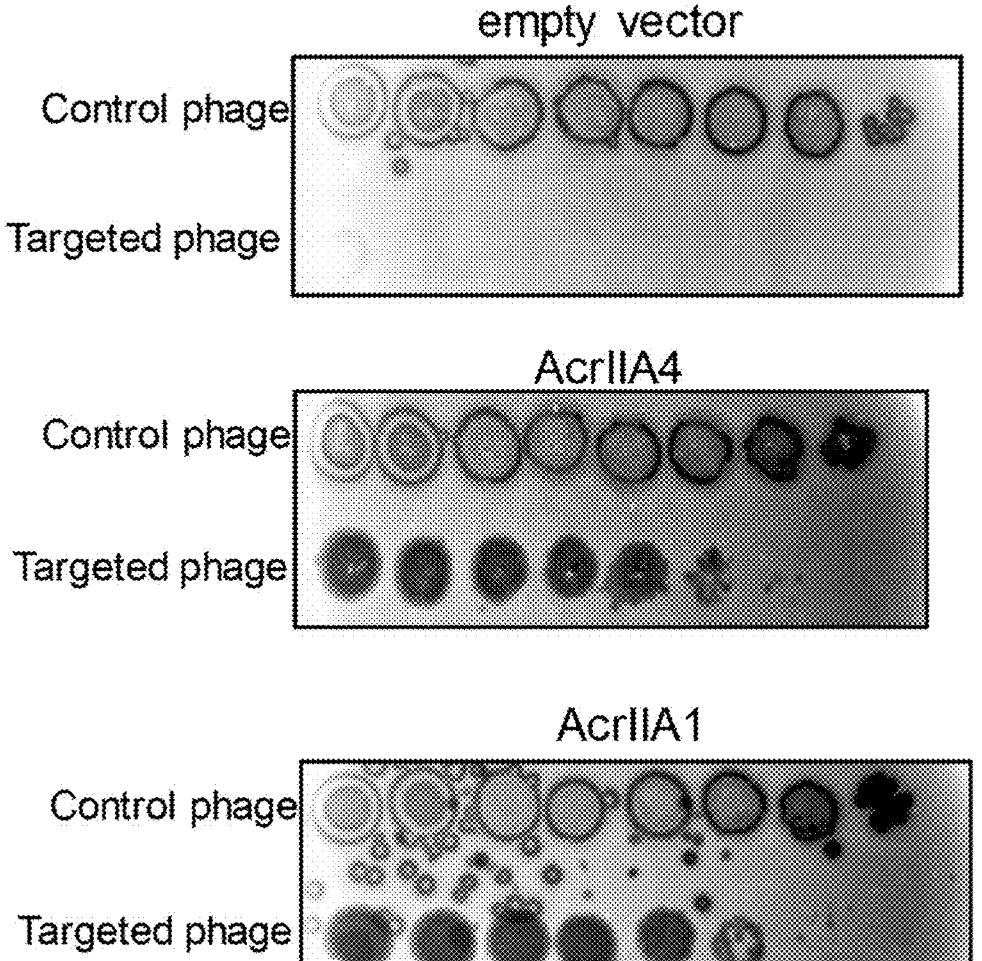

FIG. 14: Phage plaque assays showing ten-fold dilutions of a control phage (D3) or a phage targeted (JBD30) by SpyCas9 with a JBD30-specific sgRNA in a heterologous host (*Pseudomonas aeruginosa*). Expression of the indicated anti-CRISPR acrIIA4 (positive control) or acrIIA1 inactivates SpyCas9.

Figures 15A, 15B:
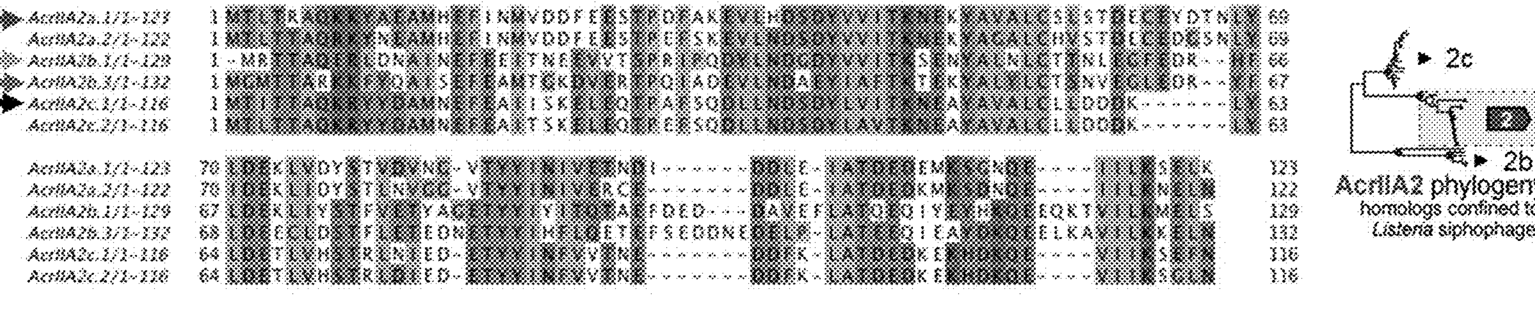

FIG. 15A-B: 15A) A multi-sequence alignment of acrIIA2 homologs found in different *Listeria* mobile elements. (AcrIIA2a.1 (SEQ ID NO:69); AcrIIA2a.2 (SEQ ID NO:84); AcrIIA2b.1 (SEQ ID NO:108); AcrIIA2b.3 (SEQ ID NO:209); AcrIIA2c.1 (SEQ ID NO:97); and AcrIIA2c.2 (SEQ ID NO:98)). Tested homologs are indicated with colored arrows and a summary of the results are shown below the alignment, 15B) A table summarizing the sequence identity (at the amino acid level) between the different homologs and their accession numbers.

Figure 16:
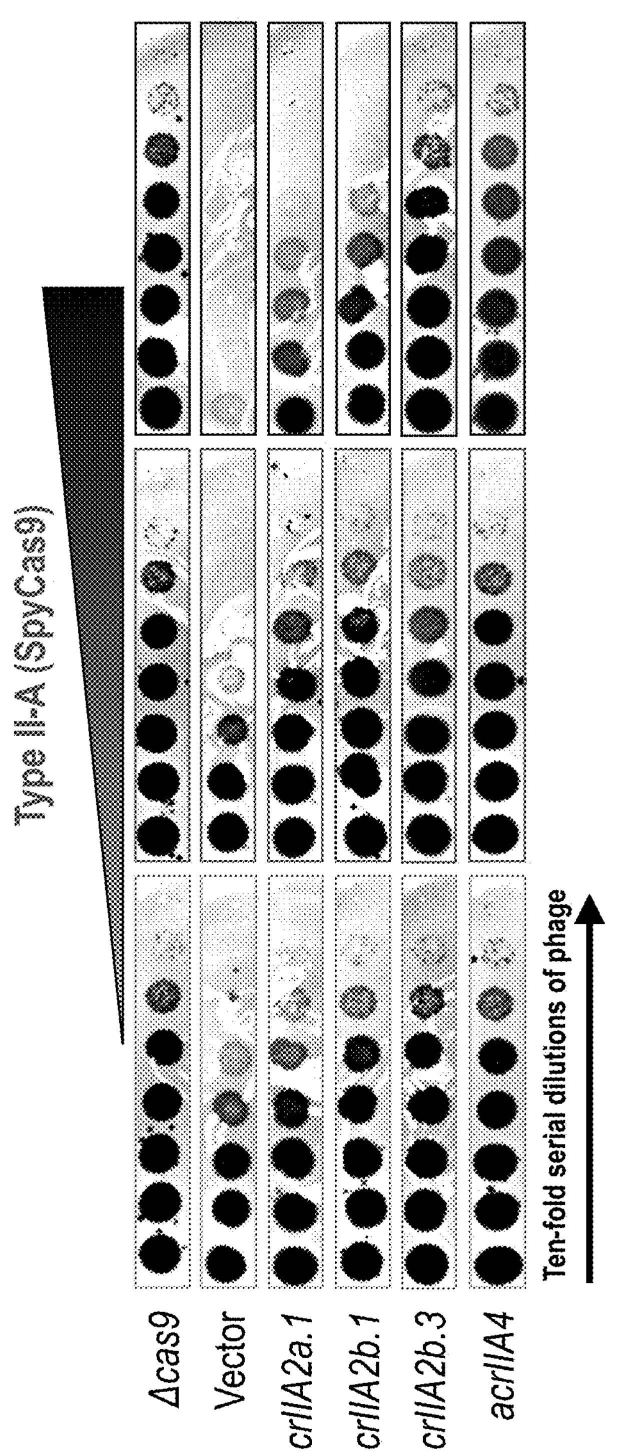

FIG. 16: Bacteriophage plaque assays with ten-fold serial dilutions phage JBD30 spotted on top of a lawn of *P. aeruginosa* expressing SpyCas9 and a sgRNA targeting phage JBD30. Phages will plaque in the absence of CRISPR activity. Cas9 and the sgRNA are induced with increasing amounts of arabinose from left to right (0.001%, 0.01%, 0.1%). In the absence of Cas9 (Δcas9), the phages plaque fully, but in the present of Cas9 but no anti-CRISPR (vector), plaguing is reduced as Cas9 is induced. The provision of acrIIA4 (positive control) fully blocks Cas9 at all levels. Only acrIIA2b.3 is comparable to acrIIA4 for its activity. The original acrIIA2a.1 is only partially active, with a slight improvement seen with acrIIA2b.1.

FIG. 17: Homologs of acrIIA3b found in *Streptococcus* species were tested for anti-CRISPR activity in heterologous system (*P. aeruginosa*) expressing SpyCas9 and an sgRNA. A summary of the results (data in FIG. 6) are shown in the table, indicating the species of origin for the anti-CRISPR, the sequence identity of Cas9 in that species to *S. pyogenes*, and similar information for the anti-CRISPR. Given the previously observed toxicity of acrIIA3a and acrIIA3b, these new proteins were assessed for toxicity (toxic?) and anti-CRISPR function (acr?).

Figure 18:
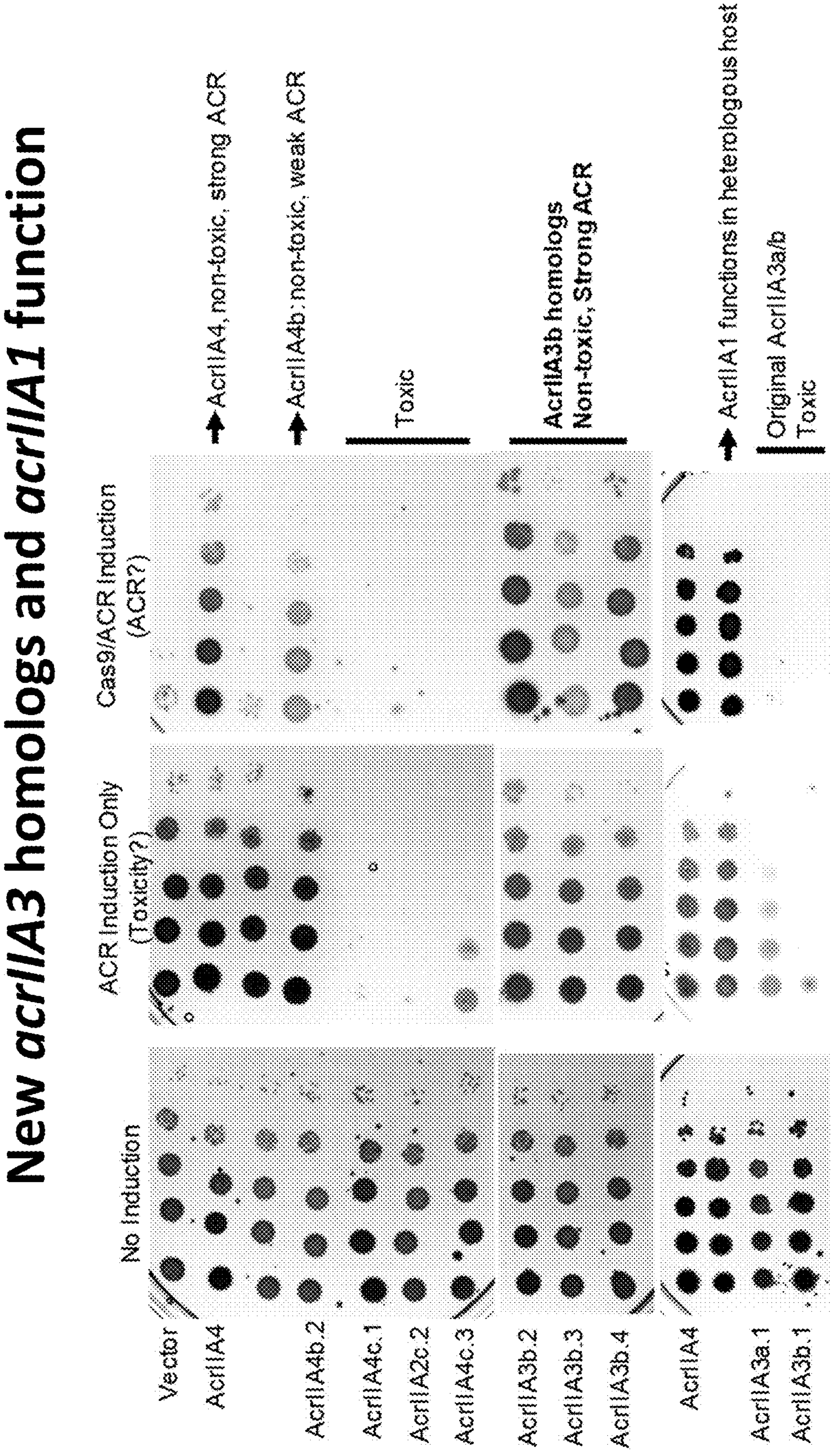

FIG. 18: Spot titration of bacterial cells on LB agar plates. SpyCas9 was programmed with an sgRNA targeting the *P. aeruginosa* genome, thus killing the cell. Cells only survive if the anti-CRISPR is functional. Plates are showing 10-fold serial dilutions of cells plated on non-inducing (left column), ACR inducing only (middle column, to test ACR toxicity), or Cas9/sgRNA/ACR inducing plates (right column, to test ACR function). Genome being cleaved by Cas9 leads to death, unless anti-CRISPR blocks Cas9 function. Colonies on right-most panels indicate ACR activity.

FIG. 19: Summary of some of the data from Example 2.

DETAILED DESCRIPTION OF THE INVENTION

Several polypeptide inhibitors ("Cas9-inhibiting polypeptides") of Cas9 nuclease have been identified from phage. The Cas9-inhibiting polypeptides initially discovered from phage were designated AcrIIA1, AcrIIA2, AcrIIA3, and AcrIIA4.

The Cas9-inhibiting polypeptides described herein can be used in many aspects to inhibit unwanted Cas9 activity. For example, one or more Cas9-inhibiting polypeptide can be used to regulate Cas9 in genome editing, thereby allowing for some Cas9 activity prior to introduction of the Cas9-inhibiting polypeptide. This can be helpful, for example, in limiting off-target effects of Cas9. This and other uses are described in more detail below.

As set forth in the examples and sequence listing, a large number of Cas9-inhibiting polypeptides have been discovered. Examples of exemplary Cas9-inhibiting polypeptides include proteins comprising any of SEQ ID NOs: 1-169, or substantially (e.g., at least 50, 60, 70, 75, 80, 85, 90, 95, or 98%) identical amino acid sequences. In some embodiments, the polypeptides, in addition to having one of the above-listed sequences, will include other amino acid sequences or other chemical moieties (e.g., detectable labels) at the amino terminus, carboxyl terminus, or both. Additional amino acid sequences can include, but are not limited to tags, detectable markers, or nuclear localization signal sequences.

As noted in the examples, a number of the Cas9-inhibiting polypeptides have been shown to inhibit *L. monocytogenes* Cas9 as well as *S. pyogenes* (Spy) Cas9. It is believed and expected that the Cas9-inhibiting polypeptides described herein will also similarly inhibit other block II-A Cas9 proteins. As used herein, a "Cas9-inhibiting polypeptide" is a protein that inhibits function of the Cas9 enzyme in *L. monocytogenes* during a transformation efficiency assay. When a plasmid bearing a targeted DNA sequence and protospacer adjacent motif (PAM) is used to transform a strain with intact Cas9 function, the transformation event is prevented by Cas9, generating miniscule colonies under selection. This is compared to a plasmid with a non-targeted DNA sequence, which produces normal sized colonies when used to transform *L. monocytogenes*. The expression of a Cas9 inhibitor neutralizes Cas9 activity and leads to transformed, normal sized colonies of both the targeted and non-targeted plasmid. While it is believed the Cas9-inhibiting polypeptides' inhibitory activity can be measured in other ways, the above assay, presented in more detail in the Examples, is the assay for determining whether the Cas9-inhibiting polypeptide have activity.

The Cas9-inhibiting polypeptides can be introduced into any cell to inhibit Cas9 in that cell. In some embodiments, the cell contains Cas9 protein when the Cas9-inhibiting polypeptide is introduced into the cell. In other embodiments, the Cas9-inhibiting polypeptide is introduced into the cell and then Cas9 polypeptide is introduced into the cell.

Introduction of the Cas9-inhibiting polypeptides into the cell can take different forms. For example, in some embodiments, the Cas9-inhibiting polypeptides themselves are introduced into the cells. Any method for introduction of polypeptides into cells can be used. For example, in some embodiments, electroporation, or liposomal or nanoparticle delivery to the cells can be employed. In other embodiments, a polynucleotide encoding a Cas9-inhibiting polypeptide is introduced into the cell and the Cas9-inhibiting polypeptide is subsequently expressed in the cell. In some embodiments, the polynucleotide is an RNA. In some embodiments, the polynucleotide is a DNA.

In some embodiments, the Cas9-inhibiting polypeptide is expressed in the cell from RNA encoded by an expression cassette, wherein the expression cassette comprises a promoter operably linked to a polynucleotide encoding the Cas9-inhibiting polypeptide. In some embodiments, the promoter is heterologous to the polynucleotide encoding the Cas9-inhibiting polypeptide. Selection of the promoter will depend on the cell in which it is to be expressed and the desired expression pattern. In some embodiments, promoters are inducible or repressible, such that expression of a nucleic acid operably linked to the promoter can be expressed under selected conditions. In some examples, a promoter is an inducible promoter, such that expression of a nucleic acid operably linked to the promoter is activated or increased.

An inducible promoter may be activated by presence or absence of a particular molecule, for example, doxycycline, tetracycline, metal ions, alcohol, or steroid compounds. In some embodiments, an inducible promoter is a promoter that is activated by environmental conditions, for example, light or temperature. In further examples, the promoter is a repressible promoter such that expression of a nucleic acid operably linked to the promoter can be reduced to low or undetectable levels, or eliminated. A repressible promoter may be repressed by direct binding of a repressor molecule (such as binding of the trp repressor to the trp operator in the presence of tryptophan). In a particular example, a repressible promoter is a tetracycline repressible promoter. In other examples, a repressible promoter is a promoter that is repressible by environmental conditions, such as hypoxia or exposure to metal ions.

In some embodiments, the polynucleotide encoding the Cas9-inhibiting polypeptide (e.g., as part of an expression cassette) is delivered to the cell by a vector. For example, in some embodiments, the vector is a viral vector. Exemplary viral vectors can include, but are not limited to, adenoviral vectors, adeno-associated viral (AAV) vectors, and lentiviral vectors.

In some embodiments, the Cas9-inhibiting polypeptide or a polynucleotide encoding the Cas9-inhibiting polypeptide is delivered as part of or within a cell delivery system. Various delivery systems are known and can be used to administer a composition of the present disclosure, for example, encapsulation in liposomes, microparticles, microcapsules, or receptor-mediated delivery.

Exemplary liposomal delivery methodologies are described in Metselaar et al., Mini Rev. Med. Chem. 2(4): 319-29 (2002); O'Hagen et al., Expert Rev. Vaccines 2(2): 269-83 (2003); O'Hagan, Curr. Drug Targets Infjct. Disord. 1(3):273-86 (2001); Zho et al., Biosci Rep. 22(2):355-69 (2002); Chikh et al., Biosci Rep. 22(2):339-53 (2002); Bungener et al., Biosci. Rep. 22(2):323-38 (2002); Park, Biosci Rep. 22(2):267-81 (2002); Ulrich, Biosci. Rep. 22(2): 129-50; Lofthouse, Adv. Drug Deliv. Rev. 54(6):863-70 (2002); Zhou et al., J. Inmunmunother. 25(4):289-303 (2002); Singh et al., Pharm Res. 19(6):715-28 (2002); Wong et al., Curr. Med. Chem. 8(9):1123-36 (2001); and Zhou et al., Immunonmethods (3):229-35 (1994).

Exemplary nanoparticle delivery methodologies, including gold, iron oxide, titanium, hydrogel, and calcium phosphate nanoparticle delivery methodologies, are described in Wagner and Bhaduri, Tissue Engineering 18(1): 1-14 (2012) (describing inorganic nanoparticles); Ding et al., Mol Ther e-pub (2014) (describing gold nanoparticles); Zhang et al., Langmuir 30(3):839-45 (2014) (describing titanium dioxide nanoparticles); Xie et al., Curr Pharm Biotechnol 14(10): 918-25 (2014) (describing biodegradable calcium phosphate nanoparticles); and Sizovs et al., J Am Chem Soc 136(1): 234-40 (2014).

Introduction of a Cas9-inhibiting polypeptide as described herein into a prokaryotic cell can be achieved by any method used to introduce protein or nuclei acids into a prokaryote. In some embodiments, the Cas9-inhibiting polypeptide is delivered to the prokaryotic cell by a delivery vector (e.g., a bacteriophage) that deliver a polynucleotide encoding the Cas9-inhibiting polypeptide. In some embodiments, inhibiting Cas9 in the prokaryote could either help that phage kill the bacterium or help other phages kill it.

A Cas9-inhibiting polypeptide as described herein can be introduced into any cell that contains, expresses, or is expected to express, Cas9. Exemplary cells can be prokaryotic or eukaryotic cells. Exemplary prokaryotic cells can include but are not limited to, those used for biotechnological purposes, the production of desired metabolites, *E. coli* and human pathogens. Examples of such prokaryotic cells can include, for example, *Escherichia coli, Pseudomonas* sp., *Corynebacterium* sp., *Bacillus subtitis, Streptococcus pneumonia, Pseudomonas aeruginosa, Staphylococcus aureus, Campylobacter jejuni, Francisella novicida, Corynebacterium diphtheria, Enterococcus* sp., *Listeria monocytogenes, Mycoplasma gallisepticum, Streptococcus* sp., or *Treponema denticola*. Exemplary eukaryotic cells can include, for example, animal (e.g., mammalian) or plant cells. Exemplary mammalian cells include but are not limited to human, non-human primates. mouse, and rat cells. Cells can be cultured cells or primary cells. Exemplary cell types can include, but are not limited to, induced pluripotent cells, stem cells or progenitor cells, and blood cells, including but not limited to T-cells or B-cells.

In some embodiments, the cells are removed from an animal (e.g., a human, optionally in need of genetic repair), then Cas9, and optionally guide RNAs, for gene editing are introduced into the cell ex vivo, and a Cas9-inhibiting polypeptide is introduced into the cell. In some embodiments, the cell(s) is subsequently introduced into the same animal (autologous) or different animal (allogeneic).

In any of the embodiments described herein, a Cas9 polypeptide can be introduced into a cell to allow for Cas9 DNA binding and/or cleaving (and optionally editing), followed by introduction of a Cas9-inhibiting polypeptides as described herein. This timing of the presence of active Cas9 in the cell can thus be controlled by subsequently supplying Cas9-inhibiting polypeptides to the cell, thereby inactivating Cas9. This can be useful, for example, to reduce Cas9 "off-target" effects such that non-targeted chromosomal sequences are bound or altered. By limiting Cas9 activity to a limited "burst" that is ended upon introduction of the Cas9-inhibiting polypeptide, one can limit off-target effects. In some embodiments, the Cas9 polypeptide and the Cas9-inhibiting polypeptide are expressed from different inducible promoters, regulated by different inducers. These embodiments allow for first initiating expression of the Cas9 polypeptide followed later by induction of the Cas9-inhibiting polypeptide, optionally while removing the inducer of Cas9 expression.

In some embodiments, a Cas9-inhibiting polypeptide as described herein can be introduced (e.g., administered) to an animal (e.g., a human) or plant. This can be used to control in vivo Cas9 activity, for example in situations in which CRISPR/Cas9 gene editing was performed in vivo, or in circumstances in which an individual is exposed to unwanted Cas9, for example where a bioweapon comprising Cas9 is released.

In some embodiments, the Cas9-inhibiting polypeptides or a polynucleotide encoding the Cas9-inhibiting polypeptide, in administered as a pharmaceutical composition. In some embodiments, the composition comprises a delivery system such as a liposome, nanoparticle or other delivery vehicle as described herein or otherwise known, comprising the Cas9-inhibiting polypeptides or a polynucleotide encoding the Cas9-inhibiting polypeptide. The compositions can be administered directly to a mammal (e.g., human) to inhibit Cas9 using any route known in the art, including e.g., by injection (e.g., intravenous, intraperitoneal, subcutaneous, intramuscular, or intradermal), inhalation, transdermal application, rectal administration, or oral administration.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989).

EXAMPLES

Example 1

Results

CRISPR-Cas9 in *Listeria monocytogenes* Targets Foreign DNA

*Listeria monocytogenes* is a facultative intracellular food-borne pathogen with a well characterized phage population. Many *L. monocytogenes* isolates have type II-A CRISPR-Cas systems (Sesto, N. et al. (2014). *PLoS Genet,* 10, e1004065) and their CRISPR spacers possess identity to many virulent, temperate, and integrated phages (Di, H. et al. (2014) *Biochem Biophys Res Commun,* 454, 399-403; Sesto, N. et al. (2014). *PLoS Genet,* 10, e1004065). However, there is no experimental evidence of canonical CRISPR-Cas function. We analyzed 275 genomes of *L. monocytogenes* and identified type II-A CRISPR-Cas9 systems (Lmo Cas9) in 15% (n=41) of genomes (FIG. 1B). Interestingly, we found eight genomes (3% of the total), with examples of self-targeting (FIGS. 1B and 1C) although CRISPR-cas9 is anticipated to be functional as the CRISPR repeat, PAM, tracrRNA, Cas9, and the associated promoters lack obvious inactivating mutations (FIG. 6A-E). We predicted that these strains possess inhibitors of CRISPR-Cas9 that allow the stable co-existence of a spacer-protospacer pair.

Figures 2A, 2B, 2C, 2D:
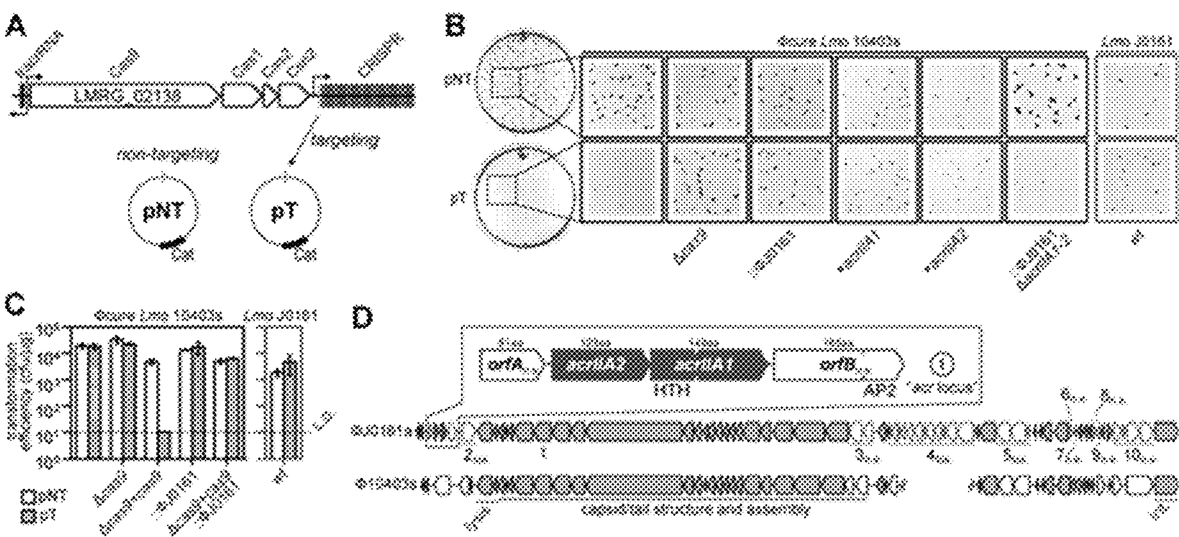
FIG. 2A-D. A prophage from *L. monocytogenes* J0161 contains two CRISPR-Cas9 inhibitor genes.

To test whether inhibitors were encoded by the prophages of *L. monocytogenes*, we first established the functionality of uninhibited CRISPR-Cas9 in an *L. monocytogenes* strain (10403s) that does not exhibit self-targeting. To test the activity of this system we designed a plasmid (pT) possessing a targeted protospacer (i.e. a sequence that is complementary to a natural spacer in the CRISPR array) along with a cognate protospacer adjacent motif (PAM), a three base motif that is necessary for Cas9 binding (FIG. 2A). We measured the transformation efficiency of 10403s with either pT or a control plasmid possessing a non-targeted sequence with an identical plasmid backbone (pNT). To simplify downstream analysis, a prophage cured version of 10403s (ϕcure) was used for all downstream experiments since it was indistinguishable from wt10403s in this assay (FIG. 7). Transformation with pT yielded miniscule colonies relative to pNT (FIG. 2B, leftmost panel), although the number of colonies that emerged upon prolonged incubation were the same (FIG. 2C, see Discussion for further analysis). To confirm that this phenotype was the result of CRISPR-Cas9 interference, we constructed a cas9-deletion strain. Transformation of this strain with pT and pNT produced colonies of indistinguishable size (FIG. 2B $2^{nd}$ left panel). However, adding back cas9 to the *L. monocytogenes* chromosome under a constitutively active promoter completely inhibited transformation with pT (FIG. 2C). Together, these experiments demonstrate that Cas9 is functional in the *L. monocytogenes* strain 10403s at both endogenous and overexpressed levels, and limits transformation with a plasmid bearing a protospacer.

Resident Prophages Inactivate CRISPR-Cas9 in *L. monocytogenes*

To determine whether CRISPR-Cas9 may be disabled in a strain with self-targeting spacers, we examined immunity function in *L. monocytogenes* strain J0161, whose spacer 16 perfectly matches a prophage (ϕJ0161a) in the same genome (FIG. 1C). We could not detect any clearly deleterious CRISPR-Cas mutations in J0161, suggesting that this self-targeting scenario was the result of inhibition and not loss of function (FIG. 6B-F). Since the type II-A CRISPR array of J0161 is distinct from that of 10403s, a J0161-specific targeted plasmid ($pT_{J0161}$) was used to test the function CRISPR-Cas9 in J0161. Consistent with the inactivation implied by self-targeting, there was no significant difference in transformation efficiency or colony size to distinguish $pT_{J0161}$ from pNT (FIGS. 2B and 2C, rightmost panel). Thus, we reasoned that that the J0161 genome may encode Cas9 inhibitors.

In search of the genetic basis for CRISPR-Cas9 inactivation in J0161, we focused on the prophage ϕJ0161a as a likely source of an inhibitor gene because it contained the self-targeted sequence in this strain. To determine whether ϕJ0161a contained an inhibitor, the prophage-cured strain of 10403s was lysogenized with ϕJ0161a and assayed for CRISPR-Cas9 functionality by plasmid transformation. While ϕcure10403s strain targeted pT, the acquisition of ϕJ0161a was sufficient to inactivate CRISPR-Cas9 function (FIG. 2B, $3^{rd}$ panel from left and 2C, $4^{th}$ from left), suggesting that this prophage encodes an inhibitor of CRISPR-Cas9. The ϕJ0161a prophage also inactivated plasmid targeting in a strain constitutively expressing cas9, suggesting that the inhibitory mechanism does not operate by disrupting natural regulation of the cas9 promoter (FIG. 2C, $5^{th}$ from left).

Given that ϕJ0161a inhibited CRISPR-Cas9 function, and the endogenous prophage ϕ10403s did not, we compared the genomes of these two closely related phages to identify the regions of difference (FIG. 2D). In addition to sharing 39 core phage genes with >40% protein sequence identity, ten non-overlapping unique clusters of genes were identified (cluster boundaries were chosen based on predicted operon structure, with 1-12 genes per cluster). Each cluster was cloned and integrated into the genome of prophage-cured 10403s and assayed for CRISPR-Cas9 function. Of the ten fragments, seven were successfully introduced into *L. monocytogenes*, while three fragments could not be inserted in the *L. monocytogenes* genome and were presumably toxic in isolation. Plasmid transformation assays revealed that ϕJ0161a fragment 1 was the only fragment capable of inhibiting CRISPR-Cas9, indicating that his fragment encoded at least one CRISPR-Cas9 inhibitor (FIG. 2D, FIG. 8). Expressing the individual genes from this four-gene fragment led to the conclusive identification of two anti-CRISPR genes, LMOG_03146 and LMOG_03147 (herein referred to as acrIIA1 and acrIIA2, respectively; FIGS. 2B and 2D). Deletion of both acrIIA1 and acrIIA2 from a 10403s::ϕJ0161a lysogen restored CRISPR-Cas9 function, confirming that these are the only anti-CRISPR genes in ϕJ0161a (FIG. 2B).

Anti-CRISPR Loci are Widespread in *L. monocytogenes*

To identify additional type II-A anti-CRISPRs, the genomic position analogous to that of acrIIA1 and acrIIA2 in related *L. monocytogenes* prophages was examined. A recurring anti-CRISPR (acr) locus containing acrIIA1 within in a small operon (2-5 genes) of highly conserved gene order was identified between the left integration site and the genes involved in cell lysis (FIG. 3A). We identified five novel protein families conserved within acr loci. To test these, we cloned and integrated representatives into the 10403s genome and assayed the transformation efficiency of pT and pNT. Two new genes were identified that were capable of CRISPR inactivation (acrIIA3 and acrIIA4), while the remaining three (orfC, D, E) were not (FIG. 3A, FIG. 9).

To determine whether CRISPR-Cas9 inactivation in *L. monocytogenes* is pervasive, we next analyzed the conservation pattern for each anti-CRISPR. Although each acrIIA gene was sufficient to inactivate CRISPR-Cas9 in isolation, we observed a common presence of acrIIA1 in most acr loci. Nearly all instances (91%) of acrIIA2-4 were found upstream of the helix-turn-helix (HTH) motif-containing acrIIA1, suggesting that this gene may be a marker for acr loci (FIG. 3B). The most common scenario we observed in 119 acr loci were either acrIIA1-2 or acrIIA1-2-3, representing 66% of acr loci. In total, acrIIA genes were identified in 25% of *L. monocytogenes* genomes, with approximately 50% of *L. monocytogenes* cas9-containing strains possessing at least one anti-CRISPR in the same genome (FIG. 3C). Many instances of *L. monocytogenes* genomes possessing multiple acrIIA-encoding prophages were also identified (Supplementary Table 1). Furthermore, at least one acrIIA gene was found in the genomes of all eight instances of self-targeting that were initially identified (FIG. 1B, Supplementary Table 1), explaining how these scenarios are stable. Together, these data suggest widespread prophage-mediated inactivation of CRISPR-Cas9 in *L. monocytogenes*.

TABLE S1 acrIIA Gene Conservation, Related to FIGS. 1B 4B and 4C
genomes that lack cas9 and all known acrIIA genes 264
genomes that contain cas9 but lack all known acrIIA genes 33
genomes contain cas9 and acrIIA genes 37
genomes that lack cas9, but contain acrIIA genes 65
unpaired acr genes

| control (cysS) | acrIIA3 | acrIIA2 | acrIIA1 | acrIIA4 | Cas9 | ST strains |
|---|---|---|---|---|---|---|
| AEO05249.1 | | | | | AEO07576.1 | |
| AKI48207.1 | | | | | AKI50529.1 | |
| AMD50972.1 | | | | | AMD53187.1 | |
| AMR52783.1 | | | | | AMR55031.1 | |
| EEW14429.1 | | | | | EEW14776.1 | |
| KES84268.1 | | | | | KES86621.1 | |
| KET22766.1 | | | | | KET25022.1 | |
| KET54818.1 | | | | | KET56390.1 | |
| KEU03893.1 | | | | | KEU00315.1 | |
| KEU81061.1 | | | | | KEU82991.1 | |
| KEU92860.1 | | | | | KEU94779.1 | |
| KEV01501.1 | | | | | KEV04018.1 | |
| KEV13316.1 | | | | | KEV15767.1 | |
| KEV34890.1 | | | | | KEV37443.1 | |
| KEV87445.1 | | | | | KEV88657.1 | |
| KEW12308.1 | | | | | KEW13456.1 | |
| KEW54858.1 | | | | | KEW57091.1 | |
| KEX56334.1 | | | | | KEX57585.1 | |
| KEX62909.1 | | | | | KEX64108.1 | |
| KEX85751.1 | | | | | KEX84898.1 | |
| KFL18307.1 | | | | | KFL20187.1 | |
| KHK15389.1 | | | | | KHK15281.1 | |
| KPV81115.1 | | | | | KPV80639.1 | |
| KTA33634.1 | | | | | KTA27954.1 | |
| KTA40577.1 | | | | | KTA36142.1 | |
| KTA59125.1 | | | | | KTA59526.1 | |
| KTE88758.1 | | | | | KTE86646.1 | |
| KXS69410.1 | | | | | KXS73069.1 | |
| KXX03397.1 | | | | | KXX04680.1 | |
| KXX27153.1 | | | | | KXX27120.1 | |
| KYH47795.1 | | | | | KYH48716.1 | |
| KEX06234.1 | | | | | KEX03765.1 | |
| AGR07328.1 | | | | | AGR09779.1 | |
| EFG02722.1 | EFG02166.1 | EFG02165.1 | FG02164.1 | | EFG02048.1 | FSL J1-194 |
| AEO02308.1 | | AEO04363.1 | AEO04364.1<br>AEO04690.1 | AEO04689.1 | AEO04756.1 | J0161 |
| AKI51021.1 | AKI52063.1<br>AKI53105.1 | AKI52062.1<br>AKI53106.1 | AKI52061.1<br>AKI53107.1 | | AKI53425.1 | L1846 |
| AKI41163.1 | AKI40129.1 | AKI40130.1 | AKI40131.1 | | AKI42028.1 | L2626 |
| AGR26778.1 | AGR27459.1 | AGR27460.1 | AGR27297.1<br>AGR27461.1 | | AGR27343.1 | R2-502 |
| EEW19474.1 | | | EEW20426.1 | | EEW20201.1 | R2-503 |
| AHJ04747.1 | AHJ02948.1 | AHJ02947.1 | AHJ02946.1 | | AHJ04249.1 | WSLC1001 |
| AKI42516.1 | AKI43551.1 | AKI43550.1 | AKI43549.1 | | AKI44910.1 | |
| EXL23533.1 | EXL25968.1 | | | | EXL23613.1 | |

TABLE S1-continued acrIIA Gene Conservation, Related to FIGS. 1B 4B and 4C
genomes that lack cas9 and all known acrIIA genes 264
genomes that contain cas9 but lack all known acrIIA genes 33
genomes contain cas9 and acrIIA genes 37
genomes that lack cas9, but contain acrIIA genes 65
unpaired acr genes

| control (cysS) | acrIIA3 | acrIIA2 | acrIIA1 | acrIIA4 | Cas9 | ST strains |
|---|---|---|---|---|---|---|
| EZH70416.1 | EZH69742.1 | EZH71062.1 | EZH69029.1<br>EZH71063.1 | | EZH69562.1 | |
| KEU59490.1 | KEU52815.1 | KEU52814.1 | KEU52813.1 | | KEU61049.1 | |
| KHK05112.1 | KHK09045.1 | KHK09044.1 | KHK04755.1<br>KHK09043.1 | | KHK11936.1 | |
| KID24070.1 | KID23649.1 | KID23650.1<br>KID25721.1 | KID23651.1<br>KID25720.1 | | KID22034.1 | |
| KKB89786.1 | KKB89545.1 | KKB87491.1<br>KKB89544.1 | KKB87492.1<br>KKB89543.1 | | KKB87210.1 | |
| KTA33603.1 | KTA31236.1 | KTA31235.1 | KTA28092.1<br>KTA31234.1 | | KTA28352.1 | |
| KTA58546.1 | KTA51620.1 | KTA51621.1 | KTA51622.1 | | KTA50572.1 | |
| KXS57839.1 | KXS58608.1 | KXS58607.1 | KXS58606.1 | KXS56938.1 | KXS59964.1 | |
| EAL04996.1 | | EAL06504.1 | EAL05810.1<br>EAL06505.1 | EAL05809.1 | EAL05449.1 | |
| EEW23167.1 | | EEW22373.1 | EEW22374.1<br>EEW23440.1 | EEW23439.1 | EEW22432.1 | |
| EFF99811.1 | | EFG00297.1 | EFG00298.1<br>EFG00183.1 | EFG00182.1 | EFF99171.1 | |
| EHY63973.1 | | | | EHY61390.1 | EHY61427.1 | |
| EXL17326.1 | | | EXL17712.1 | EXL17711.1 | EXL16255.1 | |
| KTA40536.1 | | KTA33666.1 | KTA31190.1<br>KTA33667.1 | KTA31189.1 | KTA29552.1 | |
| KXS59387.1 | | KXS56902.1 | KXS64534.1 | KXS57719.1 | KXS62773.1 | |
| KXW90032.1 | | KXW85500.1 | KXW85495.1<br>KXW85497.1 | KXW85912.1 | KXW90865.1 | |
| KTA67982.1 | | | KTA68177.1 | | KTA68618.1 | |
| AGR14764.1 | | | AGR15693.1 | | AGR15756.1 | |
| ALU77418.1 | | | ALU78083.1 | | ALU77910.1 | |
| EFK41798.1 | | | EFK41083.1 | | EFK42981.1 | |
| KHK20071.1 | | | KHK19909.1 | | KHK21360.1 | |
| KHK20265.1 | | | KHK17523.1 | | KHK22389.1 | |
| KHK26884.1 | | KHK28212.1 | KHK28213.1 | | KHK29000.1 | |
| KHK32359.1 | | KHK33774.1 | KHK33773.1 | | KHK34506.1 | |
| KID12814.1 | | KID20146.1 | KID20145.1 | | KID19562.1 | |
| KID16736.1 | | KID21567.1 | KID21568.1 | | KID 14794.1 | |
| KID25109.1 | | KID27661.1 | KID27662.1 | | KID22855.1 | |
| KXX34587.1 | | KXX34834.1<br>KXX34219.1 | KXX34835.1 | | KXX35452.1 | |
| ACK40737.1 | ACK39691.1 | ACK39692.1 | ACK39693.1 | ACK40885.1 | | |
| AEH91268.1 | AEH92315.1 | AEH92314.1 | AEH92313.1 | AEH91120.1 | | |
| ALU81417.1 | ALU80614.1 | ALU80615.1 | ALU80616.1 | | | |
| EXL28212.1 | EXL28247.1 | EXL28248.1 | EXL28249.1 | | | |
| KES32042.1 | KES29691.1 | KES29690.1 | KES29689.1 | | | |
| KES38767.1 | KES36191.1 | KES36190.1 | KES36189.1 | | | |
| KES64642.1 | KES69056.1 | KES69057.1 | KES69058.1 | | | |
| KET22488.1 | KET20225.1 | KET20226.1 | KET20227.1 | | | |
| KET33547.1 | KET33008.1 | KET33009.1 | KET33010.1 | | | |
| KET65150.1 | KET67219.1 | KET67220.1 | KET67221.1 | | | |
| KEU38314.1 | KEU32638.1 | KEU32639.1 | KEU32640.1 | | | |
| KEU70290.1 | KEU73964.1 | KEU69222.1 | KEU69221.1 | | | |
| KEU77521.1 | KEU79801.1 | KEU73965.1<br>KEU79802.1 | KEU73966.1<br>KEU79803.1 | | | |
| KEU85819.1 | KEU87627.1 | KEU87628.1 | KEU87629.1 | | | |
| KEW39277.1 | KEW37877.1 | KEW37876.1 | KEW37875.1 | | | |
| KEW47138.1 | KEW38798.1 | KEW38797.1 | KEW38796.1 | | | |
| KEW52188.1 | KEW54596.1 | KEW54597.1 | KEW54598.1 | | | |
| KEW87000.1 | KEW91381.1 | KEW91380.1 | KEW91379.1 | | | |
| KEX05231.1 | KEX03851.1 | KEX03850.1 | KEX03849.1 | | | |
| KEX16623.1 | KEX13878.1 | KEX13879.1 | KEX13880.1 | | | |
| KEX48257.1 | KEX45733.1 | KEX45732.1 | KEX45731.1 | | | |
| KEX44142.1 | KEX49273.1 | KEX49272.1 | KEX49271.1 | | | |
| KHK37385.1 | KHK39424.1 | KHK39423.1 | KHK39422.1 | | | |
| KLI10624.1 | KLI10452.1<br>KLI12476.1 | KLI10451.1<br>KLI12475.1 | KLI10195.1<br>KLI10251.1 | KLI10194.1 | | |
| KNX95479.1 | KNX95907.1<br>KNX94640.1 | KNX95906.1<br>KNX94641.1 | | | | |
| KPJ28401.1 | KPJ30389.1 | KPJ30390.1 | KPJ30391.1 | | | |
| KPV83306.1 | KPV85471.1 | KPV85472.1 | KPV85473.1 | | | |
| KTA46249.1 | KTA44520.1 | KTA44521.1 | KTA44522.1<br>KTA45326.1 | | | |

TABLE S1-continued acrIIA Gene Conservation, Related to FIGS. 1B 4B and 4C
genomes that lack cas9 and all known acrIIA genes 264
genomes that contain cas9 but lack all known acrIIA genes 33
genomes contain cas9 and acrIIA genes 37
genomes that lack cas9, but contain acrIIA genes 65
unpaired acr genes

| control (cysS) | acrIIA3 | acrIIA2 | acrIIA1 | acrIIA4 | Cas9 | ST strains |
|---|---|---|---|---|---|---|
| KTA51238.1 | KTA50253.1 | KTA50252.1 | KTA50251.1 | | | |
| | | | KTA50988.1 | | | |
| KTA64947.1 | KTA62142.1 | KTA62143.1 | KTA62144.1 | | | |
| KXS86581.1 | KXS85159.1 | KXS85158.1 | KXS85157.1 | | | |
| KXX46503.1 | KXX46300.1 | KXX46299.1 | KXX46298.1 | | | |
| KXX49128.1 | KXX48607.1 | KXX48606.1 | KXX48605.1 | | | |
| KXX50214.1 | KXX49264.1 | KXX49263.1 | KXX49262.1 | | | |
| AKI55317.1 | | | AKI56173.1 | AKI56172.1 | | |
| AMD23307.1 | | | AMD24317.1 | AMD24318.1 | | |
| KKD52037.1 | | | KKD49091.1 | KKD49092.1 | | |
| KTA47721.1 | | | KTA46387.1 | KTA46388.1 | | |
| KTA50332.1 | | | KTA52328.1 | KTA52327.1 | | |
| KXS77556.1 | | | | KXS77365.1 | | |
| KXS79013.1 | | | | KXS78354.1 | | |
| KXX11384.1 | | | | KXX11218.1 | | |
| KXX17306.1 | | | | KXX17138.1 | | |
| KXX19133.1 | | | | KXX18287.1 | | |
| KES91745.1 | | KES96882.1 | KES96881.1 | | | |
| KET71424.1 | | KET73263.1 | KET73262.1 | | | |
| KET90504.1 | | KET94691.1 | KET94692.1 | | | |
| KEV66815.1 | | KEV69928.1 | KEV69929.1 | | | |
| KEV93156.1 | | KEV93282.1 | KEV93281.1 | | | |
| KEW04107.1 | | KEW08181.1 | KEW08182.1 | | | |
| KEW04863.1 | | KEW09554.1 | KEW09555.1 | | | |
| KEW11516.1 | | KEW17021.1 | KEW17020.1 | | | |
| KEW59026.1 | | KEW65182.1 | KEW65181.1 | | | |
| KEX05590.1 | | KEX05985.1 | KEX05984.1 | | | |
| KHK13841.1 | | | KHK12400.1 | | | |
| KJJ91084.1 | | KJJ91611.1 | KJJ91612.1 | | | |
| KJQ95289.1 | | KJQ94313.1 | KJQ94314.1 | | | |
| KJQ98292.1 | | KJQ95811.1 | KJQ95812.1 | | | |
| KJR57725.1 | | KJR51141.1 | KJR51140.1 | | | |
| KJR58524.1 | | KJR60208.1 | KJR60209.1 | | | |
| KKD51859.1 | | | KKD43688.1 | | | |
| KTA41666.1 | | | KTA35071.1 | | | |
| KTA65269.1 | | | KTA63900.1 | | | |
| KXF69083.1 | | KXF66382.1 | KXF66381.1 | | | |
| AGR12413.1 | | AGR07062.1 | AGR07061.1 | | | |
| AAT03038.1 | | | | | | |
| ADB67037.1 | | | | | | |
| ADB70126.1 | | | | | | |
| AEO24539.1 | | | | | | |
| AEO37792.1 | | | | | | |
| AFH78832.1 | | | | | | |
| AGR02736.1 | | | | | | |
| AGR04913.1 | | | | | | |
| AGR16038.1 | | | | | | |
| AGR21403.1 | | | | | | |
| AGR21930.1 | | | | | | |
| AGR32499.1 | | | | | | |
| AHF28095.1 | | | | | | |
| AHF30972.1 | | | | | | |
| AHF33963.1 | | | | | | |
| AHF36954.1 | | | | | | |
| AHF39945.1 | | | | | | |
| AHF42886.1 | | | | | | |
| AHI68925.1 | | | | | | |
| AHJ37147.1 | | | | | | |
| AHN31516.1 | | | | | | |
| AHY99532.1 | | | | | | |
| AIL67941.1 | | | | | | |
| AIZ37538.1 | | | | | | |
| AJA81957.1 | | | | | | |
| AJT44045.1 | | | | | | |
| AKG84402.1 | | | | | | |
| AKG87228.1 | | | | | | |
| AKI45409.1 | | | | | | |
| AKP37411.1 | | | | | | |
| AKS52855.1 | | | | | | |
| ALQ13660.1 | | | | | | |
| ALQ15375.1 | | | | | | |

TABLE S1-continued

| acrIIA Gene Conservation, Related to FIGS. 1B 4B and 4C<br>genomes that lack cas9 and all known acrIIA genes 264<br>genomes that contain cas9 but lack all known acrIIA genes 33<br>genomes contain cas9 and acrIIA genes 37<br>genomes that lack cas9, but contain acrIIA genes 65<br>unpaired acr genes | | | | | | |
|---|---|---|---|---|---|---|
| control (cysS) | acrIIA3 | acrIIA2 | acrIIA1 | acrIIA4 | Cas9 | ST strains |
| ALQ19576.1 | | | | | | |
| ALQ21479.1 | | | | | | |
| ALQ25193.1 | | | | | | |
| ALU83475.1 | | | | | | |
| ALX67727.1 | | | | | | |
| AMD26187.1 | | | | | | |
| ANE38117.1 | | | | | | |
| EAL07955.1 | | | | | | |
| EFD91450.1 | | | | | | |
| EFF96046.1 | | | | | | |
| EFR95169.1 | | | | | | |
| EGF38890.1 | | | | | | |
| EGJ23745.1 | | | | | | |
| ERH76184.1 | | | | | | |
| ERH76295.1 | | | | | | |
| ERH77379.1 | | | | | | |
| ERH83604.1 | | | | | | |
| ERH85425.1 | | | | | | |
| EUJ16754.1 | | | | | | |
| EXL13590.1 | | | | | | |
| EXL14999.1 | | | | | | |
| EXL25668.1 | | | | | | |
| KEK05609.1 | | | | | | |
| KEK07032.1 | | | | | | |
| KES28051.1 | | | | | | |
| KES28301.1 | | | | | | |
| KES38071.1 | | | | | | |
| KES42071.1 | | | | | | |
| KES42797.1 | | | | | | |
| KES48493.1 | | | | | | |
| KES50725.1 | | | | | | |
| KES54322.1 | | | | | | |
| KES54965.1 | | | | | | |
| KES55696.1 | | | | | | |
| KES63074.1 | | | | | | |
| KES63309.1 | | | | | | |
| KES72038.1 | | | | | | |
| KES79358.1 | | | | | | |
| KES79767.1 | | | | | | |
| KES80806.1 | | | | | | |
| KES82973.1 | | | | | | |
| KES86788.1 | | | | | | |
| KES92539.1 | | | | | | |
| KET00546.1 | | | | | | |
| KET04697.1 | | | | | | |
| KET06207.1 | | | | | | |
| KET08149.1 | | | | | | |
| KET08880.1 | | | | | | |
| KET13375.1 | | | | | | |
| KET15678.1 | | | | | | |
| KET17220.1 | | | | | | |
| KET30859.1 | | | | | | |
| KET35076.1 | | | | | | |
| KET38677.1 | | | | | | |
| KET39554.1 | | | | | | |
| KET41316.1 | | | | | | |
| KET44817.1 | | | | | | |
| KET47850.1 | | | | | | |
| KET53482.1 | | | | | | |
| KET55834.1 | | | | | | |
| KET60044.1 | | | | | | |
| KET62217.1 | | | | | | |
| KET69318.1 | | | | | | |
| KET74754.1 | | | | | | |
| KET76626.1 | | | | | | |
| KET81048.1 | | | | | | |
| KET85737.1 | | | | | | |
| KET86860.1 | | | | | | |
| KET91339.1 | | | | | | |
| KET98444.1 | | | | | | |
| KEU01781.1 | | | | | | |

TABLE S1-continued

| acrIIA Gene Conservation, Related to FIGS. 1B 4B and 4C<br>genomes that lack cas9 and all known acrIIA genes 264<br>genomes that contain cas9 but lack all known acrIIA genes 33<br>genomes contain cas9 and acrIIA genes 37<br>genomes that lack cas9, but contain acrIIA genes 65<br>unpaired acr genes | | | | | | |
|---|---|---|---|---|---|---|
| control (cysS) | acrIIA3 | acrIIA2 | acrIIA1 | acrIIA4 | Cas9 | ST strains |
| KEU03644.1 | | | | | | |
| KEU06655.1 | | | | | | |
| KEU10723.1 | | | | | | |
| KEU12483.1 | | | | | | |
| KEU18590.1 | | | | | | |
| KEU21146.1 | | | | | | |
| KEU23067.1 | | | | | | |
| KEU24780.1 | | | | | | |
| KEU30341.1 | | | | | | |
| KEU36177.1 | | | | | | |
| KEU37301.1 | | | | | | |
| KEU43040.1 | | | | | | |
| KEU43555.1 | | | | | | |
| KEU46678.1 | | | | | | |
| KEU51513.1 | | | | | | |
| KEU55425.1 | | | | | | |
| KEU55498.1 | | | | | | |
| KEU58686.1 | | | | | | |
| KEU64129.1 | | | | | | |
| KEU68275.1 | | | | | | |
| KEU69241.1 | | | | | | |
| KEU77548.1 | | | | | | |
| KEU86942.1 | | | | | | |
| KEU90182.1 | | | | | | |
| KEV00307.1 | | | | | | |
| KEV00562.1 | | | | | | |
| KEV06907.1 | | | | | | |
| KEV11638.1 | | | | | | |
| KEV12282.1 | | | | | | |
| KEV14240.1 | | | | | | |
| KEV21793.1 | | | | | | |
| KEV22298.1 | | | | | | |
| KEV26044.1 | | | | | | |
| KEV32026.1 | | | | | | |
| KEV32063.1 | | | | | | |
| KEV35626.1 | | | | | | |
| KEV42967.1 | | | | | | |
| KEV44621.1 | | | | | | |
| KEV49515.1 | | | | | | |
| KEV49947.1 | | | | | | |
| KEV52716.1 | | | | | | |
| KEV53451.1 | | | | | | |
| KEV60716.1 | | | | | | |
| KEV63470.1 | | | | | | |
| KEV71076.1 | | | | | | |
| KEV74160.1 | | | | | | |
| KEV76378.1 | | | | | | |
| KEV76776.1 | | | | | | |
| KEV79179.1 | | | | | | |
| KEV81224.1 | | | | | | |
| KEV88927.1 | | | | | | |
| KEV93759.1 | | | | | | |
| KEV95283.1 | | | | | | |
| KEW03640.1 | | | | | | |
| KEW09573.1 | | | | | | |
| KEW18769.1 | | | | | | |
| KEW19179.1 | | | | | | |
| KEW21604.1 | | | | | | |
| KEW27010.1 | | | | | | |
| KEW31226.1 | | | | | | |
| KEW33386.1 | | | | | | |
| KEW36305.1 | | | | | | |
| KEW42387.1 | | | | | | |
| KEW44715.1 | | | | | | |
| KEW57718.1 | | | | | | |
| KEW65692.1 | | | | | | |
| KEW66741.1 | | | | | | |
| KEW71344.1 | | | | | | |
| KEW71596.1 | | | | | | |
| KEW72422.1 | | | | | | |
| KEW77363.1 | | | | | | |

TABLE S1-continued acrIIA Gene Conservation, Related to FIGS. 1B 4B and 4C
genomes that lack cas9 and all known acrIIA genes 264
genomes that contain cas9 but lack all known acrIIA genes 33
genomes contain cas9 and acrIIA genes 37
genomes that lack cas9, but contain acrIIA genes 65
unpaired acr genes

| control (cysS) | acrIIA3 | acrIIA2 | acrIIA1 | acrIIA4 | Cas9 | ST strains |
|---|---|---|---|---|---|---|
| KEW79497.1 | | | | | | |
| KEW80113.1 | | | | | | |
| KEW84366.1 | | | | | | |
| KEW93848.1 | | | | | | |
| KEW95807.1 | | | | | | |
| KEW96317.1 | | | | | | |
| KEX09756.1 | | | | | | |
| KEX11628.1 | | | | | | |
| KEX19359.1 | | | | | | |
| KEX20220.1 | | | | | | |
| KEX23616.1 | | | | | | |
| KEX29531.1 | | | | | | |
| KEX29582.1 | | | | | | |
| KEX33273.1 | | | | | | |
| KEX39294.1 | | | | | | |
| KEX42941.1 | | | | | | |
| KEX46988.1 | | | | | | |
| KEX50326.1 | | | | | | |
| KEX51799.1 | | | | | | |
| KEX64668.1 | | | | | | |
| KEX68538.1 | | | | | | |
| KEX69000.1 | | | | | | |
| KEX72953.1 | | | | | | |
| KEX73328.1 | | | | | | |
| KEX77547.1 | | | | | | |
| KEX82199.1 | | | | | | |
| KFZ71375.1 | | | | | | |
| KGJ75182.1 | | | | | | |
| KGJ80867.1 | | | | | | |
| KGR20308.1 | | | | | | |
| KHK07430.1 | | | | | | |
| KHK19170.1 | | | | | | |
| KHK26142.1 | | | | | | |
| KHK36612.1 | | | | | | |
| KHQ60145.1 | | | | | | |
| KHQ69332.1 | | | | | | |
| KHS60750.1 | | | | | | |
| KHS61164.1 | | | | | | |
| KID14246.1 | | | | | | |
| KJH24122.1 | | | | | | |
| KJJ89955.1 | | | | | | |
| KJQ79905.1 | | | | | | |
| KJQ83378.1 | | | | | | |
| KKF72182.1 | | | | | | |
| KKO43304.1 | | | | | | |
| KNX50880.1 | | | | | | |
| KNX54024.1 | | | | | | |
| KNX58068.1 | | | | | | |
| KNX62105.1 | | | | | | |
| KNX63287.1 | | | | | | |
| KNX66597.1 | | | | | | |
| KNX70553.1 | | | | | | |
| KNX72130.1 | | | | | | |
| KOX87096.1 | | | | | | |
| KPJ27561.1 | | | | | | |
| KQC81886.1 | | | | | | |
| KQC82004.1 | | | | | | |
| KRJ93270.1 | | | | | | |
| KRW87784.1 | | | | | | |
| KSZ43192.1 | | | | | | |
| KSZ44687.1 | | | | | | |
| KSZ45883.1 | | | | | | |
| KSZ48351.1 | | | | | | |
| KTA43969.1 | | | | | | |
| KXF63597.1 | | | | | | |
| KXS57277.1 | | | | | | |
| KXS68541.1 | | | | | | |
| KXS69730.1 | | | | | | |
| KXS75040.1 | | | | | | |
| KXS83236.1 | | | | | | |
| KXW87734.1 | | | | | | |

TABLE S1-continued

| acrIIA Gene Conservation, Related to FIGS. 1B 4B and 4C<br>genomes that lack cas9 and all known acrIIA genes 264<br>genomes that contain cas9 but lack all known acrIIA genes 33<br>genomes contain cas9 and acrIIA genes 37<br>genomes that lack cas9, but contain acrIIA genes 65<br>unpaired acr genes | | | | | | |
|---|---|---|---|---|---|---|
| control (cysS) | acrIIA3 | acrIIA2 | acrIIA1 | acrIIA4 | Cas9 | ST strains |
| KXW89246.1 | | | | | | |
| KXW94597.1 | | | | | | |
| KXW97284.1 | | | | | | |
| KXX00507.1 | | | | | | |
| KXX03707.1 | | | | | | |
| KXX09006.1 | | | | | | |
| KXX14888.1 | | | | | | |
| KXX23313.1 | | | | | | |
| KXX28906.1 | | | | | | |
| KXX32727.1 | | | | | | |
| KXX35528.1 | | | | | | |
| KXX37642.1 | | | | | | |
| KXX42799.1 | | | | | | |
| KYB35881.1 | | | | | | |
| KYB36139.1 | | | | | | |
| KYB36717.1 | | | | | | |
| KYB42077.1 | | | | | | |
| KYB43947.1 | | | | | | |
| SLCC5850 was no included in the conservation pattern analysis | | | | | | |
| CBY50703.1 | CBY51763.1 | CBY51762.1 | CBY51761.1 | | CBY53074.1 | slcc5850 |

Previous HTH-containing anti-CRISPR associated (aca) genes were used as markers to identify novel type I anti-CRISPR genes (Pawluk, A. et al. (2016). *Nature Microbiology,* 1, 1-6), although the aca genes did not have anti-CRISPR activity themselves. We hypothesized that acrIIA1 could fulfill the role of such a marker. A comprehensive phylogenetic analysis of acrIIA1 was conducted, revealing homologs detected widely across Firmicutes, in both mobile elements and core genomes (FIG. 4A). A family of distantly related acrIIA1 homologs were identified in *Listeria* genomes, exemplified by orfD, an HTH-containing gene that had been independently identified as an acr locus member (FIG. 3A). While this gene lacked anti-CRISPR activity in a functional assay, its co-occurrence with acrIIA4 in plasmid pLMIV suggests that the broad acrIIA1/orfD superfamily could be used as a marker to identify new acr genes (FIG. 3A). Future work will be necessary to determine whether the HTH-containing genes in these systems serve as effective markers for novel anti-CRISPR discovery.

To determine the homology landscape of acrIIA2-4, similar phylogenetic analyses were performed. Unlike acrIIA1, which was widespread across Firmicutes core genomes, these other three acr genes were mostly restricted to prophages in *Listeria*. Three distinct sequence families of acrIIA2 were identified, found only within *Listeria* siphophages (a family of long tailed, non-contractile phages) (FIG. 4B), while two acrIIA3 families were observed in the genomes of siphophages *Listeria* and *Streptococcus* (FIG. 4C). Lastly, acrIIA4 was observed in two distinct sequence families, one in *Listeria* siphophages and plasmids, and the other in a group of obligate virulent myophages (long contractile tailed phages) (FIG. 4D). While acrIIA2 and acrIIA3 were nearly always found with acrIIA1, acrIIA4 often occurred in the absence of acrIIA1 homologs in phages and mobile elements of *Listeria*. For example, the family of acrIIA4 in virulent phages are distinct in that they have an ~70 amino acid C-terminal extension in the predicted protein and do not occur with the HTH-containing genes acrIIA1 or orfD, suggesting potential mechanistic and evolutionary distinctions between these acrIIA4 families. Together, these analyses reveal ample sequence space for surveying homologous acr genes for specificity determinants and suggest an active arms race between cas9 and mobile elements in *L. monocytogenes.*

AcrIIA2, AcrIIA3, and AcrIIA4 Inhibit *S. pyogenes* Cas9

To determine the versatility of the Lmo Cas9 AcrIIA proteins, we asked whether these inhibitors were functional on the related Cas9 protein from *S. pyogenes* (Spy, 53% identical to Lmo Cas9). This ortholog has been used widely for biotechnological applications as an RNA-guided nuclease (Barrangou, R., and Doudna, J. A. (2016), *Nature Biotechnology,* 34, 933-941), as well as for programmable gene repression by a catalytically deactivated mutant (dCas9) for programmable gene repression (Gilbert, L. A. et al. (2013). *Cell* 154, 442-451; Qi, L. S. et al. (2013). *Cell,* 152, 1173-1183). Using an *E. coli* strain that carries Spy dCas9, we tested whether AcrIIA proteins block dCas9 from interfering with transcription of a chromosomal RFP reporter gene (FIG. 5A). In a genetic background lacking inhibitors, the presence of an sgRNA and dCas9 reduced RFP fluorescence to 2.6% relative to a strain with no guide RNA. acrIIA2 partially blocked dCas9 function with fluorescence rising to 25%, while acrIIA4 nearly completely blocked dCas9, with fluorescence at 85% of the no guide control (FIG. 5B). We could not obtain meaningful data from acrIIA3 because the protein was toxic to *E. coli*. This lowered the recorded cell count during flow cytometry (see FIG. 10*a*) and lead to large variability in the fluorescence measurements. A homolog of AcrIIA3 from *S. pyogenes* (accession number: AND04610.1) with 45% sequence identity to Lmo_acrIIA3 was also tested, but resulted in impaired growth of *E. coli* (FIG. 10*b*). The mechanism of acrIIA3 toxicity remains to be determined. We conclude the acrIIA2 and acrIIA4 inhibit Spy dCas9 in *E. coli* to different degrees.

Given the common application of Spy Cas9 in eukaryotic cells, we next tested the AcrIIA proteins for their ability to block gene editing in human cells. HEK293T cells with an inducible eGFP reporter gene were transiently transfected with a plasmid expressing both Spy Cas9 and an sgRNA targeting eGFP in the presence or absence of vectors expressing human codon optimized AcrIIA proteins. After allowing gene editing to proceed for 36 h, eGFP was induced for 12 h, and cellular fluorescence was then measured by flow cytometry (FIG. 5C). In the presence of Cas9 and the eGFP sgRNA, gene editing resulted in a 25% decrease in the number of GFP positive cells, while co-expression with acrIIA2 or acrIIA4 prevented Cas9-based gene editing (FIG. 5D). We additionally tested the *S. pyogenes* homolog of acrIIA3 (Spy_acrIIA3) in this assay, which was not toxic in human cells, but had no impact on Cas9 function. acrIIA1 was non-functional in human cells, as was orfA, a negative control that has no anti-CRISPR activity in *L. monocytogenes*. Taken together with dCas9 experiments in *E. coli*, these data demonstrate the utility of the AcrIIA2 and AcrIIA4 proteins to inhibit the function of an orthologous Cas9 in heterologous hosts. These reagents, therefore, represent new tools in the CRISPR-Cas9 genome engineering toolkit.

DISCUSSION

Phage-encoded inhibitors of bacterial immune systems emerge due to the strong selective pressures in the evolutionary arms race between these two entities (Samson, J. E. et al. (2013). *Nat Rev Micro,* 11, 675-687). The first identification of phage encoded anti-CRISPRs in type I CRISPR-Cas systems hinted that more CRISPR inhibitors existed, but methods were lacking for their discovery. Here, we present a bioinformatics strategy that uses "self-targeting" as a genomic marker for CRISPR-Cas inhibitor genes (FIG. 1A). This approach led to the identification of four different type II-A CRISPR-Cas9 inhibitors (FIG. 3A), which are collectively present in half of all Cas9-encoding *L. monocytogenes* genomes, including all genomes with self-targeting (FIG. 3C). We anticipate that this approach will be helpful for identifying acr genes in other CRISPR-Cas systems, although a distinct mechanism for tolerance of self-targeting has been described for type III systems (Goldberg, G. W. et al. (2014). *Nature* 514, 633-637; Samai, P. et al. (2015). *Cell,* 161, 1164-1174).

To facilitate the identification of AcrIIA proteins, we first demonstrate a functional CRISPR-Cas9 system in *L. monocytogenes* (FIG. 2B). Previous studies of CRISPR-Cas in this organism have focused on the type I-B system and an associated I-B derived CRISPR orphan array lacking cas genes (Mandin, P. et al. (2007). *Nucleic Acids Research,* 35, 962-974; Sesto, N. et al. (2014). *PLoS Genet,* 10, e1004065). Although no canonical CRISPR-Cas function had been established for either system previously, the orphan array was shown to be processed by a host ribonuclease to generate non coding RNAs (Mandin, P. et al. (2007). *Nucleic Acids Research,* 35, 962-974; Sesto, N. et al. (2014). *PLoS Genet,* 10, e1004065). To observe function for the II-A CRISPR-Cas system, we used a standard transformation efficiency assay, showing that Cas9 function in strain 10403s is sufficient to limit transformation of a plasmid in a sequence specific manner (FIG. 2A-C). Given the small colony phenotype observed during transformation of 10403s with pT, we suspect that endogenous levels of cas9 expression are not sufficient to totally clear the plasmid, leading to maintained plasmid in a tiny colony. Confirming this, increased expression of cas9 resulted in a complete elimination of transformants in this assay (FIG. 2C). Given that ϕJ0161a can inhibit this overexpressed CRISPR-Cas9 system (FIG. 2C), we conclude that the identified inhibitors are able to block both endogenous and overexpressed Cas9 function.

To identify candidate anti-CRISPR genes, related prophages from CRISPR-active strain 10403s to a prophage that inhibits CRISPR from strain J0161 were compared, and a process of elimination cloning approach was taken (FIG. 2D). The identification of two isolated acr genes was confirmed for acrIIA1 and acrIIA2 genes that are present in ϕJ0161. In searching for more anti-CRISPRs, we find that conserved genomic positioning in related phages is a good proxy for identifying distinct type II-A Cas9 inhibitor proteins, despite a lack of sequence conservation between the proteins themselves (FIG. 3A). This has been observed previously in studies of Type I-F and I-E anti-CRISPRs (Bondy-Denomy et al. (2013). *Nature,* 493, 429-432; Pawluk, A. et al. (2014). *mBio* 5, e00896). In *L. monocytogenes*, the high prevalence of Cas9 inhibitors in prophages suggests the widespread inactivation of CRISPR-Cas9 function (FIG. 3C). At present, we do not understand whether there is a mechanistic link to explain the common co-occurrence of acrIIA1 with other anti-CRISPRs (FIGS. 3A and 3B). Although this gene is sufficient to inactivate CRISPR-Cas9 function in a plasmid challenge assay, we speculate that it could act as a co-factor or regulator of other acrIIA genes during infection or lysogeny, thus explaining the genomic associations observed. Future work will be necessary to understand whether AcrIIA1 is, in fact, a bi-functional protein in this regard and more broadly, whether the superfamily is a marker for acr genes.

Phylogenetic analyses demonstrate common occurrences of acrIIA2-4 in mobile elements in *Listeria* mobile elements (FIG. 4). This likely facilitates horizontal gene transfer in this organism by blocking Cas9-based targeting and adaptation (Heler, R. et al. (2015) *Nature* 519, 199-202). In addition to the family of prophages where these acrIIA genes were first identified, homologs were also found in distant siphophages, myophages and plasmids. Most notably, the acrIIA4 homologs encoded by virulent myophages did not have acrIIA1 superfamily homologs in their vicinity. Furthermore, the presence of acrIIA1 and acrIIA3 homologs in genera outside of *Listeria* demonstrates that CRISPR-Cas9 inactivation may be common-place in the Firmicutes.

To inactivate CRISPR-Cas9 function, many mechanisms are possible, in theory. By demonstrating the efficacy of acrIIA2 and acrIIA4 in heterologous hosts with engineered elements (i.e. cas9 promoter, sgRNA design and promoter) we conclude that transcriptional repression is unlikely. Type I anti-CRISPRs function by binding directly to the Cas proteins required for interference and preventing DNA binding or DNA cleavage (Bondy-Denomy, J et al. (2015). *Nature,* 526, 136-139). By extension, we expect a similar mechanism for acrIIA2 and acrIIA4, given their ability to function in human cells. The enhanced efficacy of acrIIA2 in the cleavage-based Cas9 assay in human cells relative to the dCas9 based assay suggests that it may inhibit both binding and cleavage to some degree, with cleavage inhibition manifesting as a full inactivation of Cas9 function. In the case of AcrIIA4, DNA-binding is clearly inhibited, although whether this is through a direct interaction with Cas9 remains to be seen.

The identification and future mechanistic dissection of type II-A inhibitors will provide valuable new reagents for studying canonical CRISPR-Cas9 function in natural and engineered settings. The ability of AcrIIA proteins to block Spy Cas9 in *E. coli* and human cells suggests that these proteins can provide a post-translational "off-switch" for Cas9. This could add a layer of regulation on this powerful system that can be applied in eukaryotic systems to control genome engineering. This new addition to the CRISPR-Cas9 toolbox could enable new applications, such as specifically reversing the effects of dCas9 binding to a genomic locus, or limiting the amount of time that Cas9 is active in the nucleus to reduce off-target gene editing. It will be important to expand the search for inhibitor proteins to continue to exploit the abundant tools provided to us from the phage-bacteria arms race.

| REAGENT or RESOURCE | SOURCE | IDENTIFIER |
|---|---|---|
| | Experimental Models: Cell Lines | |
| HEK293T | ATCC | N/A |
| | Experimental Models: Organisms/Strains | |
| *Listeria monocytogenes* 10403s | Laboratory of Daniel Portnoy | ncbi.nlm.nih.gov/Taxonomy/Browser/wwwtax.cgi?mode=Info&id=393133&lvl=3&lin=f&keep=1&srchmode=1&unlock |
| *Listeria monocytogenes* 10403s derivatives | this paper | see Table S2 |
| *Listeria monocytogenes* J0161 | Laboratory of Martin Wiedmann | ncbi.nlm.nih.gov/Taxonomy/Browser/wwwtax.cgi?id=393130 |
| *Listeria monocytogenes* SLCC2482 | Ariane Pietzka | ncbi.nlm.nih.gov/Taxonomy/Browser/wwwtax.cgi?id=863767 |
| *Listeria monocytogenes* SLCC2540 | Ariane Pietzka | ncbi.nlm.nih.gov/Taxonomy/Browser/wwwtax.cgi?id=879089 |
| *Escherichia coli* BW25113 derivatives | this paper | see Table S2 |
| | Recombinant DNA | |
| pBAD24 | Laboratory of Carol Gross | ncbi.nlm.nih.gov/nuccore/X81837.1 |
| pBAD24-derivative plasmids | this paper | see Table S2 |
| pdCas9-bacteria | Addgene | addgene.org/vector-database/44249/ |
| PLVX-TetOne-Puro | Clontech | clontech.com/US/Products/Inducible__Systems/TetSystems__Product__Overview/Tet-One__Overview |
| pMD2.G | Addgene | addgene.org/12259/ |
| pX330 | Addgene | addgene.org/vector-database/42230/ |
| pcDNA3.1(+) | Addgene | addgene.org/vector-database/2093/ |
| pKSV7 | Laboratory of Daniel Portnoy | addgene.org/26686/ |
| pKSV7-derivative plasmids | this paper | see Table S2 |
| pPL2oexL | Laboratory of Daniel Portnoy | see FIG. 11 |
| pPL2oexL-derivative plasmids | this paper | see Table S2 |
| | Sequence-Based Reagents | |
| I. GeneBlocks for HEK293T expression of phage proteins | IDT | II. see Table S3 |
| | Software and Algorithms | |
| Prism 5 | GraphPad | graphpad.com/scientific-software/prism/ |
| CRISPRfinder | I2BC | crispr.i2bc.paris-saclay.fr/Server/ |
| CRISPRDetect | Univsersity of Otago | brownlabtools.otago.ac.nz/CRISPRDetect/predict__crispr__array.html |
| CRISPRtarget | Univsersity of Otago | bioanalysis.otago.ac.nz/CRISPRTarget/crispr__analysis.html |
| illustrator | adobe | adobe.com/Illustrator |
| MEGA6 | MEGA | megasoftware.net/ |
| Image Lab 5.2.1 | BioRad | bio-rad.com/en-cn/product/image-lab-software |
| FlowJo | FlowJo LLC | flowjo.com/ |

TABLE S2

| Strains and Plasmids, | | | | | |
|---|---|---|---|---|---|
| strain ID | species | strain | genotype | plasmid | drug res. |
| (RAU###, pRAU###) | | | | | |
| 1 | Lmo | 10403S | wt | — | — |
| 3 | *E. coli* | DH5a | — | pKSV7 | $amp_{100}$ |

TABLE S2-continued

| Strains and Plasmids, | | | | | |
|---|---|---|---|---|---|
| 13 | Lmo | SLCC2482 | wt | — | — |
| 14 | Lmo | SLCC2540 | wt | — | — |
| 19 | Lmo | J0161 | wt | — | — |
| 29 | *E. coli* | DH5a | — | pKSV7-S1$_{J0161}$ | amp$_{100}$ |
| 31 | *E. coli* | DH5a | — | pKSV7-S1$_{10403S}$ | amp$_{100}$ |
| 57 | Lmo | 10403S | ϕ10403S cure (ComK$^{+}$) | — | — |
| 46 | *E. coli* | DB3.1 | — | pPL2xoeL | chlor$_{34}$ |
| 71 | Lmo | 10403S | ΔComK::ϕJ0161a | — | — |
| 100 | *E. coli* | NEB5alpha | — | pPL2oexL-ϕJ0161a-frag6 | chlor$_{34}$ |
| 101 | *E. coli* | NEB5alpha | — | pPL2oexL-ϕJ0161a-frag7 | chlor$_{34}$ |
| 102 | *E. coli* | NEB5alpha | — | pPL2oexL-ϕJ0161a-frag9 | chlor$_{34}$ |
| 103 | *E. coli* | NEB5alpha | — | pPL2oexL-ϕJ0161a-frag10 | chlor$_{34}$ |
| 104 | *E. coli* | NEB5alpha | — | pPL2oexL-ϕJ0161a-frag5 | chlor$_{34}$ |
| 105 | *E. coli* | NEB5alpha | — | pPL2oexL-ϕJ0161a-frag3 | chlor$_{34}$ |
| 106 | *E. coli* | NEB5alpha | — | pPL2oexL-ϕJ0161a-frag1 | chlor$_{34}$ |
| 107 | *E. coli* | DH5a | — | pKSV7-ΔCas9 | amp$_{100}$ |
| 109 | *E. coli* | NEB5alpha | — | pPL2oexL-ϕJ0161a-frag8 | chlor$_{34}$ |
| 111 | *E. coli* | NEB5alpha | — | pPL2oexL-ϕJ0161a-frag2 | chlor$_{34}$ |
| 112 | Lmo | 10403S | ComK$^{+}$, ΔtRNA$^{Arg}$::pRAU100 | — | tet$_{2}$ |
| 113 | Lmo | 10403S | ComK$^{+}$, ΔtRNA$^{Arg}$::pRAU101 | — | tet$_{2}$ |
| 114 | Lmo | 10403S | ComK$^{+}$, ΔtRNA$^{Arg}$::pRAU102 | — | tet$_{2}$ |
| 115 | Lmo | 10403S | ComK$^{+}$, ΔtRNA$^{Arg}$::pRAU103 | — | tet$_{2}$ |
| 116 | Lmo | 10403S | ComK$^{+}$, ΔtRNA$^{Arg}$::pRAU105 | — | tet$_{2}$ |
| 117 | Lmo | 10403S | ComK$^{+}$, ΔtRNA$^{Arg}$::pRAU106 | — | tet$_{2}$ |
| 118 | Lmo | 10403S | ComK$^{+}$, ΔtRNA$^{Arg}$::pRAU109 | — | tet$_{2}$ |
| 120 | *E. coli* | NEB5alpha | — | pPL2oexL-Cas9 | chlor$_{34}$ |
| 123 | *E. coli* | NEB5alpha | — | pPL2oexL-ϕJ0161a-frag4 | chlor$_{34}$ |
| 128 | Lmo | 10403S | ComK$^{+}$, ΔtRNA$^{Thr}$::pRAU104 | — | tet$_{2}$ |
| 130 | Lmo | 10403S | ComK$^{+}$, ΔCas9 | — | — |
| 142 | Lmo | 10403S | ΔComK::ϕJ0161a ΔCas9 | — | — |
| 144 | Lmo | 10403S | ComK$^{+}$, ΔCas9 ΔtRNA$^{Arg}$::pRAU120 ΔComK::ϕJ0161a ΔCas9 | — | tet$_{2}$ |
| 151 | Lmo | 10403S | ΔtRNAArg::pRAU120 | — | tet$_{2}$ |
| 153 | *E. coli* | NEB5alpha | — | pPL2oexL-LMOG__03145 | chlor$_{34}$ |
| 155 | *E. coli* | NEB5alpha | — | pPL2oexL-LMOG__03146 | chlor$_{34}$ |
| 157 | *E. coli* | NEB5alpha | — | pPL2oexL-LMOG__03147 | chlor$_{34}$ |
| 159 | Lmo | 10403S | ComK$^{+}$, ΔtRNA$^{Arg}$::pRAU153 | — | tet$_{2}$ |
| 160 | Lmo | 10403S | ComK$^{+}$, ΔtRNA$^{Arg}$::pRAU155 | — | tet$_{2}$ |
| 161 | Lmo | 10403S | ComK$^{+}$, ΔtRNA$^{Arg}$::pRAU157 | — | tet$_{2}$ |
| 162 | *E. coli* | NEB5alpha | — | pPL2oexL-LMOG__03148 | chlor$_{34}$ |
| 165 | Lmo | 10403S | ComK$^{+}$, tRNAArg::pRAU162 | — | tet$_{2}$ |
| 167 | *E. coli* | DH5a | — | pBAD24 | amp$_{100}$ |
| 168 | *E. coli* | NEB5alpha | — | pBAD24-LMOG__03146 | amp$_{100}$ |
| 171 | *E. coli* | NEB5alpha | — | pBAD24-LMOG__03147 | amp$_{100}$ |
| 173 | *E. coli* | NEB5alpha | — | pBAD24-LMOG__03148 | amp$_{100}$ |
| 233 | *E. coli* | NEB5alpha | — | pKSV7-ΔLMOG__03146-7 | amp$_{100}$ |
| 239 | Lmo | 10403S | ComK$^{+}$; tRNAArg::pCW3 | — | tet$_{2}$ |
| 241 | Lmo | 10403S | ComK$^{+}$; tRNAArg::pCW7 | — | tet$_{2}$ |
| 243 | Lmo | 10403S | ComK$^{+}$; tRNAArg::pCSW9 | — | tet$_{2}$ |
| 246 | Lmo | 10403S | ΔComK::phi__J0161a ΔacrIIA1-2 | — | — |
| 257 | Lmo | 10403S | ComK$^{+}$; tRNAArg::pCSW29 | — | tet$_{2}$ |
| 259 | Lmo | 10403S | ComK$^{+}$; tRNAArg::pCSW33 | — | tet$_{2}$ |
| 260 | Lmo | 10403S | ComK$^{+}$; tRNAArg::pCSW35 | — | tet$_{2}$ |
| (CSW##, pCSW##) | | | | | |
| 3 | *E. coli* | NEB5alpha | — | pPL2oexL-lmoslcc2482__0685 | chlor$_{34}$ |
| 7 | *E. coli* | NEB5alpha | — | pPL2oexL-lmoslcc2540__1277 | chlor$_{34}$ |
| 9 | *E. coli* | NEB5alpha | — | pPL2oexL-LMOG__02993 | chlor$_{34}$ |
| 13 | *E. coli* | NEB5alpha | — | pBAD24- lmoslcc2482__0685 | amp$_{100}$ |
| 18 | *E. coli* | NEB5alpha | — | pBAD24-lmoslcc2540__1277 | amp$_{100}$ |
| 21 | *E. coli* | NEB5alpha | — | pBAD24-LMOG__02993 | amp$_{100}$ |
| 26 | *E. coli* | NEB5alpha | — | pBAD24- Axk13__03345 | amp$_{100}$ |
| 29 | *E. coli* | NEB5alpha | — | pPL2oexL-lmoslcc2482__0688 | chlor$_{34}$ |
| 33 | *E. coli* | NEB5alpha | — | pPL2oexL-lmoslcc2540__1278 | chlor$_{34}$ |
| 35 | *E. coli* | NEB5alpha | — | pPL2oexL-LMOG__02992 | chlor$_{34}$ |
| 65 | *E. coli* | NEB5alpha | — | pBAD24-lmoslcc2482__0688 | amp$_{100}$ |
| (MS##) | | | | | |
| 101 | *E. coli* | BW25113 | — | — | |
| 161 | *E. coli* | BW25113 | nfsA::mrfp | — | kan$_{30}$ |
| 243 | *E. coli* | BW25113 | nfsA::mrfp, λatt::pCs550-r | — | kan$_{30}$, chlor$_{20}$ |
| 270 | *E. coli* | BW25113 | nfsA::mrfp, Tn7att::spy-dcas9 | — | kan$_{30}$, gent$_{10}$ |
| 271 | *E. coli* | BW25113 | nfsA::mrfp, λatt::pCs550-r, Tn7att::spy-dcas9 | — | kan$_{30}$, chlor$_{20}$, gent$_{10}$ |
| 270-262 | *E. coli* | BW25113 | nfsA::mrfp, Tn7att::spy-dcas9 | pBAD24 | kan$_{30}$, gent$_{10}$, amp$_{100}$ |

TABLE S2-continued

| Strains and Plasmids, | | | | | |
|---|---|---|---|---|---|
| 270-168 | *E. coli* | BW25113 | nfsA::mrfp, Tn7att::spy-dcas9 | pRAU168 | $kan_{30}$, $gent_{10}$, $amp_{100}$ |
| 270-171 | *E. coli* | BW25113 | nfsA::mrfp, Tn7att::spy-dcas9 | pRAU171 | $kan_{30}$, $gent_{10}$, $amp_{100}$ |
| 270-173 | *E. coli* | BW25113 | nfsA::mrfp, Tn7att::spy-dcas9 | pRAU173 | $kan_{30}$, $gent_{10}$, $amp_{100}$ |
| 270-13 | *E. coli* | BW25113 | nfsA::mrfp, Tn7att::spy-dcas9 | pCSW13 | $kan_{30}$, $gent_{10}$, $amp_{100}$ |
| 270-18 | *E. coli* | BW25113 | nfsA::mrfp, Tn7att::spy-dcas9 | pCSW18 | $kan_{30}$, $gent_{10}$, $amp_{100}$ |
| 270-21 | *E. coli* | BW25113 | nfsA::mrfp, Tn7att::spy-dcas9 | pCSW21 | $kan_{30}$, $gent_{10}$, $amp_{100}$ |
| 270-26 | *E. coli* | BW25113 | nfsA::mrfp, Tn7att::spy-dcas9 | pCSW26 | $kan_{30}$, $gent_{10}$, $amp_{100}$ |
| 270-65 | *E. coli* | BW25113 | nfsA::mrfp, Tn7att::spy-dcas9 | pCSW29 | $kan_{30}$, $gent_{10}$, $amp_{100}$ |
| 271-262 | *E. coli* | BW25113 | nfsA::mrfp, λatt::pCs550-r, Tn7att::spy-dcas9 | pBAD24 | $kan_{30}$, $chlor_{20}$, $gent_{10}$, $amp_{100}$ |
| 271-168 | *E. coli* | BW25113 | nfsA::mrfp, λatt::pCs550-r, Tn7att::spy-dcas9 | pRAU168 | $kan_{30}$, $chlor_{20}$, $gent_{10}$, $amp_{100}$ |
| 271-171 | *E. coli* | BW25113 | nfsA::mrfp, λatt::pCs550-r, Tn7att::spy-dcas9 | pRAU171 | $kan_{30}$, $chlor_{20}$, $gent_{10}$, $amp_{100}$ |
| 271-173 | *E. coli* | BW25113 | nfsA::mrfp, λatt::pCs550-r, Tn7att::spy-dcas9 | pRAU173 | $kan_{30}$, $chlor_{20}$, $gent_{10}$, $amp_{100}$ |
| 271-13 | *E. coli* | BW25113 | nfsA::mrfp, λatt::pCs550-r, Tn7att::spy-dcas9 | pCSW13 | $kan_{30}$, $chlor_{20}$, $gent_{10}$, $amp_{100}$ |
| 271-18 | *E. coli* | BW25113 | nfsA::mrfp, λatt::pCs550-r, Tn7att::spy-dcas9 | pCSW18 | $kan_{30}$, $chlor_{20}$, $gent_{10}$, $amp_{100}$ |
| 271-21 | *E. coli* | BW25113 | nfsA::mrfp, λatt::pCs550-r, Tn7att::spy-dcas9 | pCSW21 | $kan_{30}$, $chlor_{20}$, $gent_{10}$, $amp_{100}$ |
| 271-26 | *E. coli* | BW25113 | nfsA::mrfp, λatt::pCs550-r, Tn7att::spy-dcas9 | pCSW26 | $kan_{30}$, $chlor_{20}$, $gent_{10}$, $amp_{100}$ |
| 271-65 | *E. coli* | BW25113 | nfsA::mrfp, λatt::pCs550-r, Tn7att::spy-dcas9 | pCSW29 | $kan_{30}$, $chlor_{20}$, $gent_{10}$, $amp_{100}$ |

| by genome | | | | | | |
|---|---|---|---|---|---|---|
| 1 alone | 2 alone | 4 alone | 3 alone | 1 + 2 | 1 + 2 + 3 | 1 + 4 |
| 8 | 2 | 11 | 1 | 28 | 48 | 12 |

| by neighborhood | | | | | | |
|---|---|---|---|---|---|---|
| 1 + 2 + 3 | 1 + 2 | 1 alone | 1 + 4 | 4 alone | 2 alone | 3 alone |
| 50 | 29 | 16 | 12 | 11 | 1 | 0 |

| all isolated acrIIA3 | | |
|---|---|---|
| EXL25968.1 | cut off | prophage |

| all isolated acrIIA2 | |
|---|---|
| KXS56902.1 | cut off |
| KXX34219.1 | context unknown; prob not phage |

| all isolated acrIIA4 | | |
|---|---|---|
| EHY61390.1 | arr1a | plasmid (FSL J1208) |
| KXS57719.1 | arr1a | genome |
| KXW85912.1 | arr1a | genome |
| KXS77365.1 | arr1b | genome |
| KXS78354.1 | arr1b | genome |
| KXX11218.1 | arr1b | genome |
| KXX17138.1 | arr1b | genome |
| KXX18287.1 | arr1b | genome |
| KXS56938.1 | arr1c | genome |
| AEH91120.1 | arr2 | prophage |
| ACK40885.1 | arr2 | prophage |

| all isolated acrIIA1 | | |
|---|---|---|
| KTA68177.1 | upstr-orf5 | prophage |
| AGR15693.1 | upstr-orf5 | prophage |
| AGR27297.1 | upstr-orf5 | prophage |
| ALU78083.1 | upstr-orf5 | prophage |
| EEW20426.1 | upstr-orf5 | prophage |
| EFK41083.1 | upstr-orf5 | prophage |
| EZH69029.1 | contig cut off | |
| KHK04755.1 | upstr-orf5 | |
| KHK19909.1 | upstr-orf5 | prophage |
| KHK17523.1 | upstr-orf5 | |
| KTA28092.1 | upstr-orf5 | |
| KXS64534.1 | contig cut off | prophage |
| KHK12400.1 | upstr-orf5 | |
| KKD43688.1 | upstr-orf5 | |
| KLI10251.1 | contig cut off | prophage |
| KTA35071.1 | upstr-orf5 | |

TABLE S2-continued

| Strains and Plasmids, | |
|---|---|
| KTA45326.1 | upstr-orf5 |
| KTA50988.1 | upstr-orf5 |
| KTA63900.1 | upstr-orf5 |

EXPERIMENTAL MODEL AND SUBJECT DETAILS

Microbes.

*Listeria monocytogenes* strains were cultured on Brain-Heart Infusion (BHI) medium. *Escherichia coli* strains were cultured on LB medium.

Cell Lines

Human Embryonic Kidney 293 plus T cell antigen (HEK293T, CRL-3216, ATCC) cells were cultured in Dulbecco's Modified Eagle's Medium (DMEM) supplemented with 10% fetal bovine serum (FBS, Atlanta Biologicals) and 50 μg/mL penicillin/streptomycin (P/S, UCSF CCF).

Example 2

We sought to identify homologs of acrIIA1-4 (FIG. 13) that possess anti-CRISPR function against the *Streptococcus pyogenes* ortholog of Cas9, which is widely used for gene editing.

FIG. 14: AcrIIA1 possesses anti-Cas9 activity in a heterologous system (i.e. outside of natural organism). Previously, this protein did not have anti-Cas9 function in *E. coli* or human cells. The reason for this discrepancy is not yet known, but compared to positive control AcrIIA4, AcrIIA1 functions very well in this heterologous system (*P. aeruginosa*), while targeting Cas9.

FIG. 15: AcrIIA2 homologs were identified via sequence alignments, to broadly sample the natural sequence space. Three homologs were tested in addition to the original protein, and as shown using phage plaque assays in FIG. 16: AcrIIA2b.1 and AcrIIA2b.3 have strong anti-SpyCas9 activity compared to the original protein, AcrIIA2a.

FIG. 17: Similar homology searches were performed to identify AcrIIA3 homologs, AcrIIA3b.2, 3b.3, 3b.4. As shown in FIG. 18 with an assay where bacteria spotted on a plate, these three new anti-CRISPR proteins are not toxic and work robustly in bacteria. AcrIIA4, as identified in the paper is a strong and broad spectrum Cas9 inhibitor that binds tightly to Cas9 (see Dong et al Nature, and Shin et al Science Advances). One homolog (AcrIIA4b) was identified to have modest anti-Cas9 activity.

FIG. 19 summarizes the results described in Example 2.

REFERENCES

Abudayyeh, O. O et al. (2016). *Science* aaf5573

Barrangou, R., and Doudna, J. A. (2016), *Nature Biotechnology,* 34, 933-941

Biswas, A. et al. (2013). *RNA Biol,* 10, 817-827

Biswas, A et al. (2016). *BMC Genomics,* 17, 356

Bondy-Denomy et al. (2013). *Nature,* 493, 429-432

Bondy-Denomy, J et al. (2015). *Nature,* 526, 136-139

Brouns, S. J. J et al. (2008). *Science,* 321, 960-964

Camilli, A., Tilney, L. G., and Portnoy, D. A. (1993). *Molecular Microbiology,* 8, 143-157

Choi, K.-H. et al. (2005). *Nat. Methods,* 2, 443-448

Cong, L. et al. (2013). *Science* 339, 819-823

Deltcheva, E. et al. (2011). *Nature* 471, 602-607

Di, H. et al. (2014) *Biochem Biophys Res Commun,* 454, 399-403

East-Seletsky, A. et al. (2016). *Nature* 538, 270-273

Edgar, R., and Qimron, U. (2010). 192, 6291-6294

Edgar, R. C. (2004). *Nucleic Acids Research,* 32, 1792-1797

Garneau, J. E. et al. (2010). *Nature,* 468, 67-71

Gilbert, L. A. et al. (2013). *Cell* 154, 442-451

Goldberg, G. W. et al. (2014). *Nature* 514, 633-637

Grissa, I., Vergnaud, G., and Pourcel, C. (2007). *Nucleic Acids Research,* 35, W52-W57

Guzman, L. M et al. (1995). *J. Bacteriol.,* 177, 4121-4130

Haldimann, A., and Wanner, B. L. (2001). *J. Bacteriol.,* 183, 6384-6393

Haurwitz, R. E et al. (2010). *Science,* 329, 1355-1358

Heler, R. et al. (2015). *Nature* 519, 199-202

Jinek, M. et al. (2012). *Science,* 337, 816-821

Labrie, S. J., Samson, J. E., and Moineau, S. (2010). *Nat Rev Micro,* 8, 317-327

Lauer, P. et al. (2002). *J. Bacteriol.,* 184, 4177-4186

Loessner, M. J., and Busse, M. (1990). *Applied and Environmental Microbiology,* 56, 1912-1918

Makarova, K. S. et al. (2015). *Nat Rev Micro,* 13, 722-736

Mali, P. et al. (2013). *Science,* 339, 823-826

Mandin, P. et al. (2007). *Nucleic Acids Research,* 35, 962-974

Marraffini, L. A. (2015). CRISPR-Cas immunity in prokaryotes. *Nature,* 526, 55-61

Maxwell, K. L. et al. (2016). *Nature Communications,* 7, 13134

Mojica, F. J. M et al. (2005). *J. Mol. Evol.,* 60, 174-182

Nuñez, J. K. et al. (2014). *Nat. Struct. Mol. Biol* 21, 528-534

Park, S. F., and Stewart, G. S. (1990). *Gene,* 94, 129-132

Pawluk, A. et al. (2014). *mBio* 5, e00896

Pawluk, A. et al. (2016). *Nature Microbiology,* 1, 1-6

Qi, L. S. et al. (2013). *Cell,* 152, 1173-1183

Ran, F. A. et al. (2015). *Cas9.* 520, 186-191

Samai, P. et al. (2015). *Cell,* 161, 1164-1174

Samson, J. E. et al. (2013). *Nat Rev Micro,* 11, 675-687

Sesto, N. et al. (2014). *PLoS Genet,* 10, e1004065

Söding, J., Biegert, A., and Lupas, A. N. (2005). *Nucleic Acids Research,* 33, W244-W248

Tamura, K. et al. (2013). *Mol. Biol. Evol.,* 30, 2725-2729

Typas, A. et al. (2008). *Nat. Methods,* 5, 781-787

Volz, S. E. et al. (2015). *Cell,* 163, 759-771

Wang, X. (2016). *Nat. Struct. Mol. Biol* 23, 868-870

Wright, A. V., Nunez, J. K., and Doudna, J. A. (2016). *Cell,* 164, 29-44

Yosef, I., Goren, M. G., and Qimron, U. (2012). *Nucleic Acids Research,* 40, 5569-5576

Zemansky, J. et al. (2009). *J. Bacteriol.,* 191, 3950-3964

Zetsche, B. et al. (2015). *Cell,* 163, 759-771

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCES
AcrIIA1 protein sequences
>WP_003722518.1 (LMOG_03146)
SEQ ID NO: 1
MTIKLLDEFLKKHDLTRYQLSKLTGISQNTLKDQNEKPLN
KYTVSILRSLSLISGLSVSDVLFELEDIEKNSDDLAGFKH
LLDKYKLSFPAQEFELYCLIKEFESANIEVLPFTFNRFEN
EEHVNIKKDVCKALENAITVLKEKKNELL >WP_060571535.1
SEQ ID NO: 2
MTIKLLDEFLKKHDLTRYQLSKLTGISQNTLKDQNEKPLN
KYTVSILRSLSLISGLSVSDVLFELEDIEKNSDDLAGFKH
LLDKYKLSFPAQEFELYCLIKEFESTNIEVLPFTFNRFEN
EEHVNIKKDVCKALENAITVLKEKKNELL >WP_070783094.1
SEQ ID NO: 3
MTIKLLDEFLKKHDLTRYQLSKLTGISQNTLKDQNEKPLN
KYTVSILRSLSLISGLSVSDVLFELEDIEKNSDDLAGFKH
LLDKYKLSFPAQEFELYCLIKEFESNIEVLPFTFNRFENE
EHVNIGKDVCKALENAITVLKEKKNELL >WP_031669445.1
SEQ ID NO: 4
MTIKLLDEFLKKHDLTRYQLSKLTGISQNTLKDQNEKPLN
KYTVSILRSLSLISGLSVSDVLFELEDIEKNSDDLAGFKH
LLDKYKLSFPAQEFELYCLIKEFESANIEVLPFTFNRFEN
EEHVNIEKDVCKALENAITVLKEKKNELL >WP_070286809.1
SEQ ID NO: 5
MTIKLLDEFLKKHDLTRYQLSKLTGISQNTLKDQNEKPLN
KYTVSILRSLSLISGLSVSDVLFELEDIEKNSDDLAGFKH
LLDKYKLSFPAQEFELYCLIKEFESNIEVLPFTFNRFENE
KHVNIKKDVCKALENAITVLKEKKNELL >WP_070213372.1
SEQ ID NO: 6
MTIKLLDEFLKKHDLTRYQLSKLTGISQNTLKDQNEKPLN
KYTVSILRSLSLISGLSVSDVLFELEDIEKNSDDLAGFKH
LLNKYKLSFPAQEFELYCLIKEFESANIEVLPFTFNRFEN
EEHVNIEKDVCKALENAITVLKEKKNELL >WP_003731275.1
SEQ ID NO: 7
MAIKLLDEFLKKHDLTRYQLSKLTGISQNTLKDQNEKPLN
KYTVSILRSLSLISGLSVSDVLFELEDIEKNSDDLAGFKH
LLDKYKLSFPAQEFELYCLIKEFESANIEVLPFTFNRFEN
EKHVNIKKDVCKALENAITVLKEKKNELL >WP_010989942.1
SEQ ID NO: 8
MSIKLLDEFLKKHNKTRYQLSKLTGISQNTLKDQNEKPLN
KYTVSILRSLSLISGLSVSDVLFELEDIEKNSDDLAGFKH -continued

LLDKYKLSFPAQEFELYCLIKEFESANIEVLPFTFNRFEN
EEHVNIEKDVCKALENAITVLKEKKNELL

>WP_070286796.1
SEQ ID NO: 9
MKLLDEFLKKHDLTRYQLSKLTGISQNTLKDQNEKPLNKY
TVSILRSLSLISGLSVSDVLFELEDIEKNSDDLAGFKHLL
DKYKLSFPAQEFELYCLIKEFESANIEVLPFTFNRFENEK
HVNIKKDVCKALENAITVLKEKKNELL

>WP_038409766.1
SEQ ID NO: 10
MTIKLLDEFLKKHDLTRYQLSKLTGISQNTLKDQNEKPLN
KYTVSILRSLSLISGLSVSDVLFELEDIEKNSDDLAGFKH
LLNKYKLSFPAQEFELYCLIKEFESANIEVLPFTFNRFEN
ETHVDIEKDVRKALENAITVLKEKKNELL

>WP_060595919.1
SEQ ID NO: 11
MTIKLLDEFLKKHDLTRYQLSKLTGISQNTLKDQNEKPLN
KYTVSILRSLSLISGLSVSDVLFELEDIEKNSDDLAGFKH
LLDKYKLSFPAQEFELYCLIKEFESANIEVLPFTFNRFEN
ETHVDIEKDVRKALENAITVLKEKKNELI

>WP_047934203.1
SEQ ID NO: 12
MTIKLLDEFLKKHDLTRYQLSKLTGISQNTLKDQNEKSLN
KYTVSILRSLSLISGLSVSDVLFELEDIEKNSDDLAGFKH
LLGKYKLSFPAQEFELYCLIKEFESANIEVLPFTFNRFEN
ETHVDIEKDVRKALENAITVLKEKKNELI

>YP_009044824.1
SEQ ID NO: 13
MTIKLLDEFLKKHDLTRYQLSKLTGISQNTLKDQNEKPLN
KYTVSILRSLSLISGLSVSDVLFELEDIEKNSDDLAGFKH
LLDKYKLSFPAQEFELYCLIKEFESANIEVLTFTFNRFEN
EEHADIEKDVKKALNNAIAVLKEKKEELL

>WP_061396064.1
SEQ ID NO: 14
MTIKLLDEFLKKHDLTRYQLSKLTGISQNTLKDQNEKSLN
KYTVSILRSLSLISGLSVSDVLFELEDIEKNSDDLAGFKH
LLGKYKLSFPAQEFELYCLIKEFESANIEVLTFTFNRFEN
EEHADIEKDVKKALNNAIAVLKEKKEELL

>WP_014930689.1
SEQ ID NO: 15
MTIKLLDEFLKKHDLTRYQLSKLTGISQNTLKDQNEKSLN
KYTVSILRSLSLISGLSVSDVLFELEDIEKNSDDLAGFKH
LLGKYKLSFPAQEFELYCLIKEFESANIEVLTFTFNRFEN
EEHADIEKDVKKALNNAIAVLKAKKEELL

>WP_061105218.1
SEQ ID NO: 16
MTIKLLDEFLKKHDLTRYQLSKLTGISQNTLKDQNEKSLN
KYTVSILRSLSLISGLSVSDVLFELEDIEKNSDDLAGFKH

-continued

LLGKYKLSFPAQEFELYCLIKEFESANIEVLTFTFNRFEN

EEHADIEKDVKKTLNNAIAVLKEKKEELL

>WP_070216262.1
SEQ ID NO: 17
MTIKLLDEFLKKHDLTRYQLSKLTGISQNTLKDQNEKPLN

KYTVSILRSLSLISGLSVSDVLFELEDIEKNSDDLAGFKH

LLDKYKLSFPAQEFELYCLIKEFESANIEVLTFTFNRFEN

EEHADIEKDVKKALNNAIAVLKEK

>WP_070761486.1
SEQ ID NO: 18
MTIKLLDEFLKKHDLTRYQLSKLTGISQNTLKDQNEKSLN

KYTVSILRSLSLISGLSVSDVLFELEDIEKNSDDLAGFKH

LLGKYKLSFPAQEFELYCLIKEFESANIEVLTFTFNRFEN

EEHADIEKDVKKALNNAIAVLKEKKKNCYKNY

>WP_070005110.1
SEQ ID NO: 19
MSIKLLDEFLKKHDLTRYQLSKLTGISQNTLKDQNEKSLN

KYTVSILRALALITGMPISDVLFELEDLEKNADDLAGFKH

LLDTYKLSFPAQEFELYCLIKEFESANIEVLPFTFNRFES

ETHVDIEKDVRKALENAITVLKEKKNEFM

>WP_070784182.1
SEQ ID NO: 20
MTIKLLDEFLKKHDLTRYQLSKLTGISQNTLKDQNEKPLN

KYTVSILRSLSLISGLSVSDVLFELEDIEKNSDDLAGFKH

LLDKYKLSFPAQEFELYCLIKEFESANIEVLPFTFNRFEN

EEHVNIEKDVCKA

>WP_070776459.1
SEQ ID NO: 21
MSIKLLDEFLKKHDLTRYQLSKLTGISQNTLKDQNEKTLN

KYTVSILRALALITGMPISDVLFELEDLEKNADDLAGFKH

LLDTYKLSFPAQEFELYCLIKEFESANIEVLPFTFNRFES

ETHVDIEKDVQKALENAITVLKEKKNEFM

>WP_003737351.1
SEQ ID NO: 22
MSIKLLDEFLKKHDLTRYQLSKLTGISQNTLKDQNEKTLN

KYTVSILRALALITGMPISDVLFELEDLEKNADDLAGFKQ

LLDTHKLSFPAHEFELYCLIKEFESVNIEVLPFTFNRFES

ETHVDIEKDVRKALENAITVLKEKKNEFM

>WP_010991654.1
SEQ ID NO: 23
MSIKLLDEFLKKHDLTRYQLSKLTGISQNTLKDQNEKTLN

KYTVSILRALALITGMPISDVLFELEDLEKNADDLAGFKQ

LLDTHKLSFPAHEFELYCLIKEFESVNIEVLPFTFNRFES

ETHVDIEKDVRKALENAITVLKEKKNEFI

>WP_070295945.1
SEQ ID NO: 24
MSIKLLDEFLKKHDLTRYQLSKLTGISQNTLKDQNEKTLN

KYTVSILRALALITGMPISDVLFELEDLEKNADDLAGFKQ

-continued

LLDTHKLSFPAHEFELYCLIKEFESVNIEVLPFTFNRFES

ETHVDIEKDVQKALENAIAVLKEKKEELL

>WP_061662200.1
SEQ ID NO: 25
MTIKLLDEFLKKHDLTRYQLSKLTGISQNTLKDQNEKPLN

KYTVSILRSLSLISGLSVSDVLFELEDIEKNSDDLAGFKH

LLDKYKLSFPAQEFELYCLIKEFESANIEVLPFTFNRFEN

EEHVN

>WP_061665494.1
SEQ ID NO: 26
MSIKLLDEFLKKHNKTRYQLSKLTGISQNTLNDYNKKELN

KYSVSFLRALSMCAGISTFDVFIELAELEKSYDDLAGFKH

LLDKYKLSFPAQEFELYCLIKEFESANIEVLPFTFNRFEN

EEHVNIKKDVCKALENAITVLKEKKNELL

>WP_061107167.1
SEQ ID NO: 27
MSIKLLDEFLKKHSKTRYQLSKLTGISQNTLNDYNKKELN

KYSVSFLRALSMCAGISTFDVFIELAELEKSYDDLAGFKH

LLDKYKLSFPAQEFELYCLIKEFESANIEVLPFTFNRFEN

EEHVNIKKDVCKALENAITVLKEKKNELL

>WP_070005290.1
SEQ ID NO: 28
MSIKLLDEFLKKHSKTRYQLSKLTGISQNTLNDYNKKELN

KYSVSFLRALSMCAGISTFDVFIELAELEKSYDDLAGFKH

LLDKYKLSFPAQEFELYCLIKEFESANIEVLPFTFNRFEN

EEHVNIEKDVCKALENAITVLKEKKNELL

>WP_039385152.1
SEQ ID NO: 29
MSIKLLDEFLKKHNKTRYQLSKLTGISQNTLNDYNKKELN

KYSVSFLRALSMCTGISTFDVFIELAELEKSYDDLAGFKH

LLNKYKLSFPAQEFELYCLIKEFDSANIEVLPFTFNRFEN

EEHVNIEKDVCKALENAITVLKEKKNELL

>WP_015967154.1
SEQ ID NO: 30
MSIKLLDEFLKKHSKTRYQLSKLTGISQNTLNDYNKKELN

KYSVSFLRALSMCAGISTFDVFIELAELEKSYDDLAGFKH

LLDKYKLSFPAQEFELYCLIKEFESANIEVLPFTFNRFEN

EEHVNIEKDVCKALENAITVLKEKKNELI

>WP_069001242.1
SEQ ID NO: 31
MNIKLLDEFLKKHNKTRYQLSKLTGISQNTLNDYNKKELN

KYSVSFLRALSMCTGISTFDVFIELAELEKSHDDLAGFKH

LLDKHKLSFPAQEFELYCLIKEFESANIEVLPFTFNRFEN

EEHVNIEKDVCKALENAITVLKEKKNELL

>WP_070040173.1
SEQ ID NO: 32
MSIKLLDEFLKKHDLTRYQLSKLTGISQNTLNDYNKKELN

KYSVSFLRALSMCTGISTFDVLIELAELEKSYDDLAGFKH

-continued

LLDKYKLSFPAQEFELYCLIKEFESANIEVLPFTFNRFEN

ETHVDIEKDVRKALENAITVLKEKKNELI

>WP_068999238.1

SEQ ID NO: 33

MTIKLLDEFLKKHSLTRYQLSKLTGISQNTLNDYNKKELN

KYSVSFLRALSMCAGISTFDVLIELAELEKSYDDLAGFKH

LLDKYKLSFPAQEFELYCLIKEFESANIEVLPFTFNRFEN

ETHVDIEKDVRKALENAITVLKEKKNELI

>WP_070784648.1

SEQ ID NO: 34

MSIKLLDEFLKKHNKTRYQLSKLTGISQNTLNDYNKKELN

KYSVSFLRALSMCAGISTFDVLIELAELEKSYDDLAGFKH

LLDKYKLSFPAQEFELYCLIKEFESANIEVLPFTFNRFEN

ETHVDIEKDVRKALENAITVLKEKKNELI

>WP_070777825.1

SEQ ID NO: 35

MSIKLLDEFLKKHNKTRYQLSKLTGISQNTLNDYNKKELN

KYSVSFLRALSMCAGISTFDVLIELAELEKSYDDLAGFKH

LLDKYKLSFPAQEFELYCLIKEFECANIEVLPFTFNRFEN

ETHVDIEKDVRKALENAITVLKEKKNELI

>WP_047934326.1

SEQ ID NO: 36

MSIKLLDEFLKKHNKTRYQLSKLTGISQNTLNDYNKKELN

KYSVSFLRALSMCAGISTFDVFIELAELEKSYDDLAGFKH

LLDKYKLSFPAQEFELYCLIKEFESANIEVLPFTFNRFEN

ETHVDIEKDVRKALENAITVLKEKKNELI

>WP_003727802.1

SEQ ID NO: 37

MSIKLLDEFLKKHNKTRYQLSKLTGISQNTLNDYNKKELN

KYSVSFLRALSMCTGISTFDVFIELAELEKNYDDLAGFKH

LLDKYKLSFPAQEFELYCLIKEFECANIEVLPFTFNRFEN

ETHVDIEKDVRKALENAITVLKEKKNELI

>WP_003723291.1 (LMOG_02992)

SEQ ID NO: 38

MSIKLLDEFLKKHNKTRYQLSKLTGISQNTLNDYNKKELN

KYSVSFLRALSMCAGISTFDVFNELEELEKNYDDLAGFKH

LLDKYKLSFSAQEFELYCLIKEFESANIEVLPFTFNRFEN

ETHVDIEKDVRKALENAITVLKEKKNELI

>WP_069027465.1

SEQ ID NO: 39

MTIKLLDEFLKKHSKTRYQLSKLTGISQNTLNDYNKKELN

KYSVSFLRALSMCAGISTFDVFIELAELEKSYDDLAGFKH

LLDKYKLSFPAQEFELYCLIKEFECANIEVLPFTFNRFEN

ETHVDIEKDVRKALENAITVLKEKKNELI

>WP_047933338.1

SEQ ID NO: 40

MSIKLLDEFLKKHSKTRYQLSKLTGISQNTLNDYNKKELN

KYSVSFLRALSMCAGISTFDVFIELAELEKSYDDLAGFKH

-continued

LLDKYKLSFPAQEFELYCLIKEFESANIEVLPFTFNRFEN

ETHVDIEKDVRKALENAITVLKEKKNELI

>WP_060579665.1

SEQ ID NO: 41

MSIKLLDEFLKKHSKTRYQLSKLTGISQNTLNDYNKKELN

KYSVSFLRALSMCAGISTFDVFIELAELEKSYDDLAGFKH

LLDKYKLSFPAQEFELYCLIKEFECANIEVLPFTFNRFEN

ETHVDIEKDVRKALENAITVLKEKKNELL

>WP_031646274.1

SEQ ID NO: 42

MTIKLLDEFLKKHDLTRYQLSKLTGISQNTLNDYNKKELN

KYSVSFLRALSMCTGISTFDVFIELAELEKSYDDLAGFKH

LLDKYKLSFPAQEFELYCLIKEFESANIEVLPFTFNRFEN

EEHTDIEKDVKKTLNNAIAVLKEKKEELL

>WP_070776287.1

SEQ ID NO: 43

MSIKLLDEFLKKHNKTRYQLSKLTGISQNTLNDYNKKELN

KYSVSFLRALSMCAGISTFDVFIELAELEKSYDDLAGFKH

LLDKYKLSFPAQEFELYCLIKEFECANIEVLPFTFNRFEN

ETHVDIEKDVRKALENAITVLKEKKNELI

>WP_031645842.1

SEQ ID NO: 44

MSIKLLDEFLKKHSKTRYQLSKLTGISQNTLNDYNKKELN

KYSVSFMRALSMCAGISTFDVFIELAELEKSYDDLAGFKH

LLDKYKLSFPAQEFELYCLIKEFESANIEVLPFTFNRFEN

ETHVDIEKDVRKALENAITVLKEKKNELI

>WP_046376633.1

SEQ ID NO: 45

MSIKLLDEFLKKHNKTRYQLSKLTGISQNTLNDYNKKELN

KYSVSFLRALSMCAGISTFDVFKELEELEKNYDDLAGFKH

LLDKYKLSFSAQEFELYCLIKEFESANIEVLPFTFNRFEN

ETHVDIEKDVRKALENAITVLKEKKNELI

>WP_070242402.1

SEQ ID NO: 46

MSIKLLDEFLKKHSKTRYQLSKLTGISQNTLNDYNKKELN

KYSVSFLRALSMCAGISTFDVFIELAELEKSYDDLSGFKH

LLDKYKLSFPAQEFELYCLIKEFESANIEVLPFTFNRFEN

ETHVDIEKDVRKALENAITVLKEKKNELI

>WP_047923954.1

SEQ ID NO: 47

MSIKLLDEFLKKHSKTRYQLSKLTGISQNTLNDYNKKELN

KYSVSFLRALSMCAGISTFDVFIELAELEKSYDDLAGFKH

LLDKYKLSFPAQEFELYCLIKEFESASIEVLPFTFNRFEN

ETHVDIEKDVRKALENAITVLKEKKNELI

>WP_031668927.1

SEQ ID NO: 48

MSIKLLDEFLKKHNKTRYQLSKLTGISQNTLNDYNKKELN

KYSVSFLRALSMCTGISTFDVFIELAELEKSHDDLAGFKH

LLDKHKLSFPAQEFELYCLIKEFESANIEVLPFTFNRFEN

ETHVDIEKDVRKALENAITVLKEKKNELI

>WP_012581438.1

SEQ ID NO: 49

MSIKLLDEFLKKHSKTRYQLSKLTGISQNTLNDYNKKELN

KYSVSFLRALSMCAGISTFDVFIELAELEKSYDDLAGFKH

LLDKYKLSFPAQEFELYCLIKEFECANIEVLPFTFNRFEN

ETHVDIEKDVRKALENAITVLKEKKNELI

>WP_031667947.1

SEQ ID NO: 50

MSIKLLDEFLKKHSKTRYQLSKLTGISQNTLNDYNKKELN

KYSVSFLRALSMCAGISTFDVFIELAELEKSYDDLAGFKH

LLDKYKLSFPAQEFELYCLIKEFECANIEVLPFTFNRFEN

ETHVDIEKDIRKALENAITVLKEKKNELI

>WP_061107116.1

SEQ ID NO: 51

MSIKLLDEFLKKHNKTRYQLSKLTGISQNTLNDYNKKELN

KYTVSFLRTLSMCVGMSTVDVFIELAELEKNYDDLAGFKH

LLDKYKLSFPAQEFELYCLIKEFESANIEVLPFTFNRFES

ETHVDIEKDVKKALNNAIAVLKEKKEELL

>WP_070783481.1

SEQ ID NO: 52

MSIKLLDEFLKKHSKTRYQLSKLTGISQNTLNDYNKKELN

KYSVSFLRALSMCAGISTFDVFIELAELEKSYDDLAGFKH

LLDKYKLSFPAQEFELYCLIKEFESANIEVLPFTFNRFEN

ETHVDIEKDVRKALNNAIAVLKEKKEELL

>WP_060577773.1

SEQ ID NO: 53

MSIKLLDEFLKKHNKTRYQLSKLTGISQNTLNDYNKKELN

KYSVSFLRALSMCAGISTFDVFIELAELEKSYDDLAGFKY

LLDKHKLSFPAQEFELYCLIKEFESANIEVLPFTFNRFEN

ETHVDIEKDVRKALENAITVLKEKKNELI

>WP_039389295.1

SEQ ID NO: 54

MNIKLLDEFLKKHDLTRYQLSKLTGISQNTLNDYNKKELN

KYSVSFLRALSMCTGISTFDVFIELAELEKSYDDLAGFKH

LLDKHKLSFPAQEFELYCLIKEFESANIEVLPFTFNRFEN

EEHADIEKDVKKALNNAIAVLKAKKEELL

>WP_070295880.1

SEQ ID NO: 55

MSIKLLDEFLKKHDLTRYQLSKLTGISQNTLKDQNEKTLN

KYTVSILRALALITGMPISDVLFELEDLEKNADDLAGFKQ

LLDTHKLSFPAHEFELYCLIKEFESVNIEVLPFTFNRFES

ETHVDIEKDV

>WP_061399219.1

SEQ ID NO: 56

TRYQLSKLTGISQNTLNDYNKKELNKYSVSFLRALSMCAG

ISTFDVFIELAELEKSYDDLAGFKHLLDKYKLSFPAQEFE

LYCLIKEFESANIEVLPFTFNRFENEEHVNIKKDVCKALE

NAITVLKEKKNELL

>WP_061112070.1

SEQ ID NO: 57

MKINLLDEFLKRHNITRYRLSKLAGISQNTLKDYNEKSLN

KYTVSFLRSLSFVTGEDVTDVLIELAELEKGYDDLAGFKY

LLDKYKLSFPALEFELYCIIKEFESANIEISPFTFNRFEN

ETHVDIEKDVKKALQNAVTVLEERKEELL

>WP_070779352.1

SEQ ID NO: 58

MKNNLLDTFLKRHDITRYRLSKLAGISQNTLKDYNEKSLN

KYTVSLLRSLSFVTGESITDVLLELAEIEKDYDDLAGFKY

LLDKYKLSFPALEFELYCIIKEFESANVEISPFTFNRFEN

ETHADIEKDVKKALNNAITVLKEKKEELL

>WP_014930929.1

SEQ ID NO: 59

MSIKLLDEFLKKHNKTRYQLSKLTGISQNTLNDYNKKELN

KYSVSFLRALSMCAGISTFDVFIELAELEKSYDDLAGFKY

LLDKHKLSFPTQEFELYCLIKEFESANIEVLPFTFNRFEN

ETHADIEKDVKKALNNAIAVLEEKKEELL

>WP_069001897.1

SEQ ID NO: 60

MKINLLDAFLKRHNITRYRLSKLAGISQNTLKDYNEKSLN

KYTVSFLRSLSFVTGEDVTDVLIELAELEKGYDDLAGFKY

LLDKYKLAFPALEFELYCLIKEFEAANIEVSPFTFNRFEN

ETHADIEKDVKKALKNAIIVLKEKKEELL

>WP_070784143.1

SEQ ID NO: 61

MSIKLLDEFLKKHSKTRYQLSKLTGISQNTLNDYNKKELN

KYSVSFLRALSMCAGISTFDVFIELAELEKSYDDLAGFKH

LLDKYKLSFPAQEFELYCLIKEFESANIEVLPFTFNRFEN

EEHVNIEKDVCKA

>EFS02359.1

SEQ ID NO: 62

MKINLLDEFLKRHNITRYRLSKLAGISQNTLKDYTEKSLN

KYTVSFLRSLSFATGESVTDILLELAELEKDYDDLAGFKY

LLDKYKLAFPALEFELYCLIKEFESANIEISPFTFNRFES

ETHTDIEKDVKKALQNAVTVLEERKEELL

>WP_061128861.1

SEQ ID NO: 63

MSIKLLDEFLKKHSKTRYQLSKLTGISQNTLNDYNKKELN

KYSVSFLRSLSFATGESVTDILLELAELEKDYDDLAGFKY

LLDKYKLAFPALEFELYCLIKEFESANIEISPFTFNRFES

ETHTDIEKDVKKALQNAVTVLEERKEELL

>KUG37233.1

SEQ ID NO: 64

MSIKLLDEFLKKHNKTRYQLSKLTGISQNTLNDYNKKELN

KYSVSFLRALSMCAGISTFDVFIELAELEKSYDDLAGFKY

-continued

LLDKHKLSFPTQEFELYCLIKEFESANIEVLPFTFNRFEN

ETHADIEKDVKKALNNAIAVLEEKKRRTVIKTIDYYDYS

>WP_049955951.1
SEQ ID NO: 65
MNNFAFITSFNYQQPRYQLSKLTGISQNTLNDYNKKELNK

YSVSFLRALSMCAGISTFDVLIELAELEKSYDDLAGFKHL

LDKYKLSFPAQEFELYCLIKEFESANIEVLPFTFNRFENE

THVDIEKDVRKALENAITVLKEKKNELI

>WP_009917642.1
SEQ ID NO: 66
MKTNLLDTFLKRHGITRYRLSKLAGISQNTLKDYTEKSLN

KYTVSFLRSLSFVTGEDVTDVLLELAEIENGYDDLAGFKY

LLDKYKLSFPALEFELYCIIKEFESANIEISPFTFNRFEN

ETHADIEKDVKKALKNAVTVLEERKEELL

>WP_070777879.1
SEQ ID NO: 67
MNNFAFITSFNYQQPRYQLSKLTGISQNTLNDYNKKELNK

YSVSFLRALSMCAGISTFDVLIELAELEKSYDDLAGFKHL

LDKYKLSFPAQEFELYCLIKEFECANIEVLPFTFNRFENE

THVDIEKDVRKALENAITVLKEKKNELI

>WP_061662201.1
SEQ ID NO: 68
MSIKLLDEFLKKHNKTRYQLSKLTGISQNTLNDYNKKELN

KYSVSFLRALSMCAGISTFDVFIELAELEKSYDDLAGFKH

LLDKYKLSFPAQEFELYCLIKEFESANIEVLPFTFNRFEN

EEHVN

AcrIIA2 protein sequences
>WP_003722517.1
SEQ ID NO: 69
MILTRAQKKYAPAMHEFINMVDDFEESTPDFAKEVLHDSD

YVVITKNEKYAVALCSLSTDECEYDTNLYLDEKLVDYSTV

DVNGVTYVINIVETNDIDDLEIATDEDEMKSONQEIILKS

ELK

>WP_031668925.1
SEQ ID NO: 70
MTLTRAQKKYAEAMHEFINMVDDFEESTPDFAKEVLHDSD

YVVITKNEKYAVALCSLSTDECEYDTNLYLDEKLVDYSTV

DVNGVTYYINIVETNDIDDLEIATDEDEMKSGNQEIILKS

ELN

>WP_031646276.1
SEQ ID NO: 71
MTITRAQKKYAEAMHEFINMVDDFEESTPDFAKEVLHDSD

YVVITKNEKYAVALCSLSTDECEYDTNLYLDEKLVDYSTV

DVNGVTYYINIVETNDIDDLEIATDEDEMKSGNQEIILKS

ELK

>EZH71062.1
SEQ ID NO: 72
KMTLTRAQKKYAEAMHEFINMVDDFEESTPDFAKEVLHDS

DYVVITKNEKYAVALCSLSTDECEYDTNLYLDEKLVDYST

-continued

VDVNGVTYYINIVETNDIDDLEIATDEDEMKSGNQEIILK

SELN

>WP_061662199.1
SEQ ID NO: 73
MTLTRAQKKYAEAMHEFINMVDDFEESTPDFAKEVLHDSD

YVVITKNEKYAVALCSLSTDECEYDTNLYLDEKLVDYSTV

DVNGVTYYINIVETNDIDDLEIATDEDEMKSGNQEIILKS

EL

>WP_070026783.1
SEQ ID NO: 74
MTLTRAQKKYAEAMHEFINMVDDFEESTPDFAKEVLHDSD

YVVITKNEKYAVALCSLSTDECEYDTNLYLDEKLVDYSTV

DVNGVTYYINIVETNDIDDLEIATDEDEMKSDNQEIILKS

ELK

>WP_068996202.1
SEQ ID NO: 75
MTITRAQKKYAEAMHEFINMVDDFEESTPDFAKEVLHDSD

YVVITKNEKYAVALCSLSTDGCEYDTNLYLDEKLVDYSTV

DVNGVTYYINIVETNDIDDLEIATDEDEMKSGNQEIILKS

ELK

>WP_009928183.1
SEQ ID NO: 76
MTLTRAQKKYAEAMHEFINMVDDFEESTPDFAKEVLHDSD

YVVITKNEKYAVALCSLSTDECEYDTNLYLDEKLVDYSTV

DVNGVTYYINIVETKDIDDLEIATDEDEMKSDNQEIILKS

ELK

>WP_014930690.1
SEQ ID NO: 77
MTITTAQKKYAEAMHEFINMVDDFEESTPDFAKEVLHDSD

YVVITKNEKYAVALCSLSTDECEYDTNLYLDEKLVDYSTV

DVNGVTYYINIVETNDIDDLEIATDEDEMKSGNQEIILKS

ELK

>WP_061394923.1
SEQ ID NO: 78
MTITTAQRKYNEAMHEFINMVDDFEESTPDFAKEVLHDSD

YVVITKNEKYAVALCSLSTDECEYDTNLYLDEKLVDYSTV

DVNGVTYYINIVETNDIDDLEIATDEDEMKSGNQEIILKS

ELK

>WP_069001241.1
SEQ ID NO: 79
MTITTAQRKYNEAMHEFINMVDDFEESTPDFAKEVLHDCD

YVVVTKNEKYAVALCTLSTDECEYDTNLYLDEKLVDYSTV

NVNGVTYYINIVETNDIDDLEIATDEDEMKSDNQEIILKS

ELK

>WP_039389299.1
SEQ ID NO: 80
MTITTAQRKYNEAMHEFINMVDDFEESTPDFAKEVLHDCD

YVVVTKNEKYAVALCTLSTDECEYDTNLYLDEKLVDYSTV

-continued

NVNGVTYYINIVETNDIDDLEIATDEDEMKSDNQKIILKS ELK

>WP_039385155.1
SEQ ID NO: 81
MTLTRAQKKYAEAMHEFINMVDDFEESTPDFAKEVLHDSD YVVITKNEKYAVALCSLSTDECEYDTNLYLDEKLVDYSTV DVNGVTYYINIVETKDIDDLEIATDEDKEKHDKQEVIIKS ELN

>WP_003733874.1
SEQ ID NO: 82
MHEFINMVDDFEESTPDFAKEVLHDSDYVVITKNEKYAVA LCSLSTDECEYDTNLYLDEKLVDYSTVDVNGVTYYINIVE TNDIDDLEIATDEDEMKSGNQEIILKSELK

>WP_070294198.1
SEQ ID NO: 83
MTLTRAQKKYAEAMHEFINMVDDFEESKPNFAKEVLHDSD YVVITKNEKYAVALCSLSTDECEYDTNLYLDEKLVDYSTV DVNGVTYYINIVVTNEDDFKLATDKDKEKHDKQEVIVKSE LN

>WP_031649390.1
SEQ ID NO: 84
MTLTTAQRKYNEAMHEFINMVDDFEESTPEFSKEVLNDSD YVVITKNEKYAGALCHVSTDECEDGSNLYIDEKLIDYSTL NVGGVTYYINIVERCEDDLEIATDEDKMKSDNQEIILKNE LN

>EFR93689.1
SEQ ID NO: 85
MVDDFEESTPEFSKEVLNDSDYVVITKNEKYAGALCHVST DECEDGSNLYIDEKLIDYSTLNVGGVTYYINIVERCEDDL EIATDEDKMKSDNQEIILKNELN

>WP_070295879.1
SEQ ID NO: 86
MTLTTAQKRYYDAMNEFEAITSKKLEQTPEFSQDLLNDSD YLVITKNEAYAVALCMLDDDKLYLDETLVQSTCLDVEGET YYINFVVTNEDDFKLATDEDKEKHDKQEVIVKSELN

>WP_070776458.1
SEQ ID NO: 87
MTLTTAQKRYYDAMNEFEAITSKELEQTPEFSQDLLNDSD YLVITKNEAYAVALCMLDDDKLYLDETLVQSTCLDVEGET YYINFVVTNEDDFKLATDEDKEKHDKQEVIVKSELN

>WP_070005111.1
SEQ ID NO: 88
MTLTTAQKRYYDAMNEFEAITSKELEQTPEFSQDLLNDSD YLVITKNEAYAVALCMLDDDKLYLDETLVQSTCLDVEGET YYINFVVTNEDDFKLATDKDKEKHDKQEVIVKSELN

>WP_023553814.1
SEQ ID NO: 89
MTITTAQKRYYDAMNEFEAIISKELEQTPAFSQDLLNDSD YLVITKNEAYAVALCMLDDDKLYLDETLVQSTRLDIEDET YYINFVVTNEDDFKLATDEDKEKHDKQEVIIKSELN

>WP_031645843.1
SEQ ID NO: 90
MTITTAQKRYYDAMNEFEAITSKELEQTPEFSQDLLNDSD YLVITKNEAYAVALCMLDDDKLYIDETLVQSTCLDVEGET YYINFVVTNEDDFKLATDKDKEKHDKQEVIIKSELN

>WP_014930930.1
SEQ ID NO: 91
MTLTTAQKRYYDAMNEFEAIISKELEQTRAFSQDLLNDSD YLVITKNEAYAVDLCMLDDDKLYLDETLVQSTRLDIEDET YYINFVVTNEDDFKLATDEDKEKHDRQEVIIKSELN

>WP_070783480.1
SEQ ID NO: 92
MTITTAQKRYYDAMNEFEAITSKELEQTPEFSQDLLNDSD YLVVTKNEAYAAALCMLDDDKLYLDETLVQSTCLDVEGEI YYINFVVTNEDDFKLATDKDKEKHDKQEVIVKSELN

>WP_070040172.1
SEQ ID NO: 93
MTITTAQKRYYDAMNEFEAITSKGLEQTPEFSQDLLNDFD YLVITKNEAYAAALCMLDDEKLYLDETLVHSTRLDIEDDT YYINFVVTNEDDFKLATDEDKEKHDKQEVIIKRELN

>WP_012581437.1
SEQ ID NO: 94
MTITTAQKRYYDAMNEFEAIISKELEQTPAFSQDLLNDSD YLVITKNEAYAVALCLLDDDKLYLDETLVHSTRLDIEDET YYINFVVTNEDDFKLATDEDKEKHDKQEVIIKSELN

>WP_061107168.1
SEQ ID NO: 95
MTITTAQKRYYDAMNEFEAIISKELEQTPAFSQNLLNDSDY LVITKNEAYAVALCLLDDDKLYLDETLVHSTRLDIEDETY YINFVVTNEDDFKLATDEDKEKHDKQEVIIKSELN

>WP_070243058.1
SEQ ID NO: 96
MTITTAQKRYYDAMNEFEAITSKELEQTPAFSQDLLNDSD YLVITKNEAYAVALCLLDDDKLYLDETLVHSTRLDIEDET YYINFVVTNEDDFKLATDEDKEKHDKQEVIVKSELN

>WP_015967155.1
SEQ ID NO: 97
MTITTAQKRYYDAMNEFEAIISKELEQTPAFSQDLLNDSD YLVITKNEAYAVALCLLDDDKLYLDETLVHSTRLNIEDET YYINFVVTNEDDFKLATDEDKEKHDKQEVIIKSEFN

>WP_010989941.1
SEQ ID NO: 98
MTLTTAQKRYYDAMNEFEAITSKELEQTPEFSQDLLNDSD YLAVTKNEAYAVALCLLDDDKLYLDETLVHSTRLDIEDET YYINFVVTNEDDFKLATDEDKEKHDKQEVIIKSGLN

-continued

>WP_010991653.1

SEQ ID NO: 99

MTVTTAQKRYYDAMNEFEAITSKELEQTPEFSQDLLNDSD

YLAVTKNEAYAVALCLLDDDKLYLDETLVHSTRLDIEDET

YYINFVVTNEDDFKLATDEDKEKHDKQEVIIKSELN

>WP_068996515.1

SEQ ID NO: 100

MTLTTVQKRYYDAMNEFEAITSKELEQTPEFSQDLLNDSD

YLAVTKNEAYAVALCLLDDDKLYLDETLVHSTRFDIEDET

YYINFVVTNEDDFKLATDEDKEKHDKQEVIIKSELN

>WP_047934322.1

SEQ ID NO: 101

MTLTTVQKRYYDAMNEFEAITSKELEQTPEFSQDSLNDSD

YLAVTKNEAYAVALCLLDDDKLYLDETLVHSTRFDIEDET

YYINFVVTNEDDFKLATDEDKEKHDKQEVIIKSELN

>WP_003727803.1

SEQ ID NO: 102

MTITTAQKRYYDAMNEFEAIISKELEQTPAFSQDLLNDSD

YLAVTKNEAYAVALCLLDDDKLYLDETLVHSTRLDIEDET

YYINFVVTNEDDFKLATDEDKEKHDKQEVIIKSGLN

>WP_061114505.1

SEQ ID NO: 103

MTITTAQKRYYDAMNEFEAITSKELEQTPAFSQDLLNDSD

YLAVTKNEAYAVALCLLDDDKLYLDETLVHSTRLDIEDET

YYINFVVTNEDDFKLATDEDKEKHDKQEVIIKSGLN

>EFS02358.1

SEQ ID NO: 104

MAITLSQRKFYEAINEFEEMTENEVVTSPRIPQDYLNDGD

YVVITKSENYALNLCTTNLEGFEDRHFLDEKLIYSTFVET

YSGETYYIYITQTAEFDEDDAVEFLATQEQIYEYHKQEEQ

KTVILKMELS

>WP_069001896.1

SEQ ID NO: 105

MAQTEAQKIFYEAINEFEEMTNEEVVTSPRIPQDYLNDGD

YVVITKSENYALNLCTTDLEGFEDRYFLDEKLIYSTSVET

YTDETYYIYITQTTEFEEDNAVEFLATQEQIYEYHKQEEQ

KTVILKMELS

>WP_061665680.1

SEQ ID NO: 106

MTTARKKFYQAISEFEAMTGKDVERTPQIADEVLNDAEYI

AFTKTEKYALYLCTSNVEGLEDRYFLDEECLDSTFLETED

NETYYIHFLQETEFSEDDNEDELPLATEEQIEAYDKQEEL

KAVILKKELN

>WP_009917643.1

SEQ ID NO: 107

MRTTAQERLDNAINEFEEITNEEVVTSPRIPQDYLNDGDY

VVITKSENYALNLCTTNLEGFEDRHFLDEKLIYSTFVETY

SGETYYIYITQTAEFDEDDAVEFLATQEQIYEYHKQEEQK

TVILKMELS

-continued

>WP_061112069.1

SEQ ID NO: 108

MRTTAQERLDNAINEFEEITNEEVVTSPRIPQDYLNDGDY

VVITKSENYALNLCTTNLEGFEDRHFLDEKLIYSTFVETY

AGETYYIYITQTAEFDEDDAVEFLATQEQIYEYHKQEEQK

TVILKMELS

>WP_003745974.1

SEQ ID NO: 109

MRTTAQERLDNAINEFEEITNEEVVTSPLIPQDYLNDGDY

VVITKSENYALNLCTTNLEGFEDRHFLDEKLIYSTFVETY

SGETYYIYITQTAEFDEDDAVEFLATQEQIYEYHKQEEQK

TVILKMELS

AcrIIA3 protein sequences

>WP_014930691.1 (Listeria)

SEQ ID NO: 110

MFNKAEIMKQAWNWFNDSNIWLSDIEWVSYTDKEKSFSVC

LKAAWSKAKEEVEESKKESKHIAKSEELKAWNWAERKLGL

HFNISDDEKFTSVKDETKINFGLSVWACAMKAVKLHNDLF

PQTAA

>WP_068996201.1

SEQ ID NO: 111

MYNKAEIMKQAWNWFNDSNIWLSDIEWVSYTDKEKSFSVC

LKAAWSKAKEEVEESKKESKHIAKSEELKAWNWAERKLGL

HFNISDDEKFTSVKDETKINFGLSVWACAMKAVKLHNDLF

PQTAA

>WP_031646277.1

SEQ ID NO: 112

MYNKAEIMKQAWNWFNDSNIWLSDIEWVSYTDKEKSFSVC

LKGAWSKAKEEVEESKKESKHIAKSEELKAWNWAERKLGL

HFNISDDEKFTSVKDETKINFGLSVWACAMKAVKLHNDLF

PQTAA

>WP_003727804.1

SEQ ID NO: 113

MYNKAEIMKQAWNWFNDSNIWLSDIEWVSYTDKEKSFSVC

LKAAWSKAKEEVEESKKESKHIAKSEELKAWNWAERKLGL

HFNISDDEKFTSVKDETKINFGLSLWACAMKAVKLHNDLF

PQTAA

>WP_070776457.1

SEQ ID NO: 114

MYNKAEIMKQAWNWFNDSNVWLSDIEWISYTDKEKTFSVC

LKAAWSKAKEEVEESKKESKHIAKSEELKAWNWAERKLGL

HFNISDDEKFTSVKDETKINFGLSVWACAMKAVKLHNDLF

PQTAA

>WP_015455142.1

SEQ ID NO: 115

MYNKAEIMKQAWNWFNDSNIWLSDIEWVSYTDKEKSFSVC

LKAAWSKAKEEVEESKKESKYIAKSEELKAWNWAERKLGL

RFNISDDEKFTSVKDETKINFGLSVWACAMKAVKLHNDLF

PQTAA

-continued

>WP_070005112.1
SEQ ID NO: 116
MFNKAEIMKQAWNWFTDSNVWLSDIEWASYTDKEKSFSVC
LKAAWSKAKEEVEESKKESKHIAKSEELKAWNWAERKLGL
HFNISDDEKFTSVKDETKINFGLSVWACAMKAVKLHNDLF
PQTAA

>WP_068996392.1
SEQ ID NO: 117
MYNKAEIMKQAWNWFNDSNIWLSDIEWVSYTDKEKSFSVC
LKAAWSKAKEEVEEFKKESKYIAKSEELKAWNWAERKLGL
RFNISDDEKFTSVKDETKINFGLSVWACAMKAVKLHNDLF
PQTAA

>CUK89695.1
SEQ ID NO: 118
MKQAWNWFNDSNIWLSDIEWWSYTDKEKSFSVCLKAAWSK
AKEEVEESKKESKYIAKSEELKAWNWAERKLGLRFNISDD
EKFTSVKDETKINFGLSVWACAMKAVKLHNDLFPQTAA

>WP_060577772.1
SEQ ID NO: 119
DEKFTSVKDETKINFGLSVWACAMKAVKLHNDLFPQTAA

>WP_070295878.1
SEQ ID NO: 120
DEKFTSVKDETKINFGLSVWACAMKAVKLHNDLFPQTAA

>WP_061396065.1
SEQ ID NO: 121
MFNKAEIMKQAWNWFTDSNVWLSDIEWVSYTDKEKTFSVC
LKAAWSKAKEEVKEVEKEIKHISKSEELKAWNWAERKLGL
HFNISDDEKFTSVKDETKINFGLSVWACAMKAVKLHNDLF
PQTAA

>WP_039389302.1
SEQ ID NO: 122
MYNKAEIMKQAWNWFNDSNVWLSDIEWASYTDKEKTFSVC
LKAAWSKAKEEVKEVEKEIKHISKSEELKAWNWAERKLGL
HFNISDDEKFTSVKDETKINFGLSVWACAMKAVKLHNDLF
PQTAA

>WP_047934319.1
SEQ ID NO: 123
MFNKAEIMKQAWNWFTDSNVWLSDIEWASYTDKEKTFSVC
LKAAWSKAKEEVKEVEKEIKHISKSEELKAWNWAERKLGL
HFNISDDEKFTSVKDETKINFGLSVWACAMKAVKLHNDLF
PQTAA

>WP_069001240.1
SEQ ID NO: 124
MYNKAEIMKQAWNWFTDSNVWLSDIEWASYTDKEKTFSVC
LKAAWSKAKEEVKEVEKEIKHISKSEELKAWNWAERKLGL
HFNISDDEKFTSVKDETKINFGLSVWACAMKAVKLHNDLF
PQTAA

-continued

>WP_010991652.1
SEQ ID NO: 125
MFNKAEIMKQAWNWFTDSNVWLSDIEWWSYTDKEKTFSVC
LKAAWSKAKEEFKEVEKEIKHISKSEELKAWNWAERKLGL
HFNISDDEKFTSVKNETKMNFGLSVWACAMKAVKLHNDLF
PQTAA

>WP_061114504.1
SEQ ID NO: 126
MYNKAEIMKQAWNWFTDSNVWLSDIEWASYTDKEKTFSVC
LKAAWSKAKEEVKEVEKEIKHISKSEELKAWNWAERKLGL
HFNISDDEKFTSVKDETKINFGLSVWACAMKAVKLHNDLF
PQTVA

>WP_014930931.1
SEQ ID NO: 127
MYNKAEIMKQAWNWFNDSNVWLSDIEWASYTDKEKTFSVC
LKAAWSKAKEEVKEVEKEIKHISKSEELKAWNWAERKLGL
HFNISDDEKFTSVKDETKINFGLSVWACAMKAVKLHSHLF
PQTAA

>WP_069002681.1
SEQ ID NO: 128
MYNKAEIMKQAWNWFTDSNVWLSDIEWASYTDKEKTFSVC
LKAAWSKAKEEVKEVEKEIKHISKREELKAWNWAERKLGL
HFNISDDEKFTSVKDETKINFGLSVWACAMKAVKLHNDLF
PQTVA

>WP_012581436.1
SEQ ID NO: 129
MFNKAEIMKQAWNWFTDSNVWLSDIEWVSYTDKEKTFSVC
LKAAWSKAKEEVKEVEKEIKHISKSEELKAWNWAERKLGL
RFNISDDEKFTSVKDETKQHFGLSVWACAMKAVKLHNDLF
PQTAA

>WP_010989940.1
SEQ ID NO: 130
MYNKAEIMKQAWNWFNDSNIWLSDIEWVSYTDKEKSFSVC
LKAAWSKAKEEVEESKKESKHIAKSEELKAWNWAEIKLGL
RFNISDDEKFTSVKDETKMNFDLNVWACAMKAVKLHNDLF
PQTAA

>WP_015967156.1
SEQ ID NO: 131
MYNKAEIMKQAWNWFTDSNVWLSDIEWVSYTDKEKTFSVC
LKAAWSKAKEEVKEVEKEIKHISKSEELKAWNWAERKLGL
RFNISDDEKFTSVKDETKQHFGLSVWACAMKAVKLHNDLF
PQTAA

>WP_031645844.1
SEQ ID NO: 132
MYNKAEIMKQAWNCFNDSNVWLSDIEWWSYTDKEKTFSVC
LKAAWSKAKEEIEKSKKESKHIAKSEELKAWNWAERKLGL
RFNISDDEKFTSVKDETKQHFGLSVWACAMKAVKLHNDLF
PQTAA

>WP_031691597.1
SEQ ID NO: 133
MYNKAEIMKQAWNCFNDSNVWLSDIEWWSYTDKEKTFSVC
LKAAWSKAKEEIEESKKESKHIAKSEELKAWNWAERKLGL
RFNISDDEKFTSVKDETKQHFGLSVWACAMKAVKLHNDLF
PQTAA

>WP_023553812.1
SEQ ID NO: 134
MYNKSEIMQQAWNWFRDSSVWLSDIEWWSYTDKEKTFSVC
LKAAWSKAKEEVEESKKESKHIAKSEELKAWNWAESKLGL
RFNISDDEKFTSVKDETKINFGLSVWACAMKAVKLHNDLF
PQTAA

>WP_069029656.1
SEQ ID NO: 135
MYNKAEIMKQAWNWFTDSNVWLSDIEWASYTDKEKTFSVC
LKAAWSKAKEEVKEVEKEIKHISKREELKAWNLAERKLGL
HFNISDDEKFTSVKDETKINFGLSVWACAMKAVKLHNDLF
PQTVA

>WP_069001927.1
SEQ ID NO: 136
MFNKAEIMKQAWNWFTDSNVWLSDIEWASYTDKEKTFSVC
LKAAWSKAKEEVKEVEKEIKHISKSEELKAWNWAERKLGL
HFNISDDEKFTSVKDETKINFGLSVWACAMKAVKLHN

>WP_064659125.1
SEQ ID NO: 137
MKKVTYDKSGIMKEAWNLFNNDDITLADFEHLGWMEWKSE
KTFALCLKEAWGREKEVVERVNQKFANAETSEEAKAWDWA
CKKLGVAFEMDAYTKMTNVEDMEKEAWPGTSVWSLAMRAV
KLHMEVAA

>WP_012678885.1
SEQ ID NO: 138
MRYNKSEIMKNAWAMFNSCNWGAENFKFVSVEEKTFAACL
KEAWAEEKEYVEEKIKESANAPKSEEAKAWDWACRKLNAN
KLQNVEATDKVAWWSEMAKEMWSSNIWAQAIKAVKLHIKL
FAA

>WP_037595340.1
SEQ ID NO: 139
MKYNKSEIMKNAWTMFNDDNFDTSYYEYATAEVYGQKTFS
ECLKESWGREKAYQEEKEKRLVDAPKSEEAKAWDWACRKL
NVNELQNIDATDKVFYVEGMAKEMWSSNVWAQAIKAVKLH
IELFVA

>WP_009730539.1
SEQ ID NO: 140
MKKVAYDKSGIMKEAWEMFNRNYQICDFEYADFSGREYFE
YASFADCLKEAWAHEKEVVERVNQKYADAETSEEVKAWDW
ACKKLGVAFEMDAYTKITNVEGMEKEAWPGTSVWSLAMRA
VKLHMEVAA

>WP_071127625.1
SEQ ID NO: 141
MAKYNKSEIMTQAWTLFNSDNFDTCDYEYTTALVYGQKNF
SDCLKEAWGREKAIVERMAEQEANAPLSEEAKAWDWACRK
LGVTAEVTAVEKVRYVDDMAKEMWSANVWKQAIKAVQLYA
TVA

>AGM98706.1
SEQ ID NO: 142
MAKYNKSEIMTQAWTLFNSDNFDTCDYEYATALVYGQKTF
SDCLKEAWGREKAIVERMAEKEANAPLSEEAKAWDWACRK
LGVTAEVTAVEKVRYVDDMAKEMWSTNVWKQAIKAVQLYA
TVA

>WP_012767357.1
SEQ ID NO: 143
MAKYNKSEIMKNAWAMFNSYEWDVENFKFVSAENKTFSNC
LKEAWAEEKEYVERKAKETAEAPKSEEAKAWDWACRKLNV
NDLQNIDATDKVFYVVDMQKEMWTSNVWAQAIKAVELYVK
LGLA

>WP_023611744.1 (Streptococcus)
SEQ ID NO: 144
MTKYNKSEIMKNAWAMFNSYEWDVENFKFVSAENKTFSNC
LKEAWAEEKEYVERKAKETAEAPRSEEAKAWDWACRKLNV
NDLQNIDATDKVFYVVDMQKEMWTSNVWAQAIKAVELYVK
LGLA >WP_066028552.1
SEQ ID NO: 145
MTKYNKSEIMKNAWAMFNSYEWDVENFKFVSAENKTFSNC
LKEAWAEEKEYVERKAKETAEAPKSEEAKAWDWACRKLNV
NDLQNIDATDKVFYVVDMQKEMWTSNIWAQAIKAVELYVK
LGLA >WP_003055844.1
SEQ ID NO: 146
MTKYNKSEIMKNAWAMFNSYEWDVENFKFVSAENKTFSNC
LKEAWAEEKEYVERKAKEAAEASKSEEAKAWDWACRKLNV
NDLQNIDATNKVFYVVDMQKEMWTSNVWAQAIKAVELYVK
LGLA AcrIIA4 protein sequences
>WP_003723290.1
SEQ ID NO: 147
MNINDLIREIKNKDYTVKLSGTDSNSITQLIIRVNNDGNE
YVISESENESIVEKFISAFKNGWNQEYEDEEEFYNDMQTI
TLKSELN >WP_046376634.1
SEQ ID NO: 148
MNINELIREIKNKDYTAKLSGTDSNSITQLIIRVNNDGNE
YVISESENESIVEKFISAFKNGWNQEYEDEEEFYNDMQTI
TLKSELN -continued

>WP_069001216.1
SEQ ID NO: 149
MNINELIREVKNKDYTAKLSGTDSNSITQLIIRVNNDGNE

YVISESENESIVEKFISAFKNGWNQEYEDEEEFYNDMQTI

TLKSELN

>KLI10194.1
SEQ ID NO: 150
MNINELIREIKNKDYTAKLSGTDSNSIAQLIIRVNNDGNE

YVISESENESIVEKFISAFKNGWNQEYEDEEEFYNDMQTI

TLKSELN

>WP_031667946.1
SEQ ID NO: 151
MNINELIREIKNKDYTAKLSGTDSNSITQLIIHVNNDGNE

YVISESENESIVEKFISAFKNGWNQEYEDEEEFYNDMQTI

TLKSELN

>WP_070295973.1
SEQ ID NO: 152
MNINDLIREIKNKDYTVKLSGTDSNSITQLIINVNNDGNE

YGISESNFESIVEKFVSNFENGWDGAYEDEEEFYNDMQAI

ILKSELN

>WP_061107115.1
SEQ ID NO: 153
MNINDLIREIKNKDYTVKLSGTDSNSITQLIINVNNDGNE

YGISESNFESIVEKFVSNFENGWDGAYEDEEEFYNDMQAI

ILKSESN

>WP_060954847.1
SEQ ID NO: 154
MNISELIREIKNKDYTVRLEGTDDNSITKLIIDVDNDGNE

YVISESKNESIAEKFASTFKNGWNKEYEDEEEFYNDMQSI

ILKSELN

>WP_012582157.1
SEQ ID NO: 155
MNISELIREIKNKDYAVRLEGTDDNSITKLIIDVDNDGNE

YVISESKNESIAEKFASTFKNGWNKEYEDEEEFYNDMQSI

ILKSELN

>CAR82813.1
SEQ ID NO: 156
MAGYLKRYAEDRGWTLYRLAKESHLSDSTLRTADLTTLNK

LSVINIKKISEAVGETPGEVLDDLIKFEERVEKMNISELI

REIKNKDYAVRLEGTDDNSITKLIIDVDNDGNEYVISESK

NESIAEKFASTFKNGWNKEYEDEEEFYNDMQSIILKSELN

>WP_003740262.1
SEQ ID NO: 157
MNLKELVREIKNKDYTAKLSGTDSNSITQLIIHVNNDGNE

YGISESNFESIVEKFVSTFENGWDGAYEDEEEFYNDMQDI

VNRHFK

>WP_061385557.1
SEQ ID NO: 158
MNLKELVREIKNKDYTAKLSGTDSNSITQLIIHVNNDGNE

YGISESNFESIVEKFVSNFENGWDGAYEDEEEFYNDMQDI

VNRHFK

>CUL91420.1
SEQ ID NO: 159
MKINELVREIKSRDYTVRLNGTDSNSITKLIIDVNNDGNE

YVISERQDTSIVESFADSFIDGWTGTYEDEEDFYNDMQEI

AQDIILETLKEAFENNNYNTDEVDTDLFDGYQIKLAMEYD

NIGELATSVNKTKHFTAYMDASTDFMIIEKY

>YP_008239985.1
SEQ ID NO: 160
MSIIAIKKEIHAKGYKVTGTHQGYIAQINFDGTGNEYPLP

ATWDEFIETFKDGWNGTYEDEQAFFNDMQEVALKEILDEL

TGALFCQDITTYDFTIDDVKKKVITLDKPTFEEDAEDLII

EFDSTCFWDATVENDKIKITVRNKSRY

>AII27415.1
SEQ ID NO: 161
MSIIAIKKEIHAKGYKVTGTHQGYIAQINFDGTGNEYPLP

ATWDEFIETFKDGWNGTYEDEQAFFNDMQEIALDEILDEL

IDVLYNLDITTYNFTIDDS

>YP_001468568.1
SEQ ID NO: 162
MSIIAIKKEIHAKGYKVTGTHQGYIAQINFDGTGNEYPLP

ATWDEFIETFKDGWNGTYEDEQAFFNDMQEIALEEILDEL

TGALFCQDITTYDFTIDDVKKKVITLDKPTFEEDAEDLII

EFDSTCFWDATVENDKIKITVRNKSRY

>YP_009043548.1
SEQ ID NO: 163
MSIIAINKEIRAKGYKVTGTHQGYIAQINFEGTGNEYPLP

ATWDEFIETFKDGWNGTYEDEQAFFNDMQEIALDEILDEL

IDVLYNLDITTYNFTIDDVKKKVITLNKPIDEEETEDLVQ

EFNVTCFWDATVEDDKVKVTIRNKNRAIS

>AID17477.1
SEQ ID NO: 164
MSTTAINKEIHAKGYKVTGTHQGYIAQINFDGTGNEYPLP

ATWEKFIETFKDGWDGTYEDEQAFFNDMQEIALDEILDEL

IDVLYNLDITTYNFTIDDVKKKVITLNKPIDEEETEDLVQ

EFNVTCFWNAIVEDDKVKITVRNKSK

>YP_009043010.1
SEQ ID NO: 165
MSTTAINKEIHAKGYKVTGTHQGYIAQINFDGTGNEYPLP

ATWEEFIETFKDGWDGTYEDEQAFFNDMQEIALDEILDEL

-continued

IDVLYNLDITTYNFTIDDVKKKVITLNKPIDEEETEDLVQ

EFNVTCFWNAIVEDDKVKITVRNKSK

>AID17274.1

SEQ ID NO: 166

MSTTAINKEIHAKGYKVTGTHQGYVAQINFDGTGNEYPLP

ATWEEFIETFKDGWDGTYKDEQAFFNDMQEIALDEILDEL

IDTLYNLDITTYDFTIDDIKKKVITLDKPTDREETEDLVQ

EFNVTCFWNAIVEDDKVKVTVRNKSK

>AAY53411.1

SEQ ID NO: 167

MTGTHQGYIAQINFDGTGNEYPLPATWDEFIETFKDGWNG

TYEDEQAFFNDMQEVALKEILDELIDVLYNLDITTYNFTI

DDVKKKVITLNKPTDEEDAEDLVIEFDSTCFXDATVENDK

IKVTVRNKSK

-continued

>YP_009044467.1

SEQ ID NO: 168

MSTTAINKEIHAKGYKVTGTHQGYMAQINFDGTGNEFPLP

ATWEEFIETFKDGWDGTYEDEQAFFNDMQEVALEELLDEL

TDVFYNLDITAYDFTVDDVKKKVITLDKPTDREETEDLVQ

EFKATCFWNAVVEDDKVKVTIRNKNRAIS

Additional protein sequences
AcrIIA3b.3, OLF47316.1

SEQ ID NO: 169

MQFVVTNKSELFKFAWKIFKANKDIAFSECLQNAWFQYKR

YLNREAIKAAQQRKLAKFIADTENEEVKAWNWAEKKLGVA

LNLTDAEKERNVRNMYKEMWNANVWATAIKAVKLHMEIG

AcrIIA4b.2, YP_008240385.1

SEQ ID NO: 170

MNELRSLEMSINAKKYDTRLESGNRVLNIGFGDGEDYPVC

SSSRYSLKESFIECFKDGWSGTYRDEKELMEDMQEIAQEL

ILEELTDIFEYYEFNTDEIDTDLFKGFTFDVDSDLEDSMA

LMKAINATKYFEARSSSWYASFEVSYIG

What is claimed is:

1. A method of inhibiting a Cas9 polypeptide in a cell, the method comprising, introducing a Cas9-inhibiting polypeptide into a cell, wherein:

the Cas9-inhibiting polypeptide is heterologous to the cell, the Cas9-inhibiting polypeptide is at least 95% identical to SEQ ID NO:1; and the Cas9 polypeptide is present in the cell before the introducing or the Cas9 polypeptide is introduced into the cell after the introducing, thereby inhibiting the Cas9 polypeptide in a cell.

2. The method of claim 1, comprising contacting the Cas9 inhibiting polypeptide with a Cas9 polypeptide in the cell.

3. The method of claim 1, wherein the Cas9-inhibiting polypeptide comprises SEQ ID NO:1.

4. The method of claim 1, wherein the cell comprises the Cas9 polypeptide before the introducing.

5. The method of claim 4, wherein the cell comprises an expression cassette comprising a promoter operably linked to a polynucleotide encoding the Cas9 polypeptide.

6. The method of claim 5, wherein the promoter is inducible and the method comprises contacting the cell with an agent or condition that induces expression of the Cas9 polypeptide in the cell prior to the introducing.

7. The method of claim 1, wherein the cell comprises the Cas9 polypeptide after the introducing.

8. The method of claim 7, wherein the promoter is inducible and the method comprises contacting the cell with an agent or condition that induces expression of the Cas9 polypeptide in the cell after to the introducing.

9. The method of claim 1, wherein the introducing comprises expressing the Cas9-inhibiting polypeptide in the cell from an expression cassette that is present in the cell and heterologous to the cell, wherein the expression cassette comprises a promoter operably linked to a polynucleotide encoding the Cas9-inhibiting polypeptide.

10. The method of claim 9, wherein the promoter is an inducible promoter and the introducing comprises contacting the cell with an agent that induces expression of the Cas9-inhibiting polypeptide.

11. The method of claim 1, wherein the introducing comprises introducing an RNA encoding the Cas9-inhibiting polypeptide into the cell and expressing the Cas9-inhibiting polypeptide in the cell from the RNA.

12. The method of claim 1, wherein the introducing comprises inserting the Cas9-inhibiting polypeptide into the cell or contacting the cell with the Cas9-inhibiting polypeptide.

13. The method of claim 1, wherein the method occurs ex vivo.

14. The method of claim 13, wherein the cells are introduced into a mammal after the introducing and contacting.

15. A cell comprising a Cas9-inhibiting polypeptide, wherein the Cas9-inhibiting polypeptide is heterologous to the cell and the Cas9-inhibiting polypeptide is at least 95% identical to SEQ ID NO:1.

16. A polynucleotide comprising a promoter operably linked to a nucleic acid encoding a Cas9-inhibiting polypeptide, wherein the Cas9-inhibiting polypeptide has at least 95% identity to SEQ ID NO: 1, and wherein the promoter is heterologous to the nucleic acid.

17. A vector comprising the polynucleotide of claim 16.

18. A pharmaceutical composition comprising the polynucleotide of claim 16.

19. A delivery vehicle comprising the polynucleotide of claim 16.

20. The delivery vehicle of claim 19, wherein the delivery vehicle is a liposome or nanoparticle.

* * * * *